United States Patent [19]

Manning et al.

[11] Patent Number: 5,302,610
[45] Date of Patent: Apr. 12, 1994

[54] RENAL-SELECTIVE BIPHENYLMETHYL IMIDAZOLE ANGIOTENSIN II ANTAGONISTS FOR TREATMENT OF HYPERTENSION

[75] Inventors: Robert E. Manning, St. Louis; David B. Reitz, Chesterfield, both of Mo.

[73] Assignee: G. D. Searle & Co., Chicago, Ill.

[21] Appl. No.: 810,321

[22] Filed: Dec. 19, 1991

Related U.S. Application Data

[63] Continuation of Ser. No. 566,208, Aug. 10, 1990, abandoned.

[51] Int. Cl.$^5$ .............. A61K 31/415; A61K 31/495; C06D 241/04; C06D 233/54; C06D 257/04; C06D 265/30
[52] U.S. Cl. .................. 514/381; 514/398; 514/399; 514/400; 514/215; 514/235.8; 548/251; 548/252; 548/253; 548/254; 548/316.4; 548/324.5; 548/325.1; 548/326.5; 548/328.1; 548/333.5; 548/334.5; 548/335.1; 548/338.1; 548/338.5; 544/370; 544/139
[58] Field of Search .............. 548/252, 341, 355.1, 548/251, 253, 316.4, 328.1, 338.1; 514/399, 381, 398, 400

[56] References Cited

U.S. PATENT DOCUMENTS

| 4,816,463 | 3/1989 | Blankley et al. | 514/293 |
| 4,880,804 | 11/1989 | Carini et al. | 548/234 X |

FOREIGN PATENT DOCUMENTS

| 253310 | 1/1988 | European Pat. Off. | 548/253 |
| 323841 | 12/1989 | European Pat. Off. | 548/253 |

OTHER PUBLICATIONS

P. C. Wong et al., *J. Pharmacol. Exp. Ther.*, 247(1), 1-7 (1988).
A. T. Chiu et al., *European J. Pharmacol.*, 157, 13-21 (1988).
A. T. Chiu et al., *J. Pharmacol. Exp. Ther.*, 250(3).
J. J. Kyncl et al., *Adv. Biosc.*, 20, 369-380 (1979).
M. Orlowski et al., *J. Pharmacol. Exp. Ther.*, 212, 167-172.

(List continued on next page.)

*Primary Examiner*—Floyd D. Higel
*Attorney, Agent, or Firm*—J. Timothy Keane

[57] ABSTRACT

Renal-selective compounds are described which, in one embodiment, are prodrugs preferentially converted in the kidney to compounds capable of blocking angiotensin II (AII) receptors. These prodrugs are conjugates formed from two components, namely, a first component provided by an AII antagonist compound and a second component which is capable of being cleaved from the first component when both components are chemically linked within the conjugate. The two components are chemically linked by a bond which is cleaved selectively in the kidney, for example, by an enzyme. The liberated AII antagonist compound is then available to block AII receptors within the kidney. Conjugates of particular interest are glutamyl derivatives of biphenylmethyl 1H-substituted imidazole compounds, of which N-acetyl-L-glutamic acid, 5-[[4'-[2-butyl-4-chloro-5-(hydroxymethyl)-1H-imidazol-1-ylmethyl][1,1'-biphenyl]-2-yl]carbonyl]hydrazide (shown below) is an example:

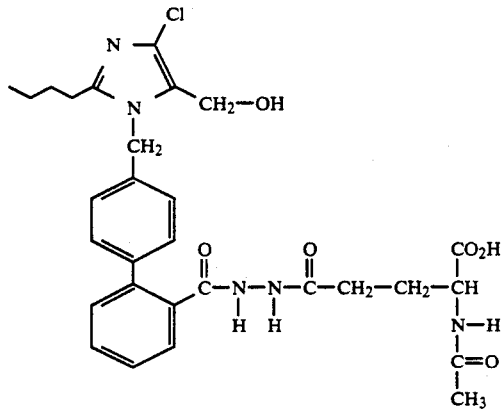

47 Claims, 4 Drawing Sheets

OTHER PUBLICATIONS

S. D. J. Magnan et al., *J. Med. Chem.*, 25, 1018–1021 (1982).

K. G. Hofbauer et al., "CGP22979A, a Renal Vasodilator with Natriuretic Properties", *J. Pharmacol. Exp. Ther.*, vol. 232, 838–844 (1985).

D. P. Worth et al., *Clin. Sci.*, 69, 207–214 (1985).

R. F. Jeffrey et al., *Br. J. Clin. Pharmac.*, 25, 195–201 (1988).

*J. Pharmacol. Exp. Ther.*, 235 (3), 778–782 (Dec. 1985).

Chang, R. S. L. et al., *Mol. Pharmacol.*, 37 (3), 347–351 (1990).

Smits et al., "Preferential Renal Vasodilator Effects . . . ", *J. Pharmacol. Exp. Ther.*, 232 (3), 845–849 (Mar. 1985).

*J. Pharmacol. Exp. Ther.*, 99 (1), 15–20 (Jan. 1990).

*J. Pharmacol. Exp. Ther.*, 250 (1), 79–85 (Jul. 1989).

*J. Pharmacol. Exp. Ther.*, 252 (3), 1255–1260 (Mar. 1990).

Burger, A. "A Guide to the Chemical Basis of Drug Design", John Wiley & Sons, New York p. 15, (1983).

Denkewalter et al., Progress in Drug Research, vol. 10, pp. 510–512 (1966).

Burger, A Medicinal Chemistry, 2nd Ed., New York, pp. 565–571, 578–581, 600–601 (1960).

RENAL-SELECTIVE BIPHENYLMETHYL IMIDAZOLE ANGIOTENSIN II ANTAGONISTS FOR TREATMENT OF HYPERTENSION

This is a continuation of application Ser. No. 07/566,208 filed Aug. 10, 1990, now abandoned.

FIELD OF THE INVENTION

This invention is n the field of cardiovascular therapeutics and relates to a class of compounds useful in control of hypertension. Of particular interest is a class of prodrugs of angiotensin II antagonists which, when selectively hydrolyzed in the kidney, provide hypertension control.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, an octapeptide which is the primary active species of this system. Angiotensin II is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Exp. Ther.*, 247(1), 1–7 (1988)]. Also, the sodium salt of 2-butyl-4-choloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.*, 157, 3121 (1988)]. A family of 1-benzylimidazole-5-acetate derivatives has been shown to have competitive angiotensin II antagonist properties [A. T. Chiu et al, *J. Pharmacol. Exp. Ther.*, 250(3), 867–874 (1989)]. U.S. Pat. No. 4,816,463 to Blankey et al describes a family of 4,5,6,7-tetrahydro-1H-imidazo(4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published Jan. 20, 1988, describes a series of aralkyl imidazole compounds, including in particular a family of biphenylmethyl substituted imidazoles, as antagonists to the angiotensin II receptor. EP No.323,841 published Jul. 12, 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

One disadvantage of these angiotensin II antagonist compounds is that the desired hypertension-reducing effect may be offset by hypotension-induced compensatory stimulation of the renin-angiotensin system or stimulation of the sympathetic nervous system, either of which may result in promotion of sodium and water retention. Also, some angiotensin II antagonists may have toxicological effects systemically which precludes their use at doses necessary to be effective in reducing blood pressure.

To avoid such systemic side effects, drugs may be targetted to the kidney by creating a conjugate compound that would be a renal-specific prodrug containing the targetted drug modified with a chemical carrier moiety. Cleavage of the drug from the carrier moiety by enzymes predominantly localized in the kidney releases the drug in the kidney. Gamma glutamyl transpeptidase and acylase are examples of such cleaving enzymes found in the kidney which have been used to cleave a targetted drug from its prodrug carrier within the kidney.

Renal targetted prodrugs are known for delivery of a drug selectively to the kidney. For example, the compound L-$\gamma$-glutamyl amide of dopamine when administered to dogs was reported to generate dopamine in vivo by specific enzymatic cleavage by $\gamma$-glutamyl transpeptidase [J. J. Kyncl et al, *Adv. Biosc.*, 20, 369–380 (1979)]. In another study, $\gamma$-glutamyl an N-acyl-$\gamma$-glutamyl derivatives of the anti-bacterial compound sulfamethoxazole were shown to deliver relatively high concentrations of sulfamethoxazole to the kidney which involved enzymatic cleavage of the prodrug by acyl-amino acid deacylase and $\gamma$-glutamyl transpeptidase [M. Orlowski et al, *J. Pharmacol. Exp. Ther.*, 212, 167–172 (1980)]. The N-$\gamma$-glutamyl derivatives of 2-, 3-, or 4-aminophenol and p-fluoro-L-phenylalanine have been found to be readily solvolyzed in vitro by $\gamma$-glutamyl transpeptidase [S. D. J. Magnan et al, *J. Med. Chem.*, 25, 1018–1021 (1982)]. The hydralazine-like vasodilator 2-hydrazino-5-n-butylpyridine (which stimulates guanylate cyclase activity) when substituted with the N-acetyl-$\gamma$-glutamyl residue resulted in a prodrug which provided selective renal vasodilation [K. G. Hofbauer et al, *J. Pharmacol. Exp. Ther.*, 232, 838–844 (1985)]. The dopamine prodrug $\gamma$-L-glutamyl-L-dopa ("gludopa") has been shown to be relatively specific for the kidney and to increase renal blood flow, glomerular filtration and urinary sodium excretion in normal subjects [D. P. Worth et al, *Clin. Sci.*, 69, 207–214 (1985)]. In another study, gludopa was reported to be an effective renal dopamine prodrug whose activity can be blocked by the dopa-decarboxylase inhibitor carbidopa [R. F. Jeffrey et al, *Br. J. Clin. Pharmac.*, 25, 195–201 (1988)]. A class of 4-ureido derivatives of isoquinolin-3-ol has been investigated for renal specific effects such as increases in renal vasodilation and renal blood flow [R. M. Kanojia et al, *J. Med. Chem.*, 32, 990–997 (1989)].

BRIEF DESCRIPTION OF THE DRAWING FIGURES

DESCRIPTION OF THE INVENTION

Figure 1:
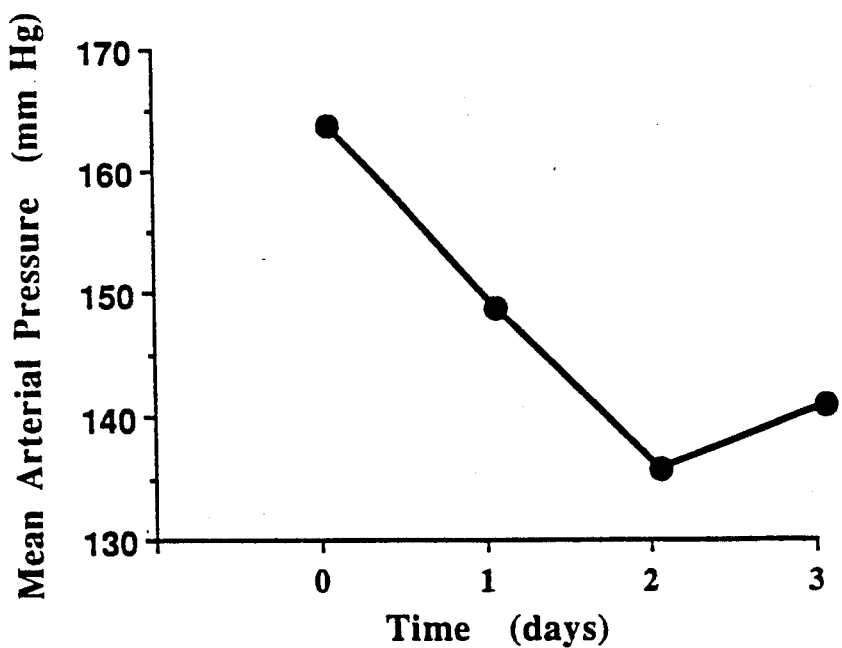
FIG. 1 is a graph showing reduction in mean arterial pressure by intravenous administration of a conjugate of the invention to a spontaneously hypertensive rat.

Treatment of chronic hypertension or sodium-retaining disorders such as congestive heart failure, cirrhosis and nephrosis, may be accomplished by administering to a susceptible or afflicted subject a therapeutically-effective amount of a renal-selective prodrug capable of causing blood-pressure reducing effects by selective action in the kidney. An advantage of such renal-selective prodrug therapy resides in reduction or avoidance of adverse side effects associated with systemically-acting drugs.

Advantages of a renal-selective antihypertensive compound are several. First, the renal-selective compound is targetted at those pathophysiological mechanisms which occur primarily in the kidney. Second, the regulation of other organ systems is unaffected; thus, normal physiological regulation of other organ systems is maintained. Third, fewer side-effects may be anticipated, since the compound remains inactive until cleaved in the kidneys. Similarly, fewer negative drug-drug interactions may be anticipated. Finally, since a renal-selective accumulation of active compound may occur, which is not dependent on plasma levels of the parent compound, lower doses of the renal-selective compound compared to active parent compound may be used.

A renal-selective prodrug is provided by a conjugate comprising a residue of an angiotensin II antagonist compound, which conjugate is renal selective. The conjugate will typically comprise a first component and a second component connected together by a cleavable or hydrolyzable bond. The term "renal-selective", as used to characterize a conjugate of the invention, embraces any of the following four pharmacological events: (1) the conjugate is selectively taken up by the kidney and is selectively cleaved in the kidney; (2) the conjugate is not taken up selectively by the kidney, but is selectively cleaved in the kidney; (3) the conjugate is selectively taken up by the kidney and then cleaved in the kidney; or (4) where the conjugate itself is active as an angiotensin II antagonist, the conjugate is selectively taken up by the kidney without cleavage of the hydrolyzable bond.

The first component of a conjugate of the invention is a residue derived from an antagonist compound capable of inhibiting angiotensin II (AII) receptors, especially those AII receptors located in the kidney. The second residue is capable of being cleaved from the first residue preferentially. Cleaving of the first and second residues may be accomplished by a variety of mechanisms. For example, the bond may be cleaved by an enzyme in the kidney.

The residue providing the first component may be characterized as the "AII antagonist active" residue. Such "active" residue may be provided by a compound having AII antagonist activity or by a metabolite of such compound having AII antagonist activity. The residue providing the second component may be characterized in being capable of forming a cleavable bond connecting the "active" first residue and the second residue. Such bond is cleavable by an enzyme located in the kidney. In a preferred embodiment, this cleavable bond is typically a hydrolyzable amide bond, that is, a bond between a carbonyl-terminated moiety and a reactive nitrogen-terminated moiety, such as an amino-terminated moiety, which may be cleaved by an enzyme found in the kidney, but which is not cleaved substantially by enzymes located in other organs or tissues of the body. Preferred bond-cleaving enzymes would be found predominantly in the kidney.

The conjugate containing the residue of an AII antagonist compound and containing the cleavable fragment or residue may possess AII antagonist activity comparable to, or more than, or less than, the AII antagonist compound which forms the conjugate. In one embodiment of the invention, the conjugate will have AII receptor blocking activity comparable to the AII antagonist component forming the conjugate. In another embodiment of the invention, the conjugate will have AII receptor blocking activity less than the AII receptor blocking activity forming the conjugate. One advantage of such differential activity between the conjugate and the AII antagonist component is that certain side effects associated with non-renal, systemic AII receptor blocking may be avoided or reduced. For example, at least one conjugate of the invention has been found to have a very large differential in AII receptor blocking activities between the conjugate and the AII antagonist component forming the conjugate. Such differential activity is advantageous in that therapeutically-effective antihypertensive doses of the conjugate may be administered to give renal-selective AII receptor blocking action resulting from kidney-specific enzyme hydrolysis or metabolism of the conjugate to free the active AII receptor blocker within the kidney. Inasmuch as this renal-selective conjugate has relatively low AII receptor blocking activity, compared to the AII receptor compound forming the conjugate, this conjugate will have fewer adverse side effects associated with unwanted systemic interaction with non-renal AII receptors such as found in the vascular bed.

DETAILED DESCRIPTION OF THE INVENTION

The first residue of the conjugate may be selected from any class of compounds, or metabolites thereof, having angiotensin II antagonist activity. An example of one such class of angiotensin II antagonist compounds is provided by a class of biphenylmethyl 1H-substituted-1,3-imidazole compounds defined by Formula I:

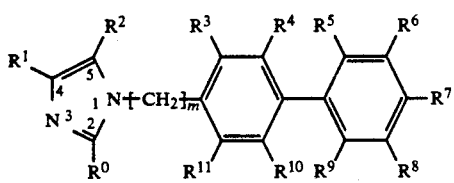

wherein m is a number selected from one to four, inclusive;

wherein each of $R^0$ through $R^{11}$ is independently selected from hydrido, alkyl, hydroxyalkyl, halo, haloalkyl, cycloalkyl, cycloalkylalkyl, formyl, alkoxy, aralkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cyclohetero-containing groups has one or more ring atoms selected from oxygen, sulfur and nitrogen atoms, and wherein each of $R^0$ through $R^{11}$ may be further independently selected from amino and amido radicals of the formula

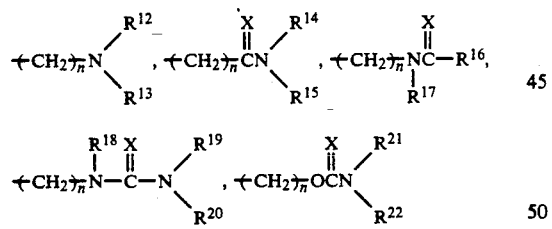

and

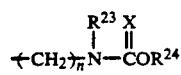

wherein X is oxygen atom or sulfur atom;
wherein each n is a number independently selected from zero to six, inclusive;
wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together, $R^{14}$ and $R^{15}$ taken together, $R^{16}$ and $R^{17}$ taken together, $R^{19}$ and $R^{20}$ taken together and $R^{21}$ and $R^{22}$ taken together may each form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein $R^{12}$ and $R^{13}$ taken together, $R^{14}$ and $R^{15}$ taken together, $R^{19}$ and $R^{20}$ taken together and $R^{21}$ and $R^{22}$ taken together may each form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;

and wherein each of $R^3$ through $R^{11}$ may be further independently selected from hydrido and haloalkyl, and from acidic moieties of the formula $-Y_nA$ wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{24}$, Y and A groups having a substitutable position may be substituted with one or more groups selected from hydroxy, alkyl, alkenyl, alkynyl, aralkyl, hydroxyalkyl, trifluoromethyl, difluoroalkyl, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, carboxyl, mercapto, mercaptocarbonyl, alkylthio, arylthio, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

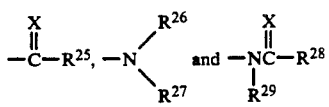

wherein D is selected from oxygen atom and sulfur atom and $R^{30}$ is selected from hydrido, alkyl, cycloalkyl, cycloalkylalkyl, aralkyl and aryl; wherein each of $R^{25}$, $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{26}$, $R^{27}$, $R^{28}$, $R^{29}$, $R^{31}$ and $R^{32}$ is further independently selected from amino and amido radicals of the formula

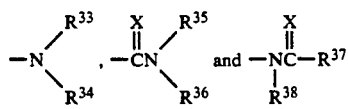

wherein X is oxygen atom or sulfur atom;
wherein each of $R^{33}$, $R^{34}$, $R^{35}$, $R^{36}$, $R^{37}$ and $R^{38}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl, and wherein $R^{26}$ and $R^{27}$ taken together and $R^{28}$ and $R^{29}$ taken together may each form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein $R^{26}$ and $R^{27}$ taken together and $R^{31}$ and $R^{32}$ taken together may each form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;
with the proviso that at least one of said $R^1$ through $R^{24}$, Y and A substituents contains a terminal primary or secondary amino moiety or a moiety convertible to a primary or secondary amino moiety;
or a tautomer thereof or a pharmaceutically-acceptable salt thereof.

Conjugates of the invention are therapeutically effective in treatment of cardiovascular disorders by acting directly, or by providing cleavable components selected from Formula I compounds which act directly, as antagonists to, or blockers of, the angiotensin II (AII) receptor. Thus, conjugates of Formula I would be therapeutically effective in treatment of cardiovascular disorders or would be precursors to, or prodrugs of, therapeutically-effective compounds.

Preferred compounds of Formula I, from which a cleavable component may be selected, are all characterized in having a substituent, other than hydrido, at each of the four- and five-positions of the imidazole ring. Such substituents are selected from the aforementioned $R^1$ and $R^2$ groups.

The phrase "acidic group selected to contain at least one acidic hydrogen atom", as used to define the $-Y_nA$ moiety, is intended to embrace chemical groups which, when attached to any of the $R^3$ through $R^{11}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a pKa in a range from about one to about twelve. More typically, the Formula I compound would have a pKa in a range from about two to about seven. An example of an acidic group containing at least one acidic hydrogen atom is carboxyl group (—COOH). Where n is zero and A is —COOH, in the $-Y_nA$ moiety, such carboxyl group would be attached directly to one of the $R^3$ through $R^{11}$ positions. The Formula I compound may have one $-Y_nA$ moiety attached at one of the $R^3$ through $R^{11}$ positions, or may have a plurality of such $-Y_nA$ moieties attached at more than one of the $R^3$ through $R^{11}$ positions, up to a maximum of nine such $-Y_nA$ moieties. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the $-Y_nA$ moiety attached at one of positions $R^5$, $R^6$, $R^8$ and $R^9$ would be expected to have preferred properties, while attachment at $R^5$ or $R^9$ would be more preferred.

A preferred class of compounds within the sub-class defined by Formula I consists of those compounds wherein m is one; wherein each of $R^0$ through $R^{11}$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^0$ through $R^{11}$ may be further independently selected from amino and amido radicals of the formula

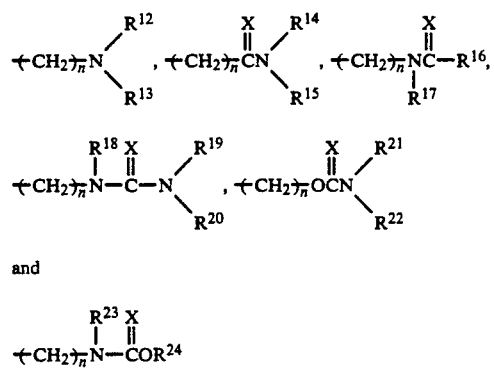

wherein X is selected from oxygen atom or sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be further independently selected from hydrido and haloalkyl, and from acidic moieties of the formula -$Y_n$A wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{24}$, Y and A groups having a substitutable position may be substituted with one or more groups selected from alkyl, alkenyl, aralkyl, hydroxyalkyl, trifluoromethyl, difluoroalkyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

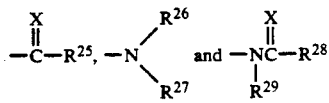

wherein X is selected from oxygen atom and sulfur atom; wherein $R^{25}$ is selected from hydrido, alkyl, cycloalkyl, cycloalkylalkyl, aralkyl, aryl, and $DR^{30}$ and

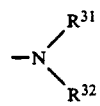

wherein D is selected from oxygen atom and sulfur atom, and $R^{30}$ is selected from hydrido, alkyl, cycloalkyl, cycloalkylalkyl, aralkyl and aryl; wherein each of $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl, and wherein each of $R^{26}$, $R^{27}$, $R^{28}$, $R^{29}$, $R^{31}$ and $R^{32}$ is further independently selected from amino and amido radicals of the formula

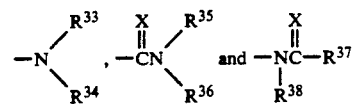

wherein X is selected from oxygen atom or sulfur atom;

wherein each of $R^{26}$ through $R^{31}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

A more preferred class of compounds within the sub-class defined by Formula I consists of those compounds wherein m is one; wherein each of $R^0$ through $R^{11}$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonylalkyl, aralkoxycarbonylalkyl, aralkylcarbonyloxyalkyl, alkylthio, cycloalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalklylcarbonylalkyl wherein each of said heteroaryl- and cycloheteroalkyl-containing groups has one or more hetero ring atoms selected from oxygen, sulfur and nitrogen atoms, and wherein each of $R^0$ through $R^{11}$ may be further independently selected from amino and amido radicals of the formula

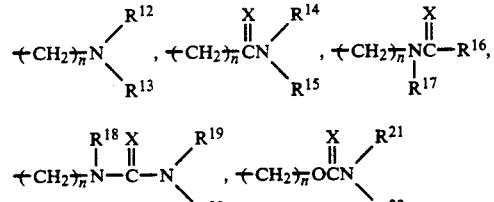

and

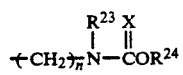

wherein X is selected from oxygen atom or sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be an acidic moiety further independently selected from hydrido and haloalkyl, and from acidic moieties of the formula -$Y_n$A wherein n is a number selected from zero through three, inclusive;

wherein A is selected from carboxylic acid and bioisosteres of carboxylic acid selected from

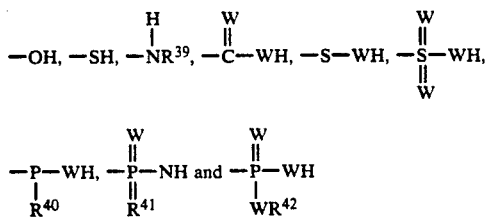

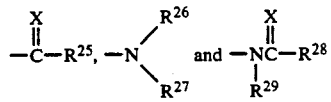

wherein each W is independently selected from oxygen atom, sulfur atom and $NR^{43}$; wherein each of $R^{39}$, $R^{40}$, $R^{41}$, $R^{42}$ and $R^{43}$ is independently selected from hydrido, alkyl, haloalkyl, haloalkylsulfonyl, haloalkylcarbonyl, cycloalkyl, cycloalkylalkyl, aryl and aralkyl; wherein each of $R^{39}$, $R^{40}$, $R^{41}$ and $R^{42}$ may be further independently selected from amino radicals of the formula

wherein each of $R^{44}$ and $R^{45}$ is independently selected from hydrido, alkyl, cycloalkyl, hydroxyalkyl, haloalkyl, cycloalkylalkyl, alkoxyalkyl, aralkyl and aryl, and wherein $R^{44}$ and $R^{45}$ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein $R^{44}$ and $R^{45}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of $R^{40}$ and $R^{41}$ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of the biphenyl moiety of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

and wherein any of the foregoing $R^1$ through $R^{24}$, Y and A groups having a substitutable position may be substituted by one or more groups selected from alkyl, difluoroalkyl, alkenyl, aralkyl, hydroxyalkyl, trifluoromethyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

wherein X is selected from oxygen atom and sulfur atom; wherein $R^{25}$ is selected from hydrido, alkyl, cycloalkyl, cycloalkylalkyl, aralkyl, aryl and $DR^{30}$ and $$-N\begin{matrix}R^{31}\\R^{32}\end{matrix}$$

wherein D is selected from oxygen atom and sulfur atom, wherein $R^{30}$ is selected from hydrido, alkyl, cycloalkyl, cycloalkylalkyl, aralkyl and aryl;

wherein each of $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

with the proviso that at least and A substituents contains a terminal primary or secondary amino moiety or a moiety convertible to a primary or secondary amino moiety;

or a tautomer thereof or a pharmaceutically-acceptable salt thereof.

An even more preferred class of compounds within the sub-class defined by Formula I consists of those compounds wherein m is one; wherein each of $R^0$, $R^1$ and $R^2$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, arylthio, aralkylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^0$ through $R^{11}$ may be further independently selected from amino and amido radicals of the formula

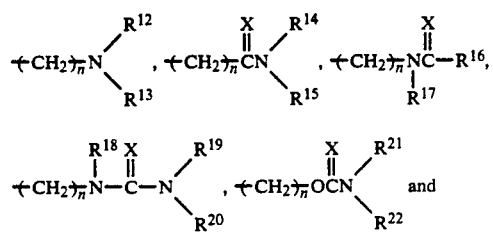

-continued

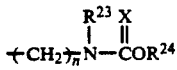

wherein X is selected from oxygen atom and sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylthio, aralkylthio, mercapto, alkylsulfinyl, alkylsulfonyl, aralkylsulfinyl, aralkylsulfonyl, arylsulfinyl, arylsulfonyl and heteroaryl having one or more ring atoms selected from oxygen, sulfur and nitrogen atoms;

and wherein each of $R^3$ through $R^{11}$ may be an acidic moiety further independently selected from acidic moieties of the formula $$-Y_nA$$

wherein n is a number selected from zero through three, inclusive; wherein A is selected from carboxylic acid and bioisosteres of carboxylic acid selected from

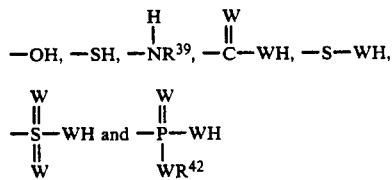

wherein each W is independently selected from oxygen atom, sulfur atom and $NR^{43}$; wherein each of $R^{39}$, $R^{42}$ and $R^{43}$ is independently selected from hydrido, alkyl, haloalkyl, haloalkylsulfonyl, haloalkylcarbonyl, cycloalkyl, cycloalkylalkyl, aryl and aralkyl; wherein each of $R^{39}$ and $R^{42}$ may be further independently selected from amino radical of the formula

wherein each of $R^{44}$ and $R^{45}$ is independently selected from hydrido, alkyl, cycloalkyl, hydroxyalkyl, haloalkyl, cycloalkylalkyl, alkoxyalkyl, aralkyl and aryl, and wherein $R^{44}$ and $R^{45}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{44}$ and $R^{45}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

wherein each of $R^1$ through $R^{24}$, Y and A independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

A highly preferred class of compounds within the sub-class defined by Formula I consists of those compounds wherein m is one; wherein each of $R^0$, $R^1$ and $R^2$ is independently selected from alkyl, hydroxyalkyl, halo, haloalkyl, cycloalkyl, cycloalkylalkyl, alkoxy, aralkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^0$ through $R^{11}$ may be further independently selected from amino and amido radicals of the formula

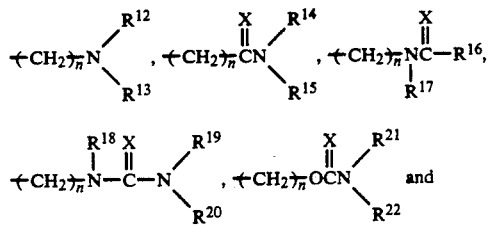

-continued

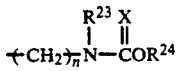

wherein X is selected from oxygen atom and sulfur atom;
wherein each n is a number independently selected from zero to six, inclusive;
wherein each of $R^{12}$ through $R^{24}$ is independently selected from hydrido, alkyl, cycloalkyl, cyano, amino, hydroxyalkyl, alkoxyalkyl, phenalkyl and phenyl;
wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio, mercapto and heteroaryl having one or more ring atoms selected from oxygen, sulfur and nitrogen atoms;
and wherein each of $R^3$ through $R^{11}$ may be an acidic moiety further independently selected from acidic moieties of the formula $-Y_nA$ wherein n is a number selected from zero through two, inclusive; wherein A is selected from carboxylic acid and bioisosteres of carboxylic acid selected from

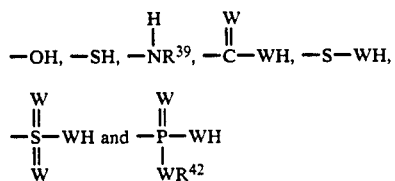

wherein each W is independently selected from oxygen atom, sulfur atom and $NR^{43}$; wherein each of $R^{39}$, $R^{42}$ and $R^{43}$ is independently selected from hydrido, alkyl, haloalkyl, haloalkylsulfonyl, haloalkylcarbonyl, cycloalkyl, phenyl and benzyl; wherein each of $R^{39}$ and $R^{42}$ may be further independently selected from amino radical of the formula

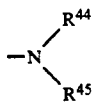

wherein each of $R^{44}$ and $R^{45}$ is independently selected from hydrido, alkyl, cycloalkyl, hydroxyalkyl, haloalkyl, alkoxyalkyl, benzyl and phenyl; and the amide, ester and salt derivatives of said acidic groups;
wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of the biphenyl moiety of Formula I; and the amide, ester and salt derivatives of said heterocyclic acidic groups;
wherein Y is a spacer group independently selected from one or more of alkyl, cycloalkyl, cycloalkylalkyl, alkenyl, phenyl, phenalkyl and aralkyl;
wherein each of $R^1$ through $R^{24}$, Y and A and independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;
with the proviso that at least one of said $R^1$ through $R^{24}$, Y and A substituents contains a terminal primary or secondary amino moiety or a moiety convertible to a primary or secondary amino moiety;
or a tautomer thereof or a pharmaceutically-acceptable salt thereof.

An even more highly preferred class of compounds within Formula I consists of those compounds wherein m is one; wherein $R^0$ is selected from alkyl, alkenyl, phenyl, alkylthio, cycloalkyl, cycloalkylalkyl and cycloalkylthio; wherein each of $R^1$ and $R^2$ is independently selected from alkyl, aminoalkyl, hydroxyalkyl, halo, haloalkyl, cycloalkyl, cycloalkylalkyl, alkoxy, aralkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, and amino and amido radicals of the formula

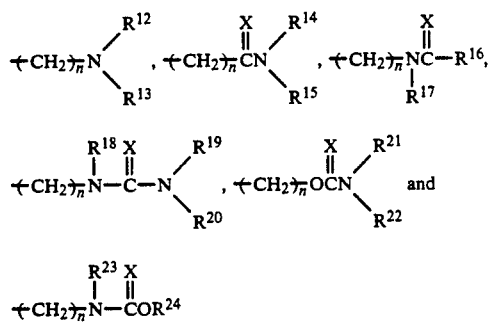

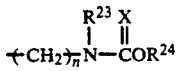

wherein X is selected from oxygen atom and sulfur atom;
wherein each n is a number independently selected from zero to six, inclusive;
wherein each of $R^{12}$ through $R^{24}$ is independently selected from hydrido, alkyl, cycloalkyl, cyano, amino, hydroxyalkyl, alkoxyalkyl, phenalkyl and phenyl;
wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, acetyl, alkoxycarbonyl, alkenyl, cyano, nitro, carboxyl, alkylthio and mercapto;
and wherein each of $R^3$ through $R^{11}$ may be an acidic moiety further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$,

CONHOC₂H₅, CONHCF₃, OH, CH₂OH, C₂H₄OH, OPO₃H₂, OSO₃H ,

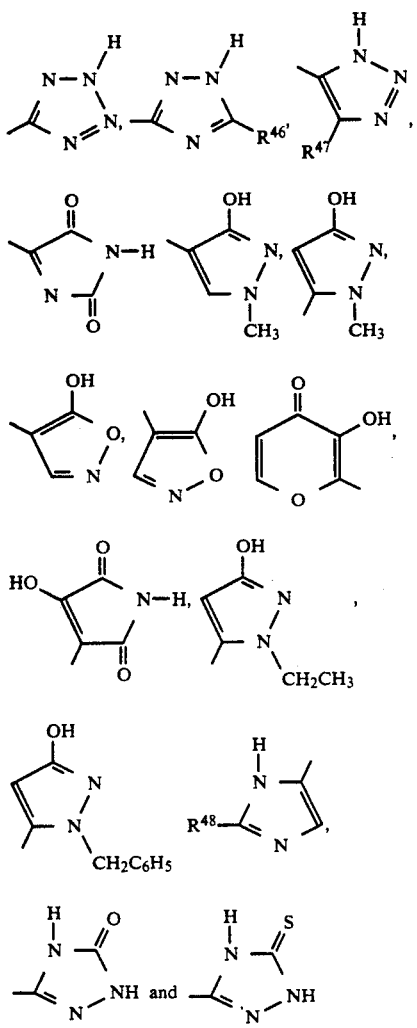

wherein each of R⁴⁶, R⁴⁷ and R⁴⁸ is independently selected from H, Cl, CN, NO₂, CF₃, C₂F₅, C₃F₇, CHF₂,CH₂F, CO₂CH₃, CO₂C₂H₅, SO₂CH₃, SO₂CF₃ and SO₂C₆F₅; wherein Z is selected from O, S, NR⁴⁹ and CH₂; wherein R⁴⁹ is selected from hydrido, CH₃ and CH₂C₆H₅; and wherein said acidic moiety may be a heterocyclic acidic group attached at any two adjacent positions of R³ through R¹¹ so as to form a fused ring system so as to include one of the phenyl rings of the biphenyl moiety of Formula I, said biphenyl fused ring system selected from

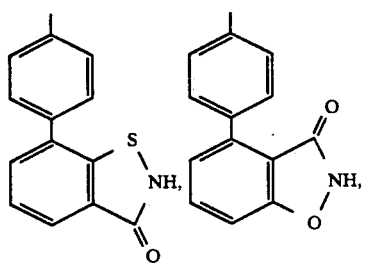

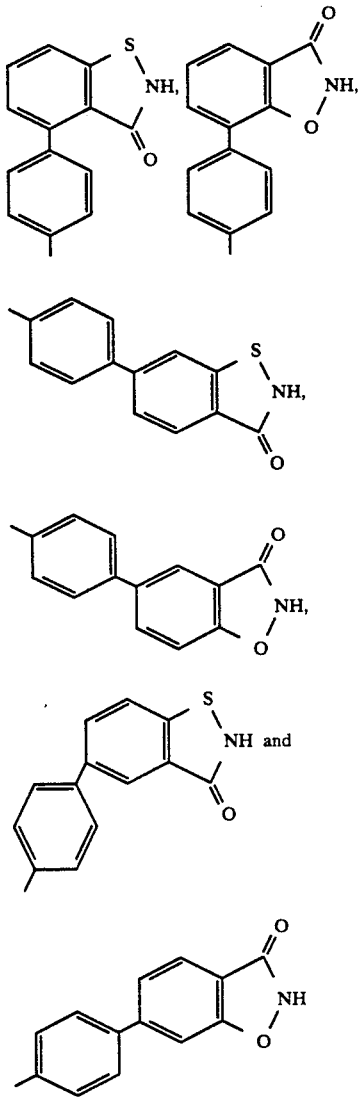

and the esters, amides and salts of said acidic moieties; with the proviso that at least one of said R¹ through R²⁴ substituents contains a terminal primary or secondary amino moiety or a moiety convertible to a primary or secondary amino moiety;

or a tautomer thereof or a pharmaceutically-acceptable salt thereof.

A class of compounds of particular interest within Formula I consists of those compounds wherein m is one; wherein R⁰ is selected from C₄H₉(n), CH₃CH₂CH=CH, C₃H₇(n), SC₃H₇,

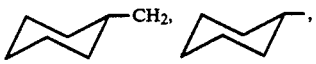

C₂H₅, C₅H₁₁(n), C₆H₁₃(n), SC₄H₉,

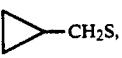

CH₃CH=CH and CH₃CH₂CH₂CH=CH—; wherein each of R¹ and R² is independently selected from amino, aminomethyl, aminoethyl, aminopropyl, CH$_2$OH, CH$_2$OCOCH$_3$, CH$_2$Cl, Cl, CH$_2$OCH$_3$, CH$_2$OCH(CH$_3$)$_2$, I, CHO, CH$_2$CO$_2$H, CH(CH$_3$)CO$_2$H, NO$_2$, Cl,

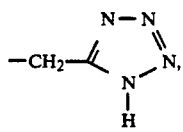

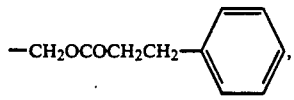

CO$_2$CH$_3$, —CONH$_2$, —CONHCH$_3$, CON(CH$_3$)$_2$, —CH$_2$—NHCO$_2$C$_2$H$_5$,

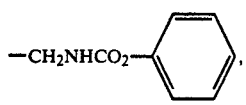

—CH$_2$NHCO$_2$CH$_3$, —CH$_2$NHCO$_2$C$_3$H$_7$, —CH$_2$NHCO$_2$CH$_2$(CH$_3$)$_2$, —CH$_2$NHCO$_2$C$_4$H$_9$, CH$_2$NHCO$_2$-adamantyl, —CH$_2$NHCO$_2$—(1-napthyl), —CH$_2$NHCONHCH$_3$, —CH$_2$NHCONHC$_2$H$_5$, —CH$_2$NHCONHC$_3$H$_7$, —CH$_2$NHCONHC$_4$H$_9$, —CH$_2$NHCONHCH(CH$_3$)$_2$, —CH$_2$NHCONH(1-napthyl), —CH$_2$NHCONH(1-adamantyl), CO$_2$H,

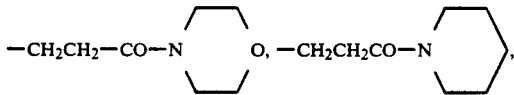

—CH$_2$CH$_2$CH$_2$CO$_2$H, —CH$_2$CH$_2$F, —CH$_2$OCONHCH$_3$, —CH$_2$OCSNHCH$_3$, —CH$_2$NHCSOC$_3$H$_7$, —CH$_2$CH$_2$CH$_2$F, —CH$_2$ONO$_2$,

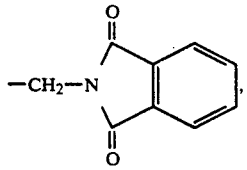

—CH$_2$SH,

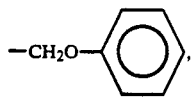

H, Cl, NO$_2$, CF$_3$, CH$_2$OH, Br, F, I, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein each of R$^3$ through R$^{11}$ is hydrido, with the proviso that at least one of R$^5$, R$^6$, R$^8$ and R$^9$ is an acidic group selected from CO$_2$H, SH, PO$_3$H$_2$, SO$_3$H, CONHNH$_2$, CONHNHSO$_2$CF$_3$, OH,

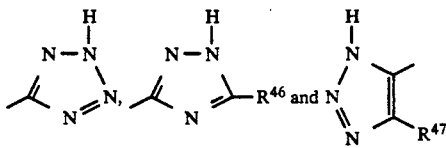

wherein each of R$^{46}$ and R$^{47}$ is independently selected from Cl, CN, NO$_2$, CF$_3$, CO$_2$CH$_3$ and SO$_2$CF$_3$;

with the proviso that at least one of said R$^1$ through R$^{11}$ substituents contains a terminal primary or secondary amino moiety or a moiety convertible to a primary or secondary amino moiety;

or a tautomer thereof or a pharmaceutically-acceptable salt thereof.

A class of compounds of more particular interest within Formula I consists of these compounds wherein m is one; wherein R$^0$ is selected from C$_4$H$_9$(n), CH$_3$CH$_2$CH=CH, C$_3$H$_7$(n), SC$_3$H$_7$,

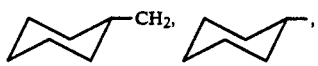

C$_2$H$_5$, C$_5$H$_{11}$(n), C$_6$H$_{13}$(n), SC$_4$H$_9$,

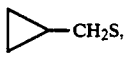

CH$_3$CH=CH and CH$_3$CH$_2$CH$_2$CH=CH—; wherein R$^1$ is selected from amino, aminomethyl, aminoethyl, aminopropyl, CH$_2$OH, CH$_2$OCOCH$_3$, CH$_2$Cl, Cl, CH$_2$OCH$_3$, CH$_2$OCH(CH$_3$)$_2$, I, CHO, CH$_2$CO$_2$H, CH(CH$_3$)CO$_2$H, —CO$_2$CH$_3$, CONH$_2$, —CONHCH$_3$, CON(CH$_3$)$_2$, CH$_2$—NHCO$_2$C$_2$H$_5$,

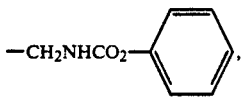

—CH$_2$NHCO$_2$CH$_3$, —CH$_2$NHCO$_2$C$_3$H$_7$, —CH$_2$NHCO$_2$CH(CH$_3$)$_2$, —CH$_2$NHCO$_2$C$_4$H$_9$, CH$_2$NHCO$_2$-adamantyl, —CH$_2$NHCO$_2$-(1-napthyl), —CH$_2$NHCONHCH$_3$, —CH$_2$NHCONHC$_2$H$_5$, —CH$_2$NHCONHC$_3$H$_7$, —CH$_2$NHCONHC$_4$H$_9$, —CH$_2$NHCONHCH(CH$_3$)$_2$, —CH$_2$NHCONH(1-napthyl), —CH$_2$NHCONH(1-adamantyl), CO$_2$H,

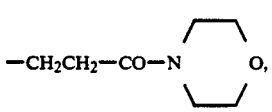

—CH$_2$CH$_2$CH$_2$CO$_2$H, —CH$_2$CH$_2$F, CH$_2$OCONHCH$_3$, —CH$_2$CH$_2$CH$_2$F, —CH$_2$SH and

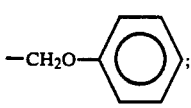

wherein $R^2$ is selected from H, Cl, $NO_2$, $CF_3$, $CH_2OH$, Br, F, I, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein each of $R^3$ through $R^{11}$ is hydrido, with the proviso that at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH,

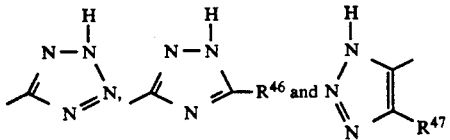

wherein each of $R^{46}$ and $R^{47}$ is independently selected from Cl, CN, $NO_2$, $CF_3$, $CO_2CH_3$ and $SO_2CF_3$;

with the proviso that at least one of said $R^1$ through substituents contains a terminal primary or secondary amino moiety or a moiety convertible to a primary or secondary amino moiety;

or a tautomer thereof or a pharmaceutically-acceptable salt thereof.

A class of compounds of even more particular interest within Formula I consists of those compounds wherein m is one wherein $R^0$ is selected from $C_4H_9(n)$, $CH_3CH_2CH=CH$, $C_3H_7(N)$, $SC_3H_7$,

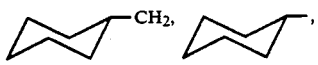

$C_2H_5$, $C_5H_{11}(n)$, $C_6H_{13}(n)$, $SC_4H_9$,

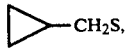

$CH_3CH=CH$ and $CH_3CH_2CH_2CH=CH-$; wherein $R^1$ is selected from H, Cl, $NO_2$, $CF_3$, $CH_2OH$, Br, F, I, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein $R^2$ is selected from amino, aminomethyl, aminoethyl, aminopropyl, $CH_2OH$, $CH_2OCOCH_3$, $CH_2Cl$, Cl, $CH_2OCH_3$, $CH_2OCH(CH_3)_2$, I, CHO, $CH_2CO_2H$, $CH(CH_3)CO_2H$, , $-CO_2CH_3$, $-CONH_2$, $-CONHCH_3$, $CON(CH_3)_2$, $-CH_2-NHCO_2C_2H_5$,

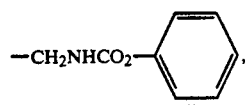

$-CH_2NHCO_2CH_3$, $-CH_2NHCO_2C_3H_7$, $-CH_2NHCO_2CH_2(CH_3)_2$, $-CH_2NHCO_2C_4H_9$, $CH_2NHCO_2$-adamantyl, $-CH_2NHCO_2$-(1-napthyl), $-CH_2NHCONHCH_3$, $-CH_2NHCONHC_2H_5$, $-CH_2NH-$ $CONHC_3H_7$, $-CH_2NHCONHC_4H_9$, $-CH_2NHCONHCH(CH_3)_2$, $-CH_2NHCONH(1-napthyl)$, $-CH_2NHCONH(1-adamantyl)$, $CO_2H$,

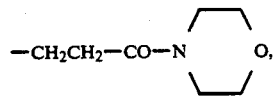

$-CH_2CH_2CH_2CO_2H$, $-CH_2CH_2F$, $-CH_2OCONHCH_3$, $-CH_2CH_2CH_2F$, $-CH_2SH$ and

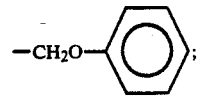

wherein each of $R^3$ through $R^{11}$ is hydrido, with the proviso that at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH,

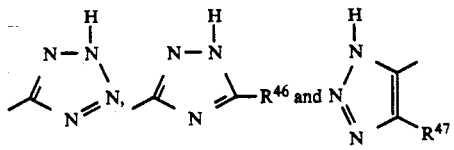

wherein each of $R^{46}$ and $R^{47}$ is independently selected from Cl, CN, $NO_2$, $CF_3$, $CO_2CH_3$ and $SO_2CF_3$;

with the proviso that at least one of said $R^1$ through $R^{11}$ substituents contains a terminal primary or secondary amino moiety or a moiety convertible to a primary or secondary amino moiety;

or a tautomer thereof or a pharmaceutically-acceptable salt thereof.

The second component of a conjugate of the invention is provided by a residue which forms a kidney-enzyme-cleavable amide bond with the residue of the first-component AII antagonist compound. Such residue is preferably selected from a class of compounds of Formula II:

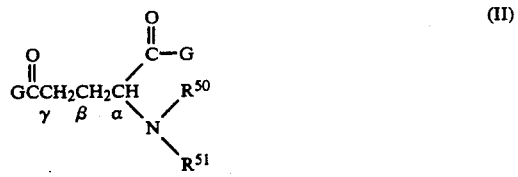

(II)

wherein each of $R^{50}$ and $R^{51}$ may be independently selected from hydrido, alkylcarbonyl, alkoxycarbonyl, alkoxyalkyl, hydroxyalkyl and haloalkyl; and wherein G is selected from hydroxyl, halo, mercapto, $-OR^{52}$, $-SR^{53}$ and

wherein each of $R^{52}$, $R^{53}$ and $R^{54}$ is independently selected from hydrido and alkyl; with the proviso that said Formula II compound is selected such that formation of the cleavable amide bond occurs at carbonyl moiety attached at the gamma-position carbon of said Formula II compound.

More preferred are compounds of Formula II wherein each G is hydroxy.

A more highly preferred class of compounds within Formula II consists of those compounds wherein each G is hydroxy; wherein $R^{50}$ is hydrido; and wherein $R^{51}$ is selected

wherein $R^{55}$ is selected from methyl, ethyl, n-propyl, isopropyl, n-butyl, sec-butyl, iso-butyl, tert-butyl, n-pentyl, neopentyl, n-hexyl and chloromethyl.

A most highly preferred compound of Formula II is N-acetyl-γ-glutamic acid which provides a residue for the second component of a conjugate of the invention as shown below:

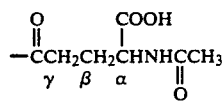

The phrase "terminal primary or secondary amino moiety or a moiety convertible to a primary or secondary amino terminal moiety" characterizes a structural requirement for selection of a suitable angiotensin II antagonist compound as the "active" first residue of a conjugate of the invention. Such terminal amino moiety must be available to react with a terminal carboxylic moiety of the cleavable second residue to form a kidney-enzyme-specific hydrolyzable bond.

In one embodiment of the invention, the first component used to form a conjugate of the invention provides a first residue derived from an AII antagonist compound containing a terminal primary or secondary amino moiety. Examples of such terminal amino moiety are amino and linear or branched aminoalkyl moieties containing linear or branched alkyl groups such as aminomethyl, aminoethyl, aminopropyl, aminoisopropyl, aminobutyl, aminosecbutyl, aminoisobutyl, aminotertbutyl, aminopentyl, aminoisopentyl and aminoneopentyl.

In another embodiment of the invention, the first component used to form the conjugate of the invention provides a first residue derived from an AII antagonist compound containing a moiety convertible to a primary or secondary amino terminal moiety. An example of a moiety convertible to an amino terminal moiety is a carboxylic acid group reacted with hydrazine so as to convert the acid moiety to carboxylic acid hydrazide. The hydrazide moiety thus contains the terminal amino moiety which may then be further reacted with the carboxylic acid containing residue of the second component to form a hydrolyzable amide bond. Such hydrazide moiety thus constitutes a "linker" group between the first and second components of a conjugate of the invention.

Suitable linker groups may be provided by a class of diamino-terminated linker groups based on hydrazine as defined by Formula III:

wherein each of $R^{200}$ and $R^{201}$ may be independently selected from hydrido, alkyl, cycloalkyl, cycloalkylalkyl, alkoxyalkyl, hydroxyalkyl, aralkyl, aryl, haloalkyl, amino, monoalkylamino, dialkylamino, cyanoamino, carboxyalkyl, alkylsulfino, alkylsulfonyl, arylsulfinyl and arylsulfonyl; and wherein n is zero or a number selected from three through seven, inclusive. In Table I there is shown a class of specific examples of diamino-terminated linker groups within Formula III, identified as Linker Nos. 1-73. These linker groups would be suitable to form a conjugate between a carbonyl moiety of an AII antagonist (designated as "I") and a carbonyl moiety of a carbonyl terminated second residue such as the carbonyl moiety attached to the gamma carbon of a glutamyl residue (designated as "T").

TABLE I $$I-N-(CH_2)_{\overline{n}}-N-T$$
$$\phantom{I-N-(CH_2)_n-}|\phantom{-(CH_2)_n-}|$$
$$\phantom{I-N-(CH_2)_n-}R^{200}\phantom{-}R^{201}$$

I = inhibitor
T = acetyl-γ-glutamyl

| LINKER NO. | n | $R^{200}$ | $R^{201}$ |
|---|---|---|---|
| 1 | 0 | H | H |
| 2 | 0 | CH₃ | H |
| 3 | 0 | C₂H₅ | H |
| 4 | 0 | C₃H₇ | H |
| 5 | 0 | CH(CH₃)₂ | H |
| 6 | 0 | C₄H₉ | H |
| 7 | 0 | CH(CH₃)CH₂CH₃ | H |
| 8 | 0 | C(CH₃)₃ | H |
| 9 | 0 | C₅H₉ | H |
| 10 | 0 | C₆H₁₁(cyclo) | H |
| 11 | 0 | C₆H₅ | H |
| 12 | 0 | CH₂C₆H₅ | H |
| 13 | 0 | H | CH₃ |
| 14 | 0 | H | C₂H₅ |
| 15 | 0 | H | C₃H₇ |
| 16 | 0 | H | CH(CH₃)₂ |
| 17 | 0 | H | C₄H₉ |
| 18 | 0 | H | CH(CH₃)CH₂CH₃ |
| 19 | 0 | H | C(CH₃)₃ |
| 20 | 0 | H | C₅H₉ |
| 21 | 0 | H | C₆H₁₃ |
| 22 | 0 | H | C₆H₅ |
| 23 | 0 | H | CH₂C₆H₅ |
| 24 | 0 | H | C₆H₁₁(cyclo) |
| 25 | 0 | C₆H₁₃ | H |
| 26 | 0 | CH₃ | CH₃ |
| 27 | 0 | C₂H₅ | C₂H₅ |
| 28 | 0 | C₃H₇ | C₃H₇ |
| 29 | 0 | CH(CH₃)₂ | CH(CH₃)₂ |
| 30 | 0 | C₄H₉ | C₄H₉ |
| 31 | 0 | CH(CH₃)CH₂CH₃ | CH(CH₃)CH₂CH₃ |
| 32 | 0 | C(CH₃)₃ | C(CH₃)₃ |
| 33 | 0 | C₅H₉ | C₅H₉ |
| 34 | 0 | C₆H₁₃ | C₆H₁₃ |
| 35 | 0 | C₆H₁₁(cyclo) | C₆H₁₁(cyclo) |
| 36 | 0 | C₆H₅ | C₆H₅ |
| 37 | 0 | CH₂C₆H₅ | CH₂C₆H₅ |
| 38 | 3 | H | H |
| 39 | 3 | CH₃ | H |
| 40 | 3 | H | CH₃ |
| 41 | 3 | C₆H₅ | H |
| 42 | 3 | H | C₆H₅ |
| 43 | 3 | CH₃ | C₆H₅ |
| 44 | 3 | C₆H₅ | CH₃ |
| 45 | 3 | CH₂C₆H₅ | H |
| 46 | 3 | H | CH₂C₆H₅ |
| 47 | 4 | H | H |
| 48 | 4 | CH₃ | H |
| 49 | 4 | H | CH₃ |

TABLE I-continued

I—N—(CH$_2$)$_{\overline{n}}$—N—T
        |              |
        R$^{200}$     R$^{201}$ I = inhibitor
T = acetyl-γ-glutamyl

| LINKER NO. | n | R$^{200}$ | R$^{201}$ |
|---|---|---|---|
| 50 | 4 | C$_6$H$_5$ | H |
| 51 | 4 | H | C$_6$H$_5$ |
| 52 | 4 | CH$_3$ | C$_6$H$_5$ |
| 53 | 4 | C$_6$H$_5$ | CH$_3$ |
| 54 | 4 | CH$_2$C$_6$H$_5$ | H |
| 55 | 4 | H | CH$_2$C$_6$H$_5$ |
| 56 | 5 | H | H |
| 57 | 5 | CH$_3$ | H |
| 58 | 5 | H | CH$_3$ |
| 59 | 5 | C$_6$H$_5$ | H |
| 60 | 5 | H | C$_6$H$_5$ |
| 61 | 5 | CH$_3$ | C$_6$H$_5$ |
| 62 | 5 | C$_6$H$_5$ | CH$_3$ |
| 63 | 5 | CH$_2$C$_6$H$_5$ | H |
| 64 | 5 | H | CH$_2$C$_6$H$_5$ |
| 65 | 6 | H | H |
| 66 | 6 | CH$_3$ | H |
| 67 | 6 | H | CH$_3$ |
| 68 | 6 | C$_6$H$_5$ | H |
| 69 | 6 | H | C$_6$H$_5$ |
| 70 | 6 | CH$_3$ | C$_6$H$_5$ |
| 71 | 6 | C$_6$H$_5$ | CH$_3$ |
| 72 | 6 | CH$_2$C$_6$H$_5$ | H |
| 73 | 6 | H | CH$_2$C$_6$H$_5$ |

Another class of suitable diamino terminal linker groups is defined by Formula IV:

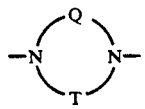

(IV)

wherein each of Q and T is one or more groups independently selected from

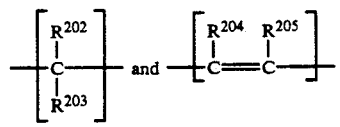

wherein each of R$^{202}$ through R$^{205}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl, alkanoyl, alkenyl, cycloalkenyl and alkynyl.

A preferred class of linker groups within Formula IV is defined by Formula V:

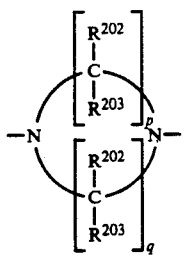

(V)

wherein each of R$^{202}$ and R$^{203}$ is independently selected from hydrido, hydroxy, alkyl, phenalkyl, phenyl, alkoxy, benzyloxy, phenoxy, alkoxyalkyl, hydroxyalkyl, halo, amino, monoalkylamino, dialkylamino, carboxy, carboxyalkyl and alkanoyl; and wherein each of p and q is a number independently selected from one through six, inclusive; with the proviso that when each of R$^{202}$ and R$^{203}$ is selected from halo, hydroxy, amino, monoalkylamino and dialkylamino, then the carbon to which R$^{202}$ or R$^{203}$ is attached in Formula V is not adjacent to a nitrogen atom of Formula V.

A more preferred class of linker groups of Formula V consists of divalent radicals wherein each of R$^{202}$ and R$^{203}$ is independently selected from hydrido, hydroxy, alkyl, alkoxy, amino, monoalkylamino, carboxy, carboxyalkyl and alkanoyl; and wherein each of p and q is a number independently selected from two through four, inclusive. Even more preferred are linker groups wherein each of R$^{202}$ and R$^{203}$ is independently selected from hydrido, amino, monoalkylamino and carboxyl; and wherein each of p and q is independently selected from the numbers two and three. Most preferred is a linker group wherein each of R$^{202}$ and R$^{203}$ is hydrido; and wherein each of p and q is two; such most preferred linker group is derived from a piperazinyl group and has the structure

In Table II there is shown a class of specific examples of cyclized, diamino-terminated linker groups within Formula V. These linker groups, identified as Linker Nos. 74–95, would be suitable to form a conjugate between a carbonyl moiety of an AII antagonist (designated as "I") and a carbonyl moiety of carbonyl terminated second residue such as the carbonyl moiety attached to the gamma carbon of a glutamyl residue (designated as "T").

TABLE II

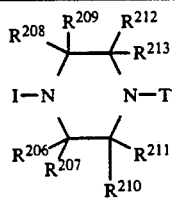

I = inhibitor
T = acetyl-γ-glutamyl

| LINKER NO. | $R^{206}$ | $R^{207}$ | $R^{208}$ | $R^{209}$ | $R^{210}$ | $R^{211}$ | $R^{212}$ | $R^{213}$ |
|---|---|---|---|---|---|---|---|---|
| 74 | H | H | H | H | H | H | H | H |
| 75 | $CH_3$ | H | H | H | H | H | H | H |
| 76 | H | H | H | H | $CH_3$ | H | H | H |
| 77 | $CH_3$ | H | H | H | $CH_3$ | H | H | H |
| 78 | $CH_3$ | H | $CH_3$ | H | H | H | H | H |
| 79 | $CH_3$ | H | H | H | H | H | $CH_3$ | H |
| 80 | $CH_3$ | $CH_3$ | H | H | H | H | H | H |
| 81 | H | H | H | H | $CH_3$ | $CH_3$ | H | H |
| 82 | $CH_3$ | $CH_3$ | H | H | $CH_3$ | $CH_3$ | H | H |
| 83 | $CH_3$ | $CH_3$ | $CH_3$ | $CH_3$ | H | H | H | H |
| 84 | $CH_3$ | $CH_3$ | H | H | H | H | $CH_3$ | $CH_3$ |
| 85 | H | H | H | H | $CH_3$ | $CH_3$ | $CH_3$ | $CH_3$ |
| 86 | $C_6H_5$ | H | H | H | H | H | H | H |
| 87 | H | H | H | H | $C_6H_5$ | H | H | H |
| 88 | $C_6H_5$ | H | H | H | $C_6H_5$ | H | H | H |
| 89 | $C_6H_5$ | H | H | H | H | H | $C_6H_5$ | H |
| 90 | $C_6H_5$ | H | $C_6H_5$ | H | H | H | H | H |
| 91 | $CH_2C_6H_5$ | H | H | H | H | H | H | H |
| 92 | H | H | H | H | $CH_2C_6H_5$ | H | H | H |
| 93 | $CH_2C_6H_5$ | H | H | H | $CH_2C_6H_5$ | H | H | H |
| 94 | $CH_2C_6H_5$ | H | H | H | H | H | $CH_2C_6H_5$ | H |
| 95 | $CH_2C_6H_5$ | H | $CH_2C_6H_5$ | H | H | H | H | H |

Another class of suitable diamino terminal linker groups is defined by Formula VI:

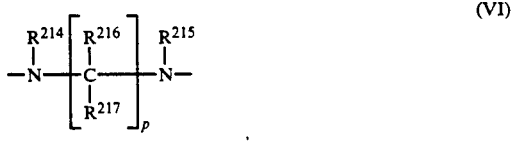

wherein each of $R^{214}$ through $R^{217}$ is independently selected from hydrido, alkyl, cycloalkyl, cycloalkylalkyl, hydroxyalkyl, alkoxyalkyl, aralkyl, aryl, haloalkyl, amino, monoalkylamino, dialkylamino, cyanoamino, carboxyalkyl, alkylsulfino, alkylsulfonyl, arylsulfinyl and arylsulfonyl; and wherein p is a number selected from one through six inclusive.

A preferred class of linker groups within Formula VI consists of divalent radicals wherein each of $R^{214}$ and $R^{215}$ is hydrido; wherein each of $R^{62}$ and $R^{63}$ is independently selected from hydrido, alkyl, phenalkyl, phenyl, alkoxyalkyl, hydroxyalkyl, haloalkyl and carboxyalkyl; and wherein p is two or three. A more preferred class of linker groups within Formula VI consists of divalent radicals wherein each of $R^{214}$ and $R^{215}$ is hydrido; wherein each of $R^{216}$ and $R^{217}$ is independently selected from hydrido and alkyl; and wherein p is two. A specific example of a more preferred linker within Formula VI is the divalent radical ethylenediamino. In Table III there is shown a class of specific examples of diamino-terminated linker groups within Formula VI. These linker groups, identified as Linker Nos. 96-134, would be suitable to form a conjugate between a carbonyl moiety of an AII antagonist (designated as "I") and a carbonyl moiety of carbonyl terminated second residue such as the carbonyl moiety attached to the gamma carbon of a glutamyl residue (designated as "T").

TABLE III

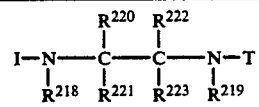

I = inhibitor
G = acetyl-γ-glutamyl

| LINKER NO. | $R^{218}$ | $R^{219}$ | $R^{220}$ | $R^{221}$ | $R^{222}$ | $R^{223}$ |
|---|---|---|---|---|---|---|
| 96 | H | H | H | H | H | H |
| 97 | H | H | H | H | H | $CH_3$ |
| 98 | H | H | H | $CH_3$ | H | H |
| 99 | H | H | H | $CH_3$ | H | $CH_3$ |
| 100 | $CH_3$ | H | H | H | H | H |
| 101 | H | $CH_3$ | H | H | H | H |
| 102 | H | H | H | H | $CH_3$ | $CH_3$ |
| 103 | H | H | $CH_3$ | $CH_3$ | H | H |

TABLE III-continued

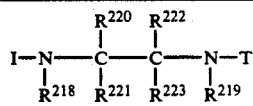

I = inhibitor
G = acetyl-γ-glutamyl

| LINKER NO. | $R^{218}$ | $R^{219}$ | $R^{220}$ | $R^{221}$ | $R^{222}$ | $R^{223}$ |
|---|---|---|---|---|---|---|
| 104 | CH$_3$ | CH$_3$ | H | H | H | H |
| 105 | H | H | H | H | H | C$_6$H$_5$ |
| 106 | H | H | H | C$_6$H$_5$ | H | H |
| 107 | H | H | H | C$_6$H$_5$ | H | C$_6$H$_5$ |
| 108 | C$_6$H$_5$ | H | H | H | H | H |
| 109 | H | C$_6$H$_5$ | H | H | H | H |
| 110 | H | H | H | H | C$_6$H$_5$ | C$_6$H$_5$ |
| 111 | H | H | C$_6$H$_5$ | C$_6$H$_5$ | H | H |
| 112 | C$_6$H$_5$ | C$_6$H$_5$ | H | H | H | H |
| 113 | H | H | H | H | H | C$_2$H$_5$ |
| 114 | H | H | H | C$_2$H$_5$ | H | H |
| 115 | H | H | H | C$_2$H$_5$ | H | C$_2$H$_5$ |
| 116 | C$_2$H$_5$ | H | H | H | H | H |
| 117 | H | C$_2$H$_5$ | H | H | H | H |
| 118 | H | H | H | H | C$_2$H$_5$ | C$_2$H$_5$ |
| 119 | H | H | C$_2$H$_5$ | C$_2$H$_5$ | H | H |
| 120 | C$_2$H$_5$ | C$_2$H$_5$ | H | H | H | H |
| 121 | CH$_3$ | H | C$_6$H$_5$ | H | H | H |
| 122 | CH$_3$ | H | H | H | C$_6$H$_5$ | H |
| 123 | H | CH$_3$ | C$_6$H$_5$ | H | H | H |
| 124 | H | CH$_3$ | H | H | C$_6$H$_5$ | H |
| 125 | CH$_3$ | CH$_3$ | H | C$_6$H$_5$ | H | H |
| 126 | CH$_3$ | CH$_3$ | H | H | H | C$_6$H$_5$ |
| 127 | H | H | H | H | H | CH$_2$C$_6$H$_5$ |
| 128 | H | H | H | CH$_2$C$_6$H$_5$ | H | H |
| 129 | CH$_2$C$_6$H$_5$ | H | H | H | H | H |
| 130 | H | CH$_2$C$_6$H$_5$ | H | H | H | H |
| 131 | CH$_3$ | H | CH$_2$C$_6$H$_5$ | H | H | H |
| 132 | CH$_3$ | H | H | H | CH$_2$C$_6$H$_5$ | H |
| 133 | H | CH$_3$ | CH$_2$C$_6$H$_5$ | H | H | H |
| 134 | H | CH$_3$ | H | H | CH$_2$C$_6$H$_5$ | H |

The term "hydrido" denotes a single hydrogen atom (H) which may be attached, for example, to a carbon atom to form a hydrocarbyl group or attached to an oxygen atom to form an hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atomms. The term "cycloalkyl" embraces cyclic radicals having three to about ten ring carbon atoms, preferably three to about six carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. Preferably, when the difluoroalkyl group is attached at the triazole ring $R^1$ and $R^2$ positions of Formula I, the two fluoro atoms are substituted on the carbon atom which is attached directly to the triazole ring. Such preferred difluoroalkyl group may be characterized as an "alpha-carbon difluoro-substituted difluoroalkyl group". The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality or unsaturated bonds, with such plurality of bonds either adjacent, such as allene-type structures, or in conjugation, or separated by several saturated carbons.

Conjugates of the invention formed from compounds of Formula I have been found to inhibit the action of angiotensin II in mammals. For example, specific biphenylmethyl 1H-substituted-imidazole compounds within Formula I have been evaluated for angiotensin II receptor binding and antihypertensive effects in renal hypertensive rats, as shown in EP #253,310 published Jan. 20, 1988. Thus, conjugates of Formula I are therapeutically useful in methods for treating hypertension by administering to a hypertensive patient a therapeutically-effective amount of a conjugate containing a compound of Formula I, such that the conjugate is hydrolyzed by an enzyme found predominantly in the kidney so as to release an active angiotensin II antagonist species. The phrase "hypertensive patient" means, in this context, a mammalian subject suffering from the effects of hypertension or susceptible to a hypertensive condition if not treated to prevent or control such hypertension.

Included within the invention are conjugates of compounds of Formula I which are tautomeric forms of the described compounds, isomeric forms including diastereoisomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, suffuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, $\beta$-hydroxy butyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I. Also, such pharmaceutical salts may be formed with either a compound of Formula I which is contained in the conjugate, or such salts may be formed with the conjugate itself.

Conjugates of the invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting conjugates with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active conjugates can likewise be obtained by utilizing optically active starting materials. These isomers may be in the form of a free acid, a free base, an ester or a salt.

Conjugates of the invention may be prepared using precursors of highly active angiotensin II antagonists of Formula I. Examples of lesser active, suitable precursors are acid chloride, esters and amides of angiotensin II antagonists of Formula I. For example, ester precursors of angiotensin II antagonists, such as the methyl ester precursor made in Step 1 of Example 81, may be reacted with hydrazine to provide an amino terminal moiety which then can be reacted with a glutamic acid derivative to form a conjugate of the invention. Such precursors or intermediates themselves may be relatively strong, relatively weak, or inactive as AII antagonists. Also, conjugates of the invention may be prepared using angiotensin II antagonists lacking a reactive terminal amino moiety. Such angiotensin II antagonists, as shown in Example Nos. 78-80 of Table IV, lack a terminal amino moiety. These AII antagonist compounds may be modified as described in Example Nos. 711 and 712 to contain a terminal acid moiety which then may be connected to a glutamyl residue through a diamino-terminated linker group, such as shown in Tables I-III.

Synthetic Procedures

Conjugates of the invention are synthesized by reaction between precursors of the first and second residues. One of such precursors must contain a reactive acid moiety, and the other precursor must contain a reactive amino moiety, so that a conjugate is formed having a cleavable bond. Either precursor of the first and second residues may contain such reactive acid or amino moieties. Preferably, the precursors of the first residue are angiotensin II antagonists and will contain a reactive amino moiety or a moiety convertible to a reactive amino moiety. Inhibitor compounds lacking a reactive amino moiety may be chemically modified to provide such reactive amino moiety. Chemical modification of these inhibitor compounds lacking a reactive amino group may be accomplished by reacting an acid or an ester group on an AII antagonist compound with an amino compound having at least one reactive amino moiety. A suitable amino compound would be a diamino compound such as hydrazine, urea or ethylenediamine. Hydrazine, for example, may be reacted with a carboxylic acid or ester moiety of an AII antagonist compound to form a hydrazide derivative of such AII antagonist compound.

In the following general Synthetic Procedures, there is described firstly in Scheme I, methods for making suitable angiotensin II antagonists of Formula I for selection as the first component of the conjugate. Then, in Schemes II-VII, there are described general methods for making a conjugate by reacting a first component AII antagonist of Formula I with a cleavable second component represented by N-acetyl-$\gamma$-glutamic acid.

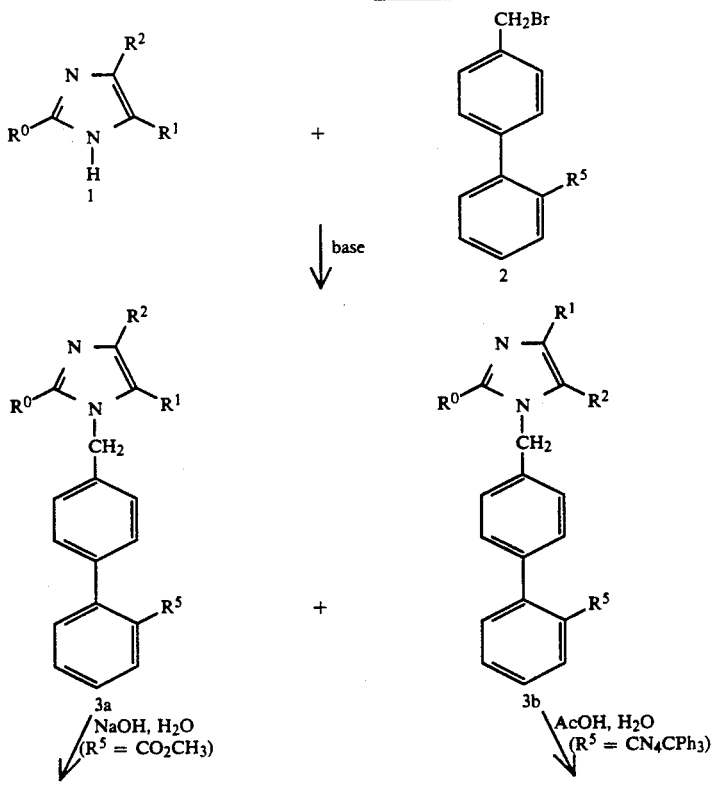

Scheme I

-continued
Scheme I

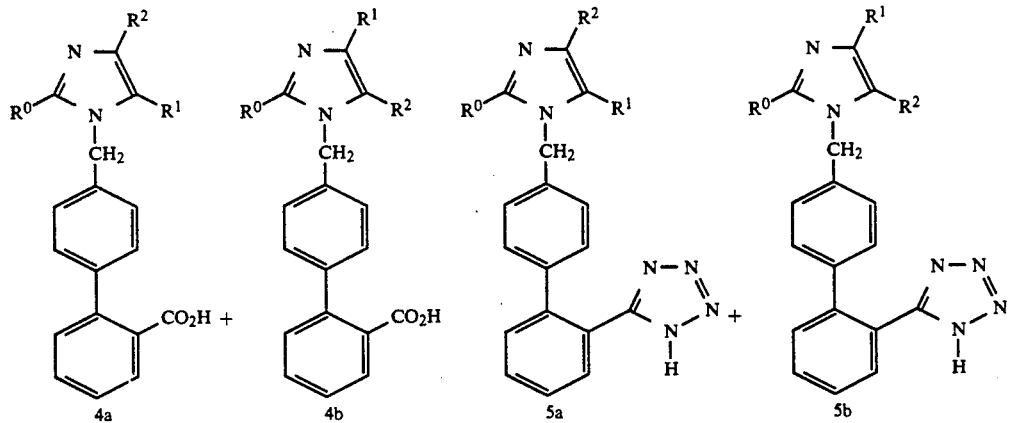

Synthetic Scheme I shows the coupling reaction of trisubstituted imidazoles 1 with the appropriate alkylating reagent 2. In the first step, 1 and 2 are reacted in dimethylformaide (DMF) in the presence of base, such as cesium carbonate, and a dehydrating agent, such as molecular seives, to give a mixture of coupled regioisomers 3a and 3b. The isomer mixture may be converted to mixtures of the corresponding acids 4a and 4b or tetrazoles 5a and 5b. Or, the isomers 3a and 3b may be separated by chromatographic methods, and each isomer may be reacted with the appropriate reagent to provide the acid- or tetrazole-substituted end product.

Scheme II

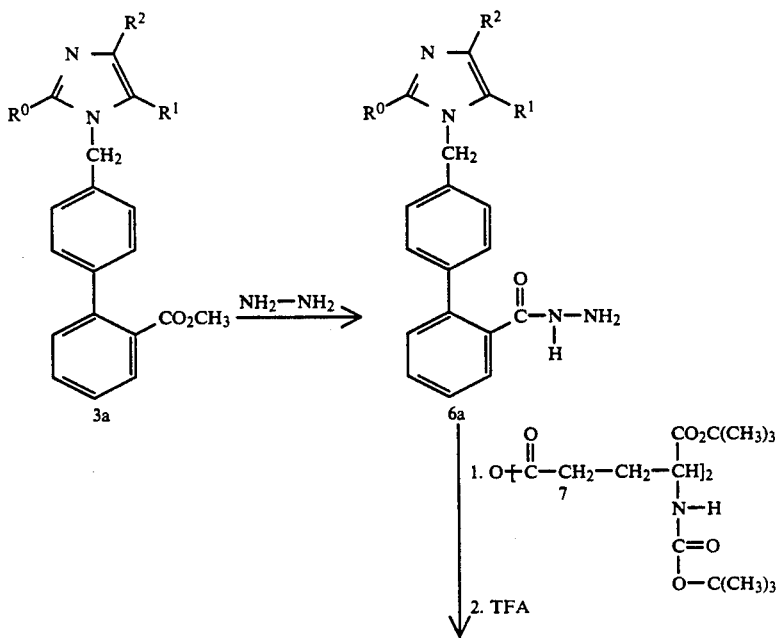

-continued
Scheme II

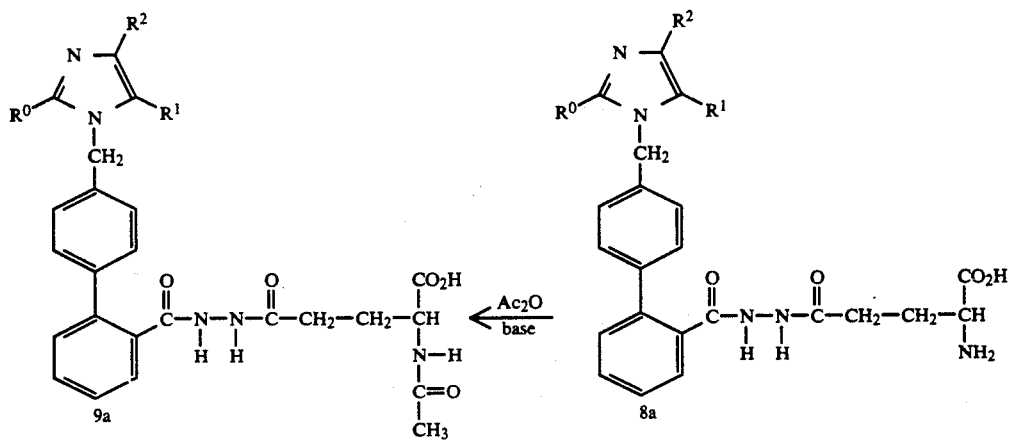

Synthetic Scheme II shows the preparation of the renal-selective angiotensin II antagonists by coupling γ-glutamic acid with one of the angiotensin II antagonist regiosiomers 3a (the synthesis of the other regioisomer is shown in Scheme III); the biphenyl $R^5$ acid moiety of the AII antagonist is coupled to the γ-acid moiety of glutamic acid via an hydrazine linker. In step 1, the methyl ester of the AII antagonist 3a is converted to the hydrazide 6a by the action of hydrazine. In step 2, the hydrazide 6a is first reacted with the symmetrical anhydride of the protected γ-glutamic acid 7 and subsequently reacted with trifluoroacetic acid (TFA) to give the deprotected coupled material 8a. In Step 3, the free amino group of 8a is acetylated with acetic anhydride in the presence of base to give the renal-selective angiotensin II antagonist 9a.

Scheme III

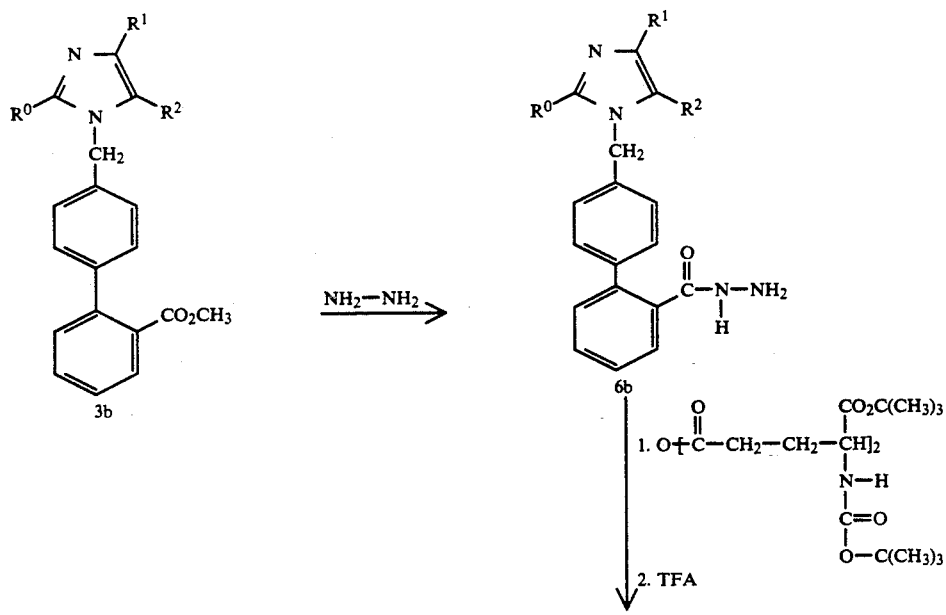

-continued
Scheme III

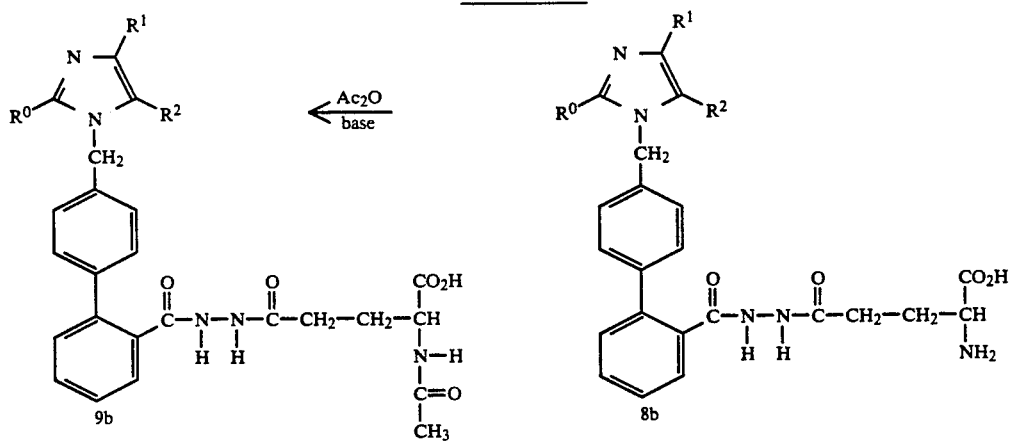

Synthetic Scheme III shows the preparation of renal-selective angiotensin II antagonists by coupling γ-glutamic acid with one of the angiotensin II antagonist regioisomers 3b (the synthesis of the other regioisomer is shown in Scheme II); the biphenyl R⁵ acid moiety of the AII antagonist is coupled to the γ-acid moiety of glutamic acid via an hydrazine linker. In step 1, the methyl ester of the AII antagonist 3b is converted to the hydrazide 6b by the action of hydrazine. In step 2, the hydrazide 6b is first reacted with the symmetrical anhydride of the protected γ-glutamic acid 7 and subsequently reacted with TFA to give the deprotected coupled material 8b. In step 3, the free amino group of 8b is acetylated with acetic anhydride in the presence of base to give the renal-selective angiotensin II antagonist 9b.

Scheme IV

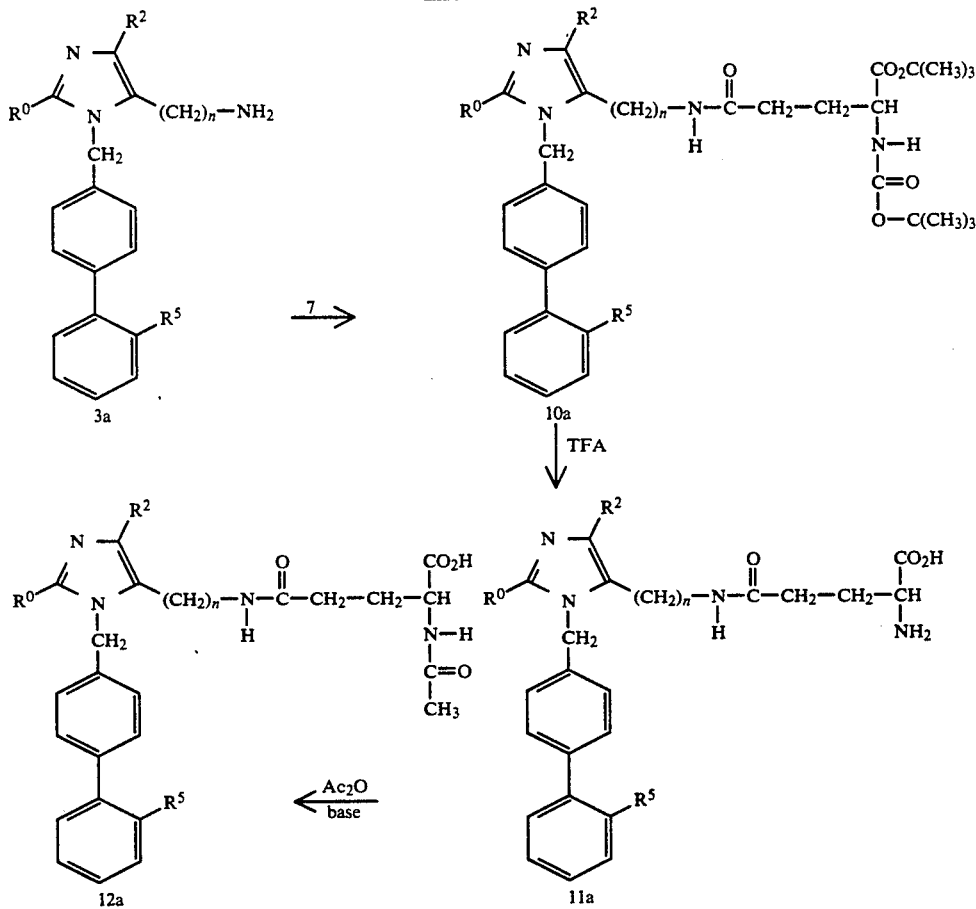

Synthetic Scheme IV shows the preparation of renal-selective angiotensin II antagonists by coupling γ-glutamic acid with one of the angiotensin II antagonist regiosiomers 3a which contains an amino moiety in the imidazole R[1] group (the synthesis of the other regioisomer is shown in Scheme V). In step 1, the AII antagonist 3a is reacted with the symmetrical anhydride of the protected γ-glutamic acid 7 to give 10a. In step 2, the protected material 10a is reacted with TFA to give the deprotected coupled material 11a. In step 3, the free amino compound 11a is acetylated with acetic anhydride in the presence of base to give the renal-selective angiotensin II antagonist 12b.

glutamic acid with one of the angiotensin II antagonist regioisomers 3b which contains an amino moiety in the imidazole R[1] group (the synthesis of the other regioisomer is shown in Scheme IV). In step 1, the AII antagonit 3b is reacted with the symmetrical anhydride of the protected γ-glutamic acid 7 to give 10b. In step 2, the protected material 10b is reacted with TFA to give the deprotected coupled material 11b. In step 3, the free amino compound 11b is acetylated with acetic anhy-

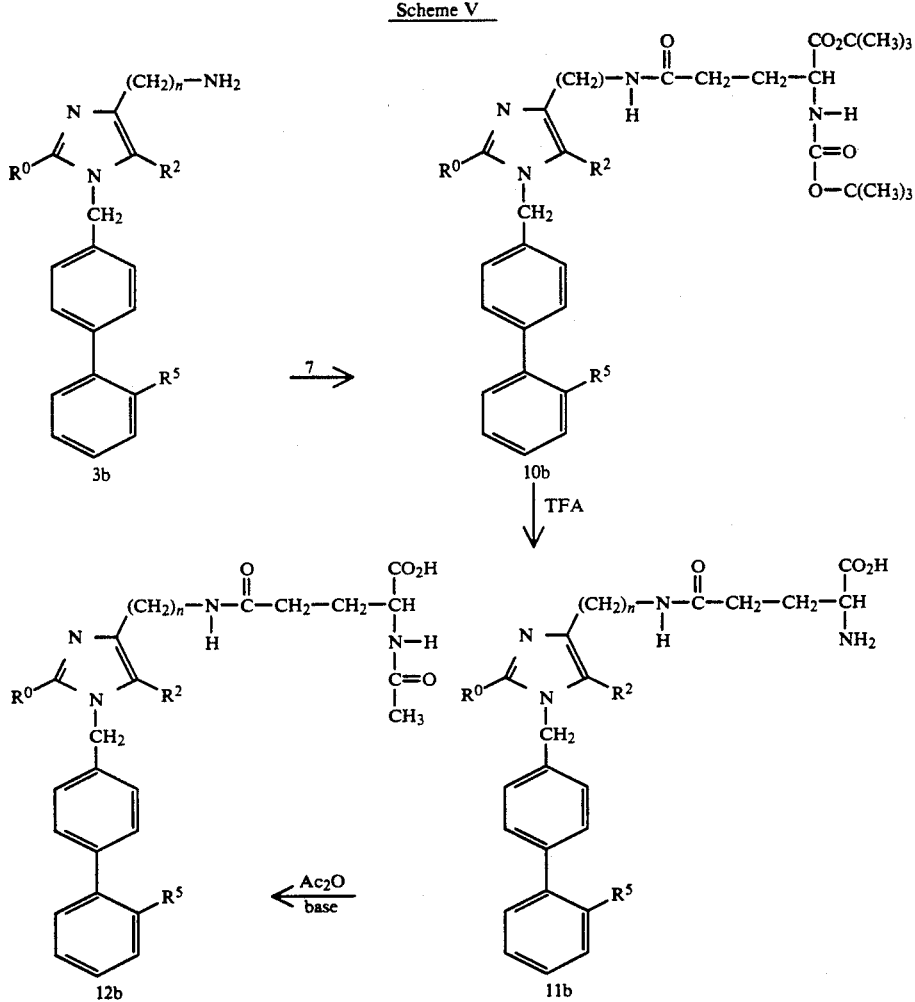

Synthetic Scheme V shows the preparation of renal-selective angiotensin II antagonists by coupling γ- dride in the presence of base to give the renal-selective angiotensin II antagonist 12b.

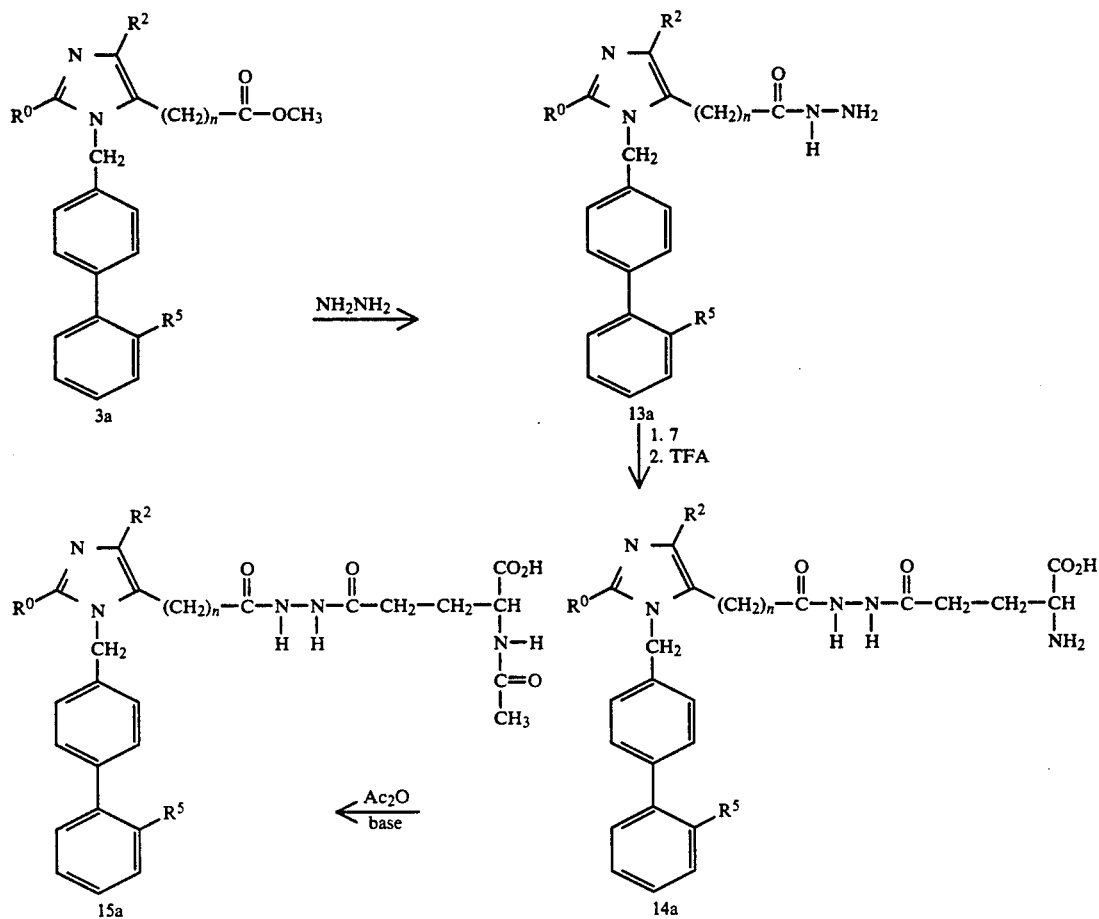

Scheme VI

Synthetic Scheme VI shows the preparation of renal-selective angiotensin II antagonists by coupling γ-glutamic acid with one of the angiotensin II antagonist regioisomers 3a which contains an acid moiety in the imidazole $R^1$ group (the synthesis of the other regioisomer is shown in Scheme VII); the imidazole $R^1$ acid moiety of the AII antagonist is coupled to the γ-acid moiety of glutamic acid via an hydrazine linker. In step 1, the methyl ester of the AII antagonist 3a is converted to the hydrazide 13a by the action of hydrazine. In step 2, the hydrazide 13a is first reacted with the symmetrical anhydride of the protected γ-glutamic acid 7 and subsequently reacted with TFA to give the deprotected coupled material 14a. In step 3, the free amino group of 14a is acetylated with acetic anhydride in the presence of base to give the renal-selective angiotensin II antagonist 15a.

Scheme VII

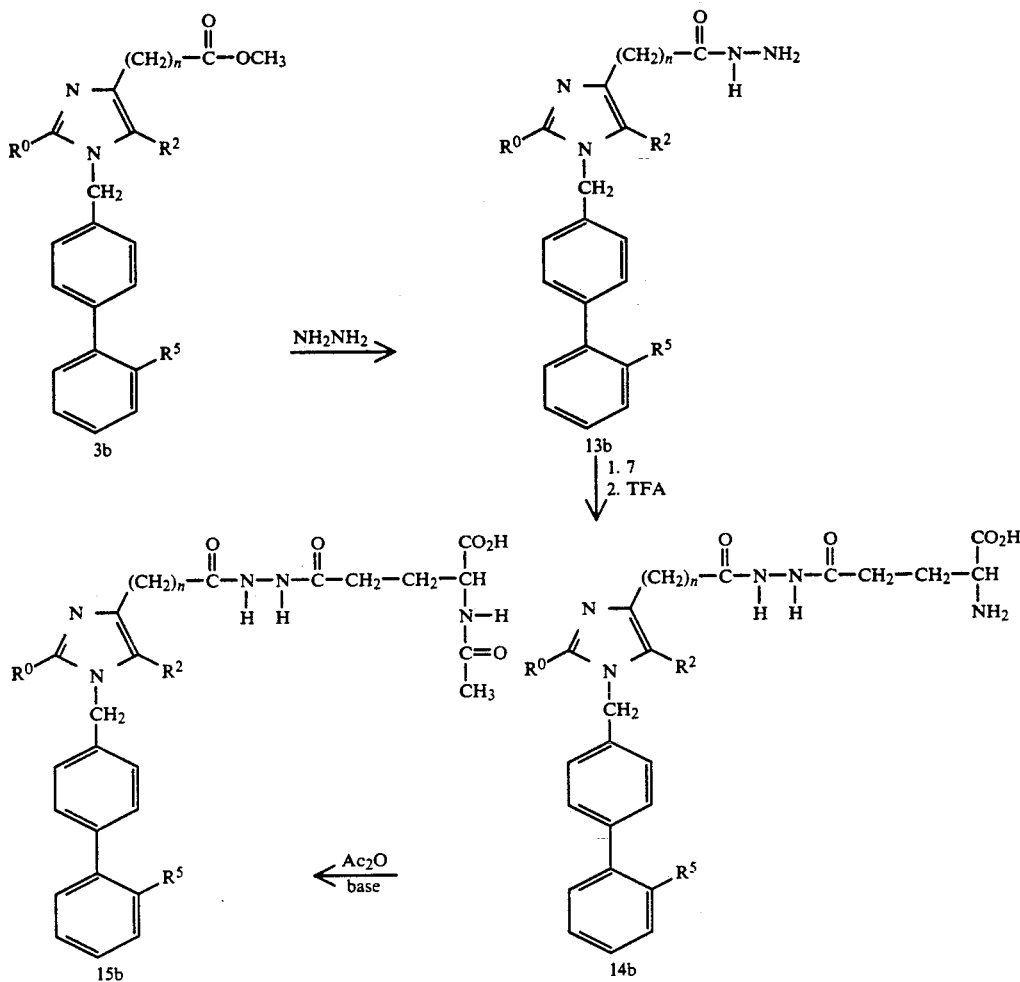

Synthetic Scheme VII shows the preparation of renal-selective angiotensin II antagonists by coupling γ-glutamic acid with one of the angiotensin II antagonist regioisomers 3b which contains an acid moiety in the imidazole $R^1$ group (the synthesis of the other isomer is shown in Scheme VII); the imidazole $R^1$ acid moiety of the AII antagonist is coupled to the γ-acid moiety of glutamic acid via an hydrazine linker. In step 1, the methyl ester of the AII antagonist 3b is converted to the hydrazide 13b by the action of hydrazine. In step 2, the hydrazide 13b is first reacted with the symmetrical anhydride of the protected γ-glutamic acid 7 and subsequently reacted with TFA to give the deprotected coupled material 14b. In step 3, the free amino group of 14b is acetylated with acetic anhydride in the presence of base to give the renal-selective angiotensin II antagonist 15b.

The following Examples 1-80 shown in Table IV are angiotensin II antagonists suitable for selection as precursors to provide the first residue of a conjugate of the invention. These angiotensin II antagonists may be prepared generally by the procedures outlined above in Scheme I. Also, specific procedures for preparation of Examples 1-80 of Table IV may be found in EP #253,310 published Jan. 20, 1988.

TABLE IV

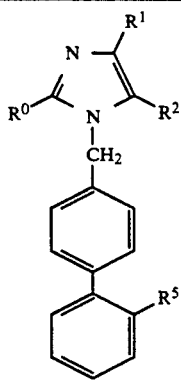

| Ex. # | R⁰ | R² | R¹ | R⁵ |
|---|---|---|---|---|
| 1 | $C_4H_9(n)$ | $CH_2OCOCH_3$ | Cl | $CO_2H$ |
| 2 | $C_4H_9(n)$ | $CH_2OH$ | $NO_2$ | $CO_2H$ |
| 3 | $C_4H_9(n)$ | $CH_2OH$ | $CF_3$ | $CO_2H$ |
| 4 | $SC_3H_7$ | $CH_2OH$ | H | $CO_2H$ |
| 5 | $C_4H_9(n)$ | $CH_2OH$ | Cl | $CO_2H$ |
| 6 | $C_4H_9(n)$ | Cl | $CH_2OH$ | $CO_2H$ |
| 7 | $C_4H_9(n)$ | H | $CH_2OH$ | $CO_2H$ |
| 8 | $C_4H_9(n)$ | $CH_2OH$ | H | $CO_2H$ |
| 9 | $C_4H_9(n)$ | $CH_2OCH_3$ | Cl | $CO_2H$ |
| 10 | $C_4H_9(n)$ | $CH_2OCH(CH_3)_2$ | Cl | $CO_2H$ |
| 11 | $C_4H_9(n)$ | $CH_2OH$ | Br | $CO_2H$ |
| 12 | $C_4H_9(n)$ | $CH_2OH$ | F | $CO_2H$ |
| 13 | $C_4H_9(n)$ | $CH_2OH$ | I | $CO_2H$ |
| 14 | cyclohexyl-$CH_2$ | $CH_2OH$ | Cl | $CO_2H$ |
| 15 | cyclohexyl | $CH_2OH$ | Cl | $CO_2H$ |
| 16 | $C_4H_9(n)$ | I | $CH_2OH$ | $CO_2H$ |
| 17 | $C_3H_7(n)$ | $CH_2OH$ | Cl | $CO_2H$ |
| 18 | $C_2H_5$ | $CH_2OH$ | Cl | $CO_2H$ |
| 19 | $C_3H_7(n)$ | $CH_2OH$ | Cl | $CO_2H$ |
| 20 | $C_5H_{11}(n)$ | $CH_2OH$ | Cl | $CO_2H$ |
| 21 | $C_6H_{13}(n)$ | $CH_2OH$ | Cl | $CO_2H$ |
| 22 | $C_4H_9(n)$ | $CH_2SH$ | Cl | $CO_2H$ |
| 23 | $C_4H_9(n)$ | $CH_2OC_6H_5$ | Cl | $CO_2H$ |
| 24 | $C_3H_7(n)$ | CHO | Cl | $CO_2H$ |
| 25 | $C_4H_9(n)$ | $CH_2CO_2H$ | Cl | $CO_2H$ |
| 26 | $C_4H_9(n)$ | $CH(CH_3)CO_2H$ | Cl | $CO_2H$ |
| 27 | $C_4H_9(n)$ | $NO_2$ | $CH_2OH$ | $CO_2H$ |
| 28 | $C_4H_9(n)$ | $CH_2OCOCH_3$ | Cl | $CO_2H$ |
| 29 | $C_4H_9(n)$ | $CH_2OCOCH_2CH_2$-phenyl | Cl | $CO_2H$ |
| 30 | $SC_4H_9(n)$ | $CH_2OH$ | H | $CO_2H$ |
| 31 | cyclopropyl-$CH_2S$ | $CH_2OH$ | H | $CO_2H$ |
| 32 | $C_4H_9(n)$ | CHO | Cl | $CO_2H$ |
| 33 | $C_4H_9(n)$ | $CO_2CH_3$ | Cl | $CO_2H$ |
| 34 | $C_4H_9(n)$ | $CONH_2$ | Cl | $CO_2H$ |
| 35 | (2-butenyl) | $CH_2OH$ | Cl | $CO_2H$ |
| 36 | (2-butenyl) | CHO | Cl | $CO_2H$ |
| 37 | $C_4H_9(n)$ | CHO | H | $CO_2H$ |
| 38 | $C_4H_9(n)$ | CHO | $CF_3$ | $CO_2H$ |

TABLE IV-continued

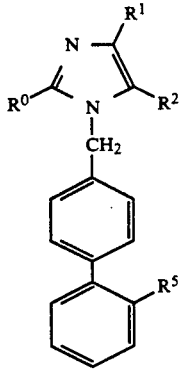

| Ex. # | R⁰ | R² | R¹ | R⁵ |
|---|---|---|---|---|
| 39 | $C_4H_9(n)$ | $CONHCH_3$ | Cl | $CO_2H$ |
| 40 | $C_4H_9(n)$ | $CON(CH_3)_2$ | Cl | $CO_2H$ |
| 41 | 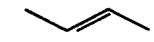 | $CH_2OH$ | Cl | $CO_2H$ |
| 42 |  | $CH_2OH$ | $CF_3$ | $CO_2H$ |
| 43 | 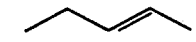 | CHO | Cl | $CO2H$ |
| 44 | $C_4H_9(n)$ | 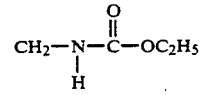 | Cl | $CO_2H$ |
| 45 | $C_4H_9(n)$ | 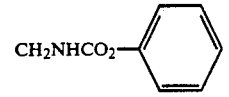 | Cl | $CO_2H$ |
| 46 | $C_4H_9(n)$ | $CH_2NHCO_2CH_3$ | Cl | $CO_2H$ |
| 47 | $C_4H_9(n)$ | $CH_2NHCO_2C_3H_7$ | Cl | $CO_2H$ |
| 48 | $C_4H_9(n)$ | $CH_2NHCO_2CH_2(CH_3)_2$ | Cl | $CO_2H$ |
| 49 | $C_4H_9(n)$ | $CH_2NHCO_2C_4H_9$ | Cl | $CO_2H$ |
| 50 | $C_4H_9(n)$ | $CH_2-NHCO_2\text{-adamantyl}$ | Cl | $CO_2H$ |
| 51 | $C_3H_7(n)$ | $CH_2NHCO_2CH_3$ | Cl | $CO_2H$ |
| 52 | $C_4H_9(n)$ | $CH_2NHCO_2CH_3$ | Cl | $CO_2H$ |
| 53 | $C_4H_9(n)$ | $CH_2NHCO_2C_2H_5$ | Cl | $CO_2H$ |
| 54 | $C_4H_9(n)$ | $CH_2NHCO_2C_3H_7$ | Cl | $CO_2H$ |
| 55 | $C_4H_9(n)$ | $CH_2NHCO_2C_4H_9$ | Cl | $CO_2H$ |
| 56 | $C_4H_9(n)$ | $CH_2NHCO_2CH(CH_3)_2$ | Cl | $CO_2H$ |
| 57 | $C_4H_9(n)$ | $CH_2NHCO_2(\text{1-naphthyl})$ | Cl | $CO_2H$ |
| 58 | $C_4H_9(n)$ | $CH_2NHCONHCH_3$ | Cl | $CO_2H$ |
| 59 | $C_4H_9(n)$ | $CH_2NHCONHC_2H_5$ | Cl | $CO_2H$ |
| 60 | $C_4H_9(n)$ | $CH_2NHCONHC_3H_7$ | Cl | $CO_2H$ |
| 61 | $C_4H_9(n)$ | $CH_2NHCONHC_4H_9$ | Cl | $CO_2H$ |
| 62 | $C_4H_9(n)$ | $CH_2NHCONHCH(CH_3)_2$ | Cl | $CO_2H$ |
| 63 | $C_4H_9(n)$ | $CH_2NHCONH(\text{1-napthyl})$ | Cl | $CO_2H$ |
| 64 | $C_3H_7(n)$ | 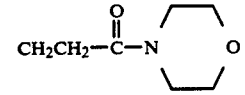 | H | $CO_2H$ |
| 65 | $C_3H_7(n)$ | 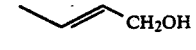 | Cl | $CO_2H$ |
| 66 | $C_3H_7(n)$ | 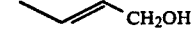 | Cl | $CO_2H$ |
| 67 | $C_4H_9(n)$ | 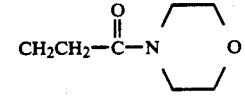 | Cl | $CO_2H$ |
| 68 | $C_4H_9(n)$ | $CH_2CH_2CO_2H$ | Cl | $CO_2H$ |

TABLE IV-continued

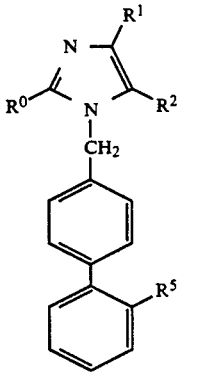

| Ex. # | R⁰ | R² | R¹ | R⁵ |
|---|---|---|---|---|
| 69 | $C_4H_9(n)$ | $CH_2CH_2CH_2CH_2CO_2H$ | Cl | $CO_2H$ |
| 70 | 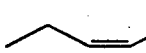 | $CH_2OH$ | Cl | $CO_2H$ |
| 71 | $C_4H_9(n)$ | 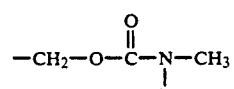 | Cl | $CO_2H$ |
| 72 | $C_4H_9(n)$ | 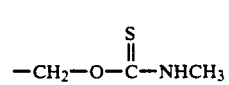 | Cl | $CO_2H$ |
| 73 | $C_4H_9(n)$ | 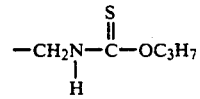 | H | $CO_2H$ |
| 74 | $C_4H_9(n)$ | 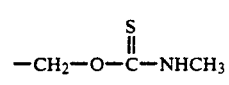 | H | $CO_2H$ |
| 75 | $C_4H_9(n)$ | $-CH_2CH_2CH_2F$ | Cl | $CO_2H$ |
| 76 | $C_4H_9(n)$ | $-CH_2ONO_2$ | Cl | $CO_2H$ |
| 77 | $C_4H_9(n)$ | 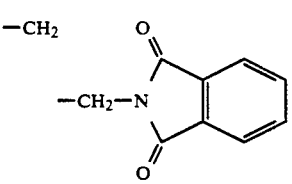 | Cl | $CO_2H$ |
| 78 | $C_4H_9(n)$ | $CH_2OH$ | Cl | $CN_4H$ |
| 79 | $C_4H_9(n)$ | Cl | $CH_2OH$ | $CN_4H$ |
| 80 | $C_4H_9(n)$ | CHO | Cl | $CN_4H$ |

A class of highly preferred specific conjugates of the invention is provided by conjugates formed from a biphenylmethyl 1H-substituted imidazole AII antagonist compound linked to a cleavable glutamyl residue. Each conjugate contains a diamino linker moiety which connects a terminal carboxylic acid moiety on the biphenylmethyl portion of the AII antagonist compound with a terminal carboxylic acid moiety on the gamma carbon of the cleavable glutamyl residue. Such conjugates are shown herein as Examples 81–146. General procedures for preparation of the conjugates of Examples 81–146 are described in Schemes II–III. Detailed procedures for preparation of representative conjugates are described in Examples 81 and 82. Similar procedures may be used for preparation of the conjugates identified as Examples 83–146 shown in Table V.

EXAMPLE 81

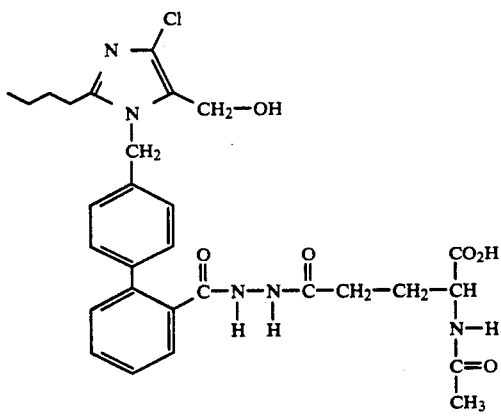

N-acetyl-L-glutamic acid,
5-[[4'-[2-butyl-4-chloro-5-(hydroxymethyl)-1H-imidazol-1-ylmethyl][1,1'-biphenyl]-2-yl]carbonyl]hydrazide Step 1: Preparation of
1-(2'-methoxycarbonyl-biphenyl-4-yl)methyl]-2-butyl-4-chloro-5-hydroxymethylimidazole.

Under nitrogen, a solution of 6.69 g (36 mmol) of 2-butyl-4-chloro-5-hydroxymethylimidazole in 100 mL of anhydrous dimethylformamide (DMF) was treated with molecular seives and 11.0 g (36 mmol) of 4-bromomethyl-2'-methoxycarbonylbiphenyl. The reaction was allowed to stir at ambient temperature overnight and then was filtered. The DMF was removed in vacuo and the residue was partitioned between water and chloroform; the chloroform extracts were combined, dried (MgSO$_4$), and concentrated in vacuo giving 17.4 g of crude material. Purification by silica gel chromatography (Waters Prep-500A) using ethyl acetate/hexane (40:60) gave the 4-hydroxymethyl isomer as the regioisomer with the lower Rf value and 6.27 g (42%) of the 5-hydroxymethyl isomer: NMR (CDCl$_3$) δ 0.91 (t, J=7 Hz, 3H), 1.29–1.44 (m, 2H), 1.52 (t, J=8 Hz, 1H), 1.63–1.76 (m, 2H), 2.62 (t, J=7 Hz, 2H), 3.65 (s, 3H), 4.54 (d, J=8 Hz, 2H), 7.02–7.08 (m, 2H), 7.25–7.36 (m, 3H), 7.38–7.47 (m, 1H), 7.50–7.58 (m, 1H), 7.83–7.90 (m, 1H).

Step 2: Preparation of
1-[(2'-hydrazinylcarbonyl-biphenyl-4-yl)methyl]-2-butyl-4-chloro-5-hydroxymethylimidazole.

Under nitrogen, 6.27 g (15 mmol) of the 5-hydroxymethyl ester from step 1 was dissolved in 100 mL of methanol and treated with 15 mL (480 mmol) of anhydrous hydrazine. The reaction was allowed to stir at reflux overnight; concentration in vacuo gave 4.83 g of crude material. Purification by silica gel chromatography (Waters Prep-500A) using isopropanol/ethyl acetate (20:80) gave 4.27 g (68%) of the hydrazide as a colorless glass: NMR (CDCl$_3$) δ 0.81 (t, J=7 Hz, 3H), 1.18–1.34 (m, 2H), 1.42–1.56 (m, 2H), 2.50 (t, J=Hz, 2H), 4.15–4.35 (br s, 2H), 4.35 (d, J=8 Hz, 2H), 5.24 (t, J=8 Hz, 1H), 7.05–7.13 (m, 2H), 7.32–7.44 (m, 5H), 7.45–7.54 (m, 1H), 9.34 (s, 1H).

Step 3: Preparation of N-acetyl-L-glutamic acid,
5-[[4'-2-butyl-4-chloro-5-(hydroxymethyl)-1H-imidazol-1-ylmethyl][1,1'-biphenyl]-2-yl]carbonyl]hydrazide.

To a solution of 1.70 g (5.60 mmol) of N-Boc-L-glutamic acid-α-tertbutyl ester (BACHEM) in 50 mL of methylene chloride under nitrogen was added 580 mg (2.8 mmol) of solid dicyclohexylcarbodiimide (DCC). The reaction was allowed to stir for 2 h and filtered under nitrogen. The anhydride solution was then added to a solution of 1.0 g (2.4 mmol) of hydrazide from step 2 in 75 mL of methylene chloride under nitrogen. The reaction was stirred overnight, concentrated to a volume of 25 mL, cooled to 0° C., and treated with 25 mL of TFA under nitrogen. The stirred reaction was allowed to warm to ambient temperature overnight and concentrated in vacuo. The crude product wad dissolved in 100 mL of acetonitrile/water (1:1) and the pH adjusted to 8 with 1M K$_2$CO$_3$. The solution was cooled to 0° and 0.23 mL (2.4 mmol) of acetic anhydride and 2.4 mL (2.4 mmol) of 1M K$_2$CO$_3$ was added every 30 min for 5 h; the pH was maintained at 9 and the reaction temperature kept below 5° C. After the last addition, the reaction was allowed to warm to ambient temperature overnight. The pH was adjusted to 4 with 3M HCl and the reaction was concentrated to 100 mL. Purification by reverse phase chromatography (Waters Deltaprep-3000) using isocratic 25% acetonitrile/water (0.05% TFA) gave 1.0 g 75% overall yield from the hydrazide of step 2) of colorless product: NMR (DMSO-d$_6$) δ 0.81 (t, J=7Hz, 3H), 1.20–1.30 (m, 2H), 1.42–1.55 (m, 2H), 1.75–1.84 (m, 2H), 1.85 (s, 3H), 1.89–2.05 (m, 2H), 2.21 (t, J=7Hz, 2H), 4.13–4.24 (m, 1H), 4.35 (s, 2H), 7.05–7.12 (m, 2H), 7.37–7.58 (m, 6H), 8.12–8.17 (m, 2H); MS (FAB) m/e (rel. intensity) 584 (18), 568 (100), 225 (64); HRMS. Calcd for M+H: 584.2276. Found: 584.2240.

EXAMPLE 82

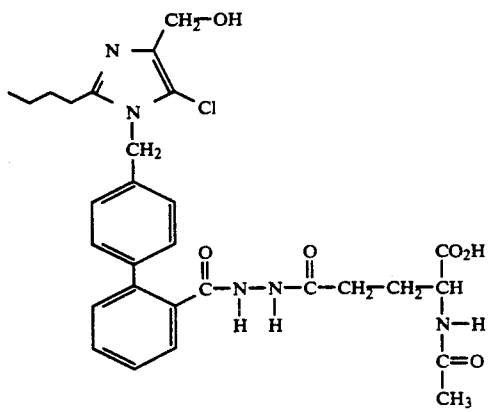

N-acetyl-L-glutamic acid, 5-[[4'-[2-butyl-5-chloro-4-(hydroxymethyl)-1H-imidazol-1-ylmethyl][1,1'-biphenyl]-2-yl]carbonyl]hydrazide

Step 1: Preparation of 1-[(2'-hydrazinylcarbonyl-biphenyl-4-yl)methyl]-2-butyl-5-chloro-4-hydroxymethylimidazole.

Under nitrogen, 4.13 g (10 mmol) of the 4-hydroxymethyl ester from step 1 of Example 81 is dissolved in 100 mL of methanol and is treated with 15 mL of (480 mmol) of anhydrous hydrazine. The reaction is allowed to stir at reflux overnight; concentration in vacuo gives the crude material. Purification by silica gel chromatography (Waters Prep-500A) gives the pure hydrazide.

Step 2: Preparation of N-acetyl-L-glutamic acid. 5-[[4'-2-butyl-5-chloro-4-(hydroxymethyl)-1H-imidazol-1-ylmethyl][1,1'-biphenyl]-2-yl]carbonyl]hydrazide To a solution of 1.70 g (5.6 mmol) of N-Boc-L-glutamic acid-o-tertbutyl ester (BACHEM) in 50 mL of methylene chloride under nitrogen is added 580 mg (2.8 mmol) of solid dicylcohexylcarbodiimide (DCC). The reaction is allowed to stir for 2 h and is filtered under nitrogen. The anhydride solution is then added to a solution of 1.0 g (2.4 mmol) of the hydrazide from step 1 in 75 mL of methylene chloride under nitrogen. The reaction is stirred overnight, is concentrated to a volume of 25 mL, is cooled to 0° C., and is treated with 25 mL of TFA under nitrogen. The stirred reaction is allowed to warm to ambient temperature overnight and is concentrated in vacuo. The crude product is dissolved in 100 mL of acetonitrile/water (1:1) and the pH is adjusted to 8 with 1M $K_2CO_3$. The solution is cooled to 0° C. and 0.23 mL (2.4 mmol) of acetic anhydride and 2.4 mL (2.4 mmol) of 1M $K_2CO_3$ is added every 30 min for 5 h; the pH is maintained at 9 and the reaction temperature is kept below 5° C. After the last addition, the reaction is allowed to warm to ambient temperature overnight. The pH is adjusted to 4 with 3M HCl and the reaction is concentrated to 100 mL. Purification by reverse phase chromatography (Waters Deltaprep-3000) gives the product.

TABLE V

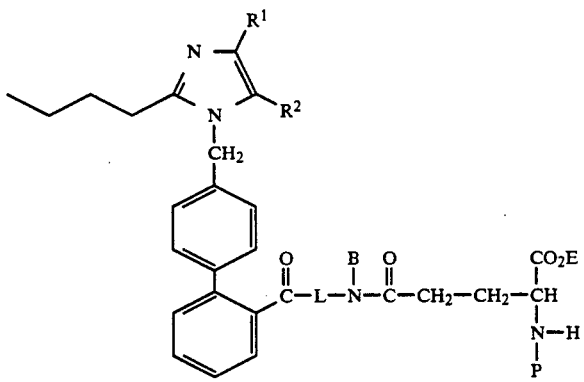

| Ex. # | $R^2$ | $R^1$ | L | B | E | P |
|---|---|---|---|---|---|---|
| 83 | $CH_2OH$ | Cl | —NH— | H | H | H |
| 84 | $CH_2OH$ | Cl | —NH— | H | $CH_3$ | H |
| 85 | $CH_2OH$ | Cl | —NH— | H | $CH_3$ | $COCH_3$ |
| 86 | $CH_2OH$ | Cl | —NH— | H | $C_2H_5$ | $COCH_3$ |
| 87 | $CH_2OH$ | Cl | —NH— | H | $C_2H_5$ | H |
| 88 | $CH_2OH$ | Cl | —NH— | H | H | $COCH_2Cl$ |
| 89 | $CH_2OH$ | Cl | —NH— | H | H | $COC_4H_9(n)$ |
| 90 | Cl | $CH_2OH$ | —NH— | H | H | H |
| 91 | $CH_2OH$ | Cl | —$NHCH_2CH_2$— | H | H | $COCH_3$ |
| 92 | $CH_2OH$ | Cl | —$NHCH_2CH_2$— | H | H | H |
| 93 | $CH_2OH$ | Cl | —$NHCH_2CH_2$— | H | $CH_3$ | H |
| 94 | $CH_2OH$ | Cl | —$NHCH_2CH_2$— | H | $CH_3$ | $COCH_3$ |
| 95 | $CH_2OH$ | Cl | —$NHCH_2CH_2$— | H | $C_2H_5$ | $COCH_3$ |
| 96 | $CH_2OH$ | Cl | —$NHCH_2CH_2$— | H | $C_2H_5$ | H |
| 97 | $CH_2OH$ | Cl | —$NHCH_2CH_2$— | H | H | $COCH_2Cl$ |
| 98 | $CH_2OH$ | Cl | —$NHCH_2CH_2$— | H | H | $COC_4H_9(n)$ |
| 99 | Cl | $CH_2OH$ | —$NHCH_2CH_2$— | H | H | $COCH_3$ |
| 100 | Cl | $CH_2OH$ | —$NHCH_2CH_2$— | H | H | H |
| 101 | $CH_2OH$ | Cl | —N⟨piperazinyl⟩N—* | H | H | $COCH_3$ |
| 102 | $CH_2OH$ | Cl | —N⟨piperazinyl⟩N—* | H | H | H |
| 103 | $CH_2OH$ | Cl | —N⟨piperazinyl⟩N—* | H | $CH_3$ | H |

TABLE V-continued

| Ex. # | R² | R¹ | L | B | E | P |
|---|---|---|---|---|---|---|
| 104 | CH₂OH | Cl | -N⟨piperazine⟩N- | * | CH₃ | COCH₃ |
| 105 | CH₂OH | Cl | -N⟨piperazine⟩N- | * | C₂H₅ | COCH₃ |
| 106 | CH₂OH | Cl | -N⟨piperazine⟩N- | * | C₂H₅ | H |
| 107 | CH₂OH | Cl | -N⟨piperazine⟩N- | * | H | COC₄H₉(n)) |
| 108 | CH₂OH | Cl | -N⟨piperazine⟩N- | * | H | COC₄H₉(n)) |
| 109 | Cl | CH₂OH | -N⟨piperazine⟩N- | * | H | COCH₃ |
| 110 | Cl | CH₂OH | -N⟨piperazine⟩N- | * | H | H |
| 111 | CH₂OCH₃ | Cl | —NH— | H | H | COCH₃ |
| 112 | CH₂OCH₃ | Cl | —NH— | H | H | H |
| 113 | Cl | CH₂OCH₃ | —NH— | H | H | COCH₃ |
| 114 | Cl | CH₂OCH₃ | —NH— | H | H | H |
| 115 | CH₂OH | CF₃ | —NH— | H | H | COCH₃ |
| 116 | CH₂OH | CF₃ | —NH— | H | H | H |
| 117 | CH₂OH | C₂F₅ | —NH— | H | H | COCH₃ |
| 118 | CH₂OH | C₂F₅ | —NH— | H | H | H |
| 119 | CH₂OH | C₃H₇ | —NH— | H | H | COCH₃ |
| 120 | CH₂OH | C₃F₇ | —NH— | H | H | H |
| 121 | CHO | Cl | —NH— | H | H | COCH₃ |
| 122 | CHO | Cl | —NH— | H | H | H |
| 123 | Cl | CHO | —NH— | H | H | COCH₃ |
| 124 | Cl | CHO | —NH— | H | H | H |
| 125 | CO₂H | Cl | —NH— | H | H | COCH₃ |
| 126 | CO₂H | Cl | —NH— | H | H | COCH₃ |
| 127 | Cl | CO₂H | —NH— | H | H | COCH₃ |
| 128 | Cl | CO₂H | —NH— | H | H | H |
| 129 | CH₂OH | Br | —NH— | H | H | COCH₃ |
| 130 | CH₂OH | Br | —NH— | H | H | H |
| 131 | Cl | CHO | —NHCH₂CH₂— | H | H | COCH₃ |
| 132 | Cl | CHO | —NHCH₂CH₂— | H | H | H |
| 133 | CO₂H | Cl | —NHCH₂CH₂— | H | H | COCH₃ |
| 134 | CO₂H | Cl | —NHCH₂CH₂— | H | H | H |
| 135 | Cl | CO₂H | —NHCH₂CH₂— | H | H | COCH₃ |
| 136 | Cl | CO₂H | —NHCH₂CH₂— | H | H | H |
| 137 | CH₂OH | Br | —NHCH₂CH₂— | H | H | COCH₃ |
| 138 | CH₂OH | Br | —NHCH₂CH₂— | H | H | H |
| 139 | Cl | CHO | -N⟨piperazine⟩N- | * | H | COCH₃ |

TABLE V-continued

[Structure: 2-butyl-1H-imidazole with R¹ at 4-position, R² at 5-position, N-CH₂-biphenyl where the other phenyl bears -C(O)-L-N(B)-C(O)-CH₂-CH₂-CH(CO₂E)-NH-P]

| Ex. # | R² | R¹ | L | B | E | P |
|---|---|---|---|---|---|---|
| 140 | Cl | CHO | -N⟨piperidine⟩N- | * | H | H |
| 141 | CO₂H | Cl | -N⟨piperidine⟩N- | * | H | COCH₃ |
| 142 | CO₂H | Cl | -N⟨piperidine⟩N- | * | H | H |
| 143 | Cl | CO₂H | -N⟨piperidine⟩N- | * | H | COCH₃ |
| 144 | Cl | CO₂H | -N⟨piperidine⟩N- | * | H | H |
| 145 | CH₂OH | Br | -N⟨piperidine⟩N- | * | H | COCH₃ |
| 146 | CH₂OH | Br | -N⟨piperidine⟩N- | * | H | H |

\*  —L—N(B)— equals piperazinyl

Another class of highly preferred specific conjugates of the invention is provided by conjugates formed from a biphenylmethyl 1H-substituted imidazole AII antagonist compound having a terminal amino group attached to the imidazole nucleus. In this family of conjugates, the cleavable glutamyl residue is attached through an amide bond formed between the carbonyl at the gamma carbon of the glutamyl residue and the terminal amino nitrogen of the AII antagonist imidazole nucleus. Such conjugates are shown as Examples #147–#710. General procedures for preparation of the conjugates of Examples #147–#710 are described in Schemes IV–V. Detailed procedures for preparation of representative conjugates are described in Examples #147 and #148. Procedures similar to these aforementioned general and specific procedures may be used for preparation of the conjugates identified as Examples #149–#710 shown in Table VI.

EXAMPLE 147

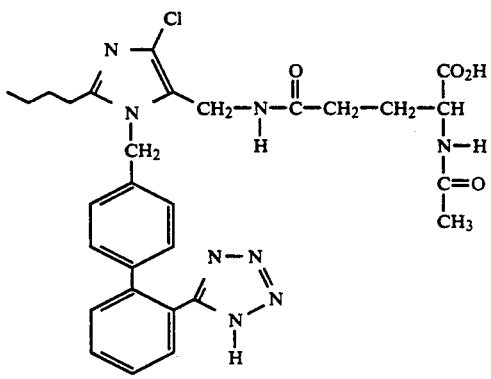

N2-acetyl-N-[[2-butyl-4-chloro-1-[[2'-(1H-tetrazol-5-yl)[1,1'-biphenyl]-4-yl]methyl]-1H-imidazol-5-yl]methyl]-L-glutamine Step 1: Preparation of 5-aminomethyl-2-butyl-4-chloro-1-[(2'-[1H-tetrazol-5-yl)biphenyl-4-methyl]imidazole.

A solution of 4.20 g (10 mmol) of the compound of Example 80, 7.7 g (100 mmol) of ammonium acetate, and 439 mg (7 mmol) of NaBH$_3$CN in 30 mL of absolute methanol is stirred at ambient temperature for 48 h. Concentrated HCl is added until pH<2, and the methanol is removed in vacuo. The residue is dissolved in water and is extracted with ethyl acetate. The aqueous solution is brought to pH>10 with 50% NaOH, is saturated with NaCl, and is extracted with methylene chloride. The extracts are combined, are dried (MgSO$_4$), and are evaporated in vacuo to give the crude product. Purification by reverse phase chromatography (Waters DeltaPrep-3000) provides the pure 5-aminomethyl product.

Step 2: Preparation of N2-acetyl-N-[[2-butyl-4-chloro-1-[[2'-(1H-tetrazol-5-yl)[1,1'-biphenyl]-4-yl]methyl]-1H-imidazol-5-yl]methyl]-L-glutamine To a solution of 1.70 g (5.6 mmol) of N-Boc-L-glutamic acid-o-tertbutyl ester (BACHEM) in 50 mL of methylene chloride under nitrogen is added 580 mg (2.8 mmol) of solid dicylcohexylcarbodiimide (DCC). The reaction is allowed to stir for 2 h and is filtered under nitrogen. The anhydride solution is then added to a solution of 1.01 g (2.4 mmol) of the 5-aminomethyl compound of step 1 in 75 mL of methylene chloride under nitrogen. The reaction is stirred overnight, is concentrated to a volume of 25 mL, is cooled to 0° C., and is treated with 25 mL of TFA under nitrogen. The stirred reaction is allowed to warm to ambient temperature overnight and is concentrated in vacuo. The crude product is dissolved in 100 mL of acetonitrile/water (1:1) and the pH is adjusted to 8 with 1M K$_2$CO$_3$. The solution is cooled to 0° C. and 0.23 mL (2.4 mmol) of acetic anhydride and 2.4 mL (2.4 mmol) of 1M K$_2$CO$_3$ is added every 30 min for 5 h; the pH is maintained at 9 and the reaction temperature is kept below 5° C. After the last addition, the reaction is allowed to warm to ambient temperature overnight. The pH is adjusted to 4 with 3M HCl and the reaction is concentrated to 100 mL. Purification by reverse phase chromatography (Waters Delta- prep-3000) gives the pure product.

EXAMPLE 148

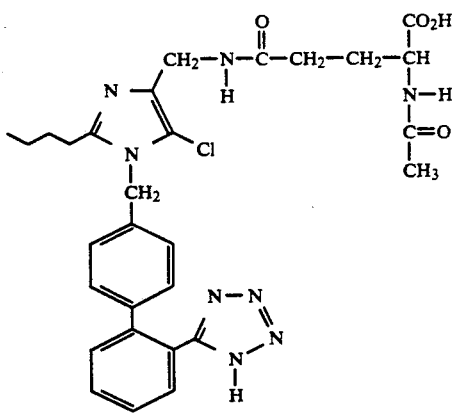

N2-acetyl-N-[[2-butyl-5-chloro-1-[[2'-(1H-tetrazol-5-yl)[1,1'-biphenyl]-4-yl]methyl]-1H-imidazol-4-yl]methyl]-L-glutamine Step 1: Preparation of 2-butyl-5-chloro-4-formyl-1-(2'-(1H-tetrazol-5-yl)biphenyl-4-methyl]imidazole.

A mixture of 2.11 g (5.0 mmol) of the compound of Example 79 and 3.08 g (35 mmol) of activated manganese dioxide in 30 mL of methylene chloride at ambient temperature is stirred for 40 h. The reaction mixture is filtered through celite, and the filtrate is concentrated in vacuo. Purification by reverse phase chromatography provided the pure 4-formyl product.

Step 2: Preparation of 4-aminomethyl-2-butyl-5-chloro-1-[(2'-(1H-tetrazol-5-yl)biphenyl-4-methyl]imidazole.

A solution of 4.20 g (10 mmol) of the aldehyde from step 1, 7.7 g (100 mmol) of ammonium acetate, and 439 mg (7 mmol) of NaBH$_3$CN in 30 mL of absolute methanol is stirred at ambient temperature for 48 h. Concentrated HCl is added until pH<2, and the methanol is removed in vacuo. The residue is dissolved in water and is extracted with ethyl acetate. The aqueous solution is brought to pH>10 with 50% NaOH, is saturated with NaCl, and is extracted with methylene chloride. The extracts are combined, are dried (MgSO$_4$), and are evaporated in vacuo to give the crude product. Purification by reverse phase chromatography (Waters Deltaprep-3000)) provides the pure product.

Step 3: Preparation of N2-acetyl-N-[[2-butyl-5-chloro-1-[[2'-(1H-tetrazol-5-yl)[1,1'-biphenyl]-4-yl]methyl]-1H-imidazol-4-yl]methyl]-L-glutamine To a solution of 1.70 g (5.6 mmol) of N-Boc-L-glutamic acid-α-tertbutyl ester (BACHEM) in 50 mL of methylene chloride under nitrogen is added 580 mg (2.8 mmol) of solid dicylcohexylcarbodiimide (DCC). The reaction is allowed to stir for 2 h and is filtered under nitrogen. The anhydride solution is then added to a solution of 1.01 g (2.4 mmol) of the 4-aminomethyl compound of step 2 in 75 mL of methylene chloride under nitrogen. The reaction is stirred overnight, is concentrated to a volume of 25 mL, is cooled to 0° C., and is treated with 25 mL of TFA under nitrogen. The stirred reaction is allowed to warm to ambient temperature overnight and is concentrated in vacuo. The crude product is dissolved in 100 mL of acetonitrile/water (1:1) and the pH is adjusted to 8 with 1M $K_2CO_3$. The solution is cooled to 0° C. and 0.23 mL (2.4 mmol) of acetic anhydride and 2.4 mL (2.4 mmol) of 1M $K_2CO_3$ is added every 30 min for 5 h; the pH is maintained at 9 and the reaction temperature is kept below 5° C. After the last addition, the reaction is allowed to warm to ambient temperature overnight. The pH is adjusted to 4 with 3M HCl and the reaction is concentrated to 100 mL. Purification by reverse phase chromatography (Waters Delta-prep-3000) gives the pure product.

TABLE VI

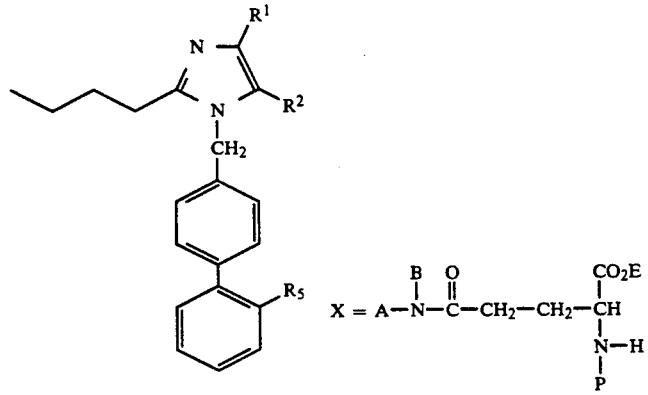

| Ex: # | $R^1$ | $R^2$ | $R_5$ | A | B | E | P |
|---|---|---|---|---|---|---|---|
| 149 | Cl | X | $CO_2H$ | single bond | H | H | $COCH_3$ |
| 150 | Cl | X | $CO_2H$ | single bond | H | H | $COCH_2Cl$ |
| 151 | Cl | X | $CO_2H$ | single bond | H | H | $COC_4H_9$ |
| 152 | Cl | X | $CO_2H$ | single bond | H | $CH_3$ | $COCH_3$ |
| 153 | Cl | X | $CO_2H$ | single bond | H | $C_2H_5$ | $COCH_3$ |
| 154 | Cl | X | $CN_4H$ | single bond | H | H | $COCH_3$ |
| 155 | Cl | X | $CN_4H$ | single bond | H | H | $COCH_2Cl$ |
| 156 | Cl | X | $CN_4H$ | single bond | H | H | $COC_4H_9$ |
| 157 | Cl | X | $CN_4H$ | single bond | H | $CH_3$ | $COCH_3$ |
| 158 | Cl | X | $CN_4H$ | single bond | H | $C_2H_5$ | $COCH_3$ |
| 159 | Cl | X | $CO_2H$ | single bond | H | H | H |
| 160 | Cl | X | $CO_2H$ | single bond | H | $CH_3$ | H |
| 161 | Cl | X | $CO_2H$ | single bond | H | $C_2H_5$ | H |
| 162 | Cl | X | $CN_4H$ | single bond | H | H | H |
| 163 | Cl | X | $CN_4H$ | single bond | H | $CH_3$ | H |
| 164 | Cl | X | $CN_4H$ | single bond | H | $C_2H_5$ | H |
| 165 | Cl | X | $CO_2H$ | $-CH_2-$ | H | H | $COCH_3$ |
| 166 | Cl | X | $CO_2H$ | single bond | H | H | $COCH_2Cl$ |
| 167 | Cl | X | $CO_2H$ | single bond | H | H | $COC_4H_9$ |
| 168 | Cl | X | $CO_2H$ | single bond | H | $CH_3$ | $COCH_3$ |
| 169 | Cl | X | $CO_2H$ | single bond | H | $C_2H_5$ | $COCH_3$ |
| 170 | Cl | X | $CN_4H$ | single bond | H | H | $COCH_2Cl$ |
| 171 | Cl | X | $CN_4H$ | single bond | H | H | $COC_4H_9$ |
| 172 | Cl | X | $CN_4H$ | single bond | H | $CH_3$ | $COCH_3$ |
| 173 | Cl | X | $CN_4H$ | single bond | H | $C_2H_5$ | $COCH_3$ |
| 174 | Cl | X | $CO_2H$ | $-CH_2-$ | H | H | H |
| 175 | Cl | X | $CO_2H$ | single bond | H | $CH_3$ | H |
| 176 | Cl | X | $CO_2H$ | single bond | H | $C_2H_5$ | H |
| 177 | Cl | X | $CN_4H$ | $-CH_2-$ | H | H | H |
| 178 | Cl | X | $CN_4H$ | single bond | H | $CH_3$ | H |
| 179 | Cl | X | $CN_4H$ | single bond | H | $C_2H_5$ | H |
| 180 | Cl | X | $CN_4H$ | $-CH_2-$ | $CH_3$ | H | H |
| 181 | Cl | X | $CN_4H$ | $-CH_2-$ | $CH_3$ | H | $COCH_3$ |
| 182 | Cl | X | $CO_2H$ | $-CH_2CH_2-$ | H | H | $COCH_3$ |
| 183 | Cl | X | $CO_2H$ | single bond | H | H | $COCH_2Cl$ |
| 184 | Cl | X | $CO_2H$ | single bond | H | H | $COC_4H_9$ |
| 185 | Cl | X | $CO_2H$ | single bond | H | $CH_3$ | $COCH_3$ |
| 186 | Cl | X | $CO_2H$ | single bond | H | $C_2H_5$ | $COCH_3$ |
| 187 | Cl | X | $CN_4H$ | $-CH_2CH_2-$ | H | H | $COCH_3$ |
| 188 | Cl | X | $CN_4H$ | single bond | H | H | $COCH_2Cl$ |
| 189 | Cl | X | $CN_4H$ | single bond | H | H | $COC_4H_9$ |
| 190 | Cl | X | $CN_4H$ | single bond | H | $CH_3$ | $COCH_3$ |
| 191 | Cl | X | $CN_4H$ | single bond | H | $C_2H_5$ | $COCH_3$ |
| 192 | Cl | X | $CO_2H$ | $-CH_2CH_2-$ | H | H | H |
| 193 | Cl | X | $CO_2H$ | single bond | H | $CH_3$ | H |
| 194 | Cl | X | $CO_2H$ | single bond | H | $C_2H_5$ | H |
| 195 | Cl | X | $CN_4H$ | $-CH_2CH_2-$ | H | H | H |
| 196 | Cl | X | $CN_4H$ | single bond | H | $CH_3$ | H |
| 197 | Cl | X | $CN_4H$ | single bond | H | $C_2H_5$ | H |
| 198 | Cl | X | $CO_2H$ | $C_3H_6(n)$ | H | H | $COCH_3$ |
| 199 | Cl | X | $CO_2H$ | single bond | H | H | $COCH_2Cl$ |
| 200 | Cl | X | $CO_2H$ | single bond | H | H | $COC_4H_9$ |
| 201 | Cl | X | $CO_2H$ | single bond | H | $CH_3$ | $COCH_3$ |

TABLE VI-continued

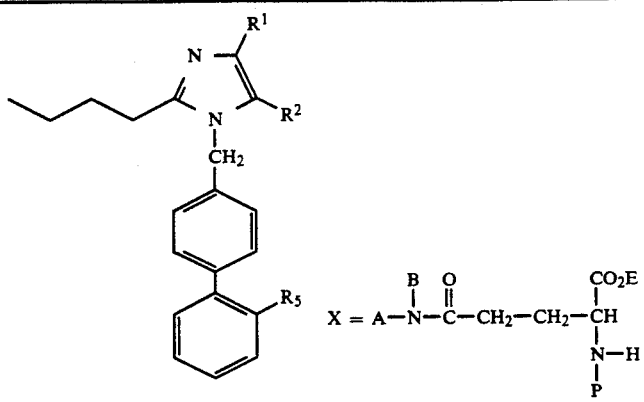

| Ex: # | R¹ | R² | R₅ | A | B | E | P |
|---|---|---|---|---|---|---|---|
| 202 | Cl | X | $CO_2H$ | single bond | H | $C_2H_5$ | $COCH_3$ |
| 203 | Cl | X | $CN_4H$ | $C_3H_6(n)$ | H | H | $COCH_3$ |
| 204 | Cl | X | $CN_4H$ | single bond | H | H | $COCH_2Cl$ |
| 205 | Cl | X | $CN_4H$ | single bond | H | H | $COC_4H_9$ |
| 206 | Cl | X | $CN_4H$ | single bond | H | $CH_3$ | $COCH_3$ |
| 207 | Cl | X | $CN_4H$ | single bond | H | $C_2H_5$ | $COCH_3$ |
| 208 | Cl | X | $CO_2H$ | $C_3H_6(n)$ | H | H | H |
| 209 | Cl | X | $CO_2H$ | single bond | H | $CH_3$ | H |
| 210 | Cl | X | $CO_2H$ | single bond | H | $C_2H_5$ | H |
| 211 | Cl | X | $CN_4H$ | $C_3H_6(n)$ | H | H | H |
| 212 | Cl | X | $CN_4H$ | single bond | H | $CH_3$ | H |
| 213 | Cl | X | $CN_4H$ | single bond | H | $C_2H_5$ | H |
| 214 | Cl | X | $CO_2H$ | $C_4H_8(n)$ | H | H | $COCH_3$ |
| 215 | Cl | X | $CO_2H$ | single bond | H | H | $COCH_2Cl$ |
| 216 | Cl | X | $CO_2H$ | single bond | H | H | $COC_4H_9$ |
| 217 | Cl | X | $CO_2H$ | single bond | H | $CH_3$ | $COCH_3$ |
| 218 | Cl | X | $CO_2H$ | single bond | H | $C_2H_5$ | $COCH_3$ |
| 219 | Cl | X | $CN_4H$ | $C_4H_8(n)$ | H | H | $COCH_3$ |
| 220 | Cl | X | $CN_4H$ | single bond | H | H | $COCH_2Cl$ |
| 221 | Cl | X | $CN_4H$ | single bond | H | H | $COC_4H_9$ |
| 222 | Cl | X | $CN_4H$ | single bond | H | $CH_3$ | $COCH_3$ |
| 223 | Cl | X | $CN_4H$ | single bond | H | $C_2H_5$ | $COCH_3$ |
| 224 | Cl | X | $CO_2H$ | $C_4H_8(n)$ | H | H | H |
| 225 | Cl | X | $CO_2H$ | single bond | H | $CH_3$ | H |
| 226 | Cl | X | $CO_2H$ | single bond | H | $C_2H_5$ | H |
| 227 | Cl | X | $CN_4H$ | $C_4H_8(n)$ | H | H | H |
| 228 | Cl | X | $CN_4H$ | single bond | H | $CH_3$ | H |
| 229 | Cl | X | $CN_4H$ | single bond | H | $C_2H_5$ | H |
| 230 | Cl | X | $CO_2H$ | *p-phenylene* | H | H | $COCH_3$ |
| 231 | Cl | X | $CO_2H$ | single bond | H | H | $COCH_2Cl$ |
| 232 | Cl | X | $CO_2H$ | single bond | H | H | $COC_4H_9$ |
| 233 | Cl | X | $CO_2H$ | single bond | H | $CH_3$ | $COCH_3$ |
| 234 | Cl | X | $CO_2H$ | single bond | H | $C_2H_5$ | $COCH_3$ |
| 235 | Cl | X | $CN_4H$ | *p-phenylene* | H | H | $COCH_3$ |
| 236 | Cl | X | $CN_4H$ | single bond | H | H | $COCH_2Cl$ |
| 237 | Cl | X | $CN_4H$ | single bond | H | H | $COC_4H_9$ |
| 238 | Cl | X | $CN_4H$ | single bond | H | $CH_3$ | $COCH_3$ |
| 239 | Cl | X | $CN_4H$ | single bond | H | $C_2H_5$ | $COCH_3$ |
| 240 | Cl | X | $CO_2H$ | *p-phenylene* | H | H | H |
| 241 | Cl | X | $CO_2H$ | single bond | H | $CH_3$ | H |
| 242 | Cl | X | $CO_2H$ | single bond | H | $C_2H_5$ | H |

TABLE VI-continued

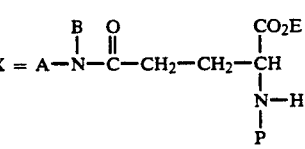

| Ex: # | R¹ | R² | R₅ | A | B | E | P |
|---|---|---|---|---|---|---|---|
| 243 | Cl | X | CN₄H | (p-phenylene) | H | H | H |
| 244 | Cl | X | CN₄H | single bond | H | CH₃ | H |
| 245 | Cl | X | CN₄H | single bond | H | C₂H₅ | H |
| 246 | Cl | X | CO₂H | —CH₂—(p-phenylene)— | H | H | COCH₃ |
| 247 | Cl | X | CO₂H | single bond | H | H | COCH₂Cl |
| 248 | Cl | X | CO₂H | single bond | H | H | COC₄H₉ |
| 249 | Cl | X | CO₂H | single bond | H | CH₃ | COCH₃ |
| 250 | Cl | X | CO₂H | single bond | H | C₂H₅ | COCH₃ |
| 251 | Cl | X | CN₄H | —CH₂—(p-phenylene)— | H | H | COCH₃ |
| 252 | Cl | X | CN₄H | single bond | H | H | COCH₂Cl |
| 253 | Cl | X | CN₄H | single bond | H | H | COC₄H₉ |
| 254 | Cl | X | CN₄H | single bond | H | CH₃ | COCH₃ |
| 255 | Cl | X | CN₄H | single bond | H | C₂H₅ | COCH₃ |
| 256 | Cl | X | CO₂H | —CH₂—(p-phenylene)— | H | H | H |
| 257 | Cl | X | CO₂H | single bond | H | CH₃ | H |
| 258 | Cl | X | CO₂H | single bond | H | C₂H₅ | H |
| 259 | Cl | X | CN₄H | —CH₂—(p-phenylene)— | H | H | H |
| 260 | Cl | X | CN₄H | single bond | H | CH₃ | H |
| 261 | Cl | X | CN₄H | single bond | H | C₂H₅ | H |
| 262 | Cl | X | CO₂H | (p-phenylene)—CH₂— | H | H | COCH₃ |
| 263 | Cl | X | CO₂H | single bond | H | H | COCH₂Cl |
| 264 | Cl | X | CO₂H | single bond | H | H | COC₄H₉ |
| 265 | Cl | X | CO₂H | single bond | H | CH₃ | COCH₃ |
| 266 | Cl | X | CO₂H | single bond | H | C₂H₅ | COCH₃ |

TABLE VI-continued

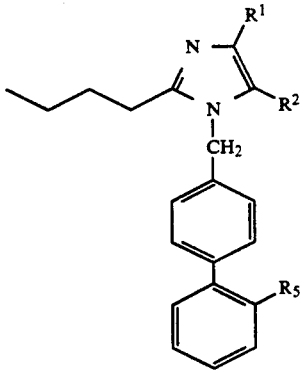

| Ex: # | R¹ | R² | R₅ | A | B | E | P |
|---|---|---|---|---|---|---|---|
| 267 | Cl | X | CN₄H | —⟨C₆H₄⟩—CH₂— | H | H | COCH₃ |
| 268 | Cl | X | CN₄H | single bond | H | H | COCH₂Cl |
| 269 | Cl | X | CN₄H | single bond | H | H | COC₄H₉ |
| 270 | Cl | X | CN₄H | single bond | H | CH₃ | COCH₃ |
| 271 | Cl | X | CN₄H | single bond | H | C₂H₅ | COCH₃ |
| 272 | Cl | X | CO₂H | —⟨C₆H₄⟩—CH₂— | H | H | H |
| 273 | Cl | X | CO₂H | single bond | H | CH₃ | H |
| 274 | Cl | X | CO₂H | single bond | H | C₂H₅ | H |
| 275 | Cl | X | CN₄H | —⟨C₆H₄⟩—CH₂— | H | H | H |
| 276 | Cl | X | CN₄H | single bond | H | CH₃ | H |
| 277 | Cl | X | CN₄H | single bond | H | C₂H₅ | H |
| 278 | Cl | X | CO₂H | —CH₂—⟨C₆H₄⟩—CH₂— | H | H | COCH₃ |
| 279 | Cl | X | CO₂H | single bond | H | H | COCH₂Cl |
| 280 | Cl | X | CO₂H | single bond | H | H | COC₄H₉ |
| 281 | Cl | X | CO₂H | single bond | H | CH₃ | COCH₃ |
| 282 | Cl | X | CO₂H | single bond | H | C₂H₅ | COCH₃ |
| 283 | Cl | X | CN₄H | —CH₂—⟨C₆H₄⟩—CH₂— | H | H | COCH₃ |
| 284 | Cl | X | CN₄H | single bond | H | H | COCH₂Cl |
| 285 | Cl | X | CN₄H | single bond | H | H | COC₄H₉ |
| 286 | Cl | X | CN₄H | single bond | H | CH₃ | COCH₃ |
| 287 | Cl | X | CN₄H | single bond | H | C₂H₅ | COCH₃ |
| 288 | Cl | X | CO₂H | —CH₂—⟨C₆H₄⟩—CH₂— | H | H | H |
| 289 | Cl | X | CO₂H | single bond | H | CH₃ | H |
| 290 | Cl | X | CO₂H | single bond | H | C₂H₅ | H |

TABLE VI-continued

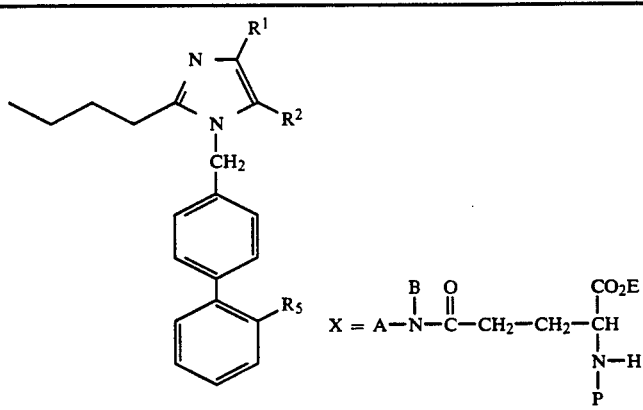

X = A—N(B)—C(=O)—CH₂—CH₂—CH(CO₂E)—N(P)—H

| Ex: # | R¹ | R² | R₅ | A | B | E | P |
|---|---|---|---|---|---|---|---|
| 291 | Cl | X | CN₄H | —CH₂—C₆H₄—CH₂— | H | H | H |
| 292 | Cl | X | CN₄H | single bond | H | CH₃ | H |
| 293 | Cl | X | CN₄H | single bond | H | C₂H₅ | H |
| 294 | Cl | X | CN₄H | —CH₂CH₂—C₆H₄— | H | H | COCH₃ |
| 295 | Cl | X | CO₂H | single bond | H | H | COCH₂Cl |
| 296 | Cl | X | CO₂H | single bond | H | H | COC₄H₉ |
| 297 | Cl | X | CO₂H | single bond | H | CH₃ | COCH₃ |
| 298 | Cl | X | CO₂H | single bond | H | C₂H₅ | COCH₃ |
| 299 | Cl | X | CN₄H | —CH₂CH₂—C₆H₄— | H | H | H |
| 300 | Cl | X | CN₄H | single bond | H | H | COCH₂Cl |
| 301 | Cl | X | CN₄H | single bond | H | COC₄H₉ |  |
| 302 | Cl | X | CN₄H | single bond | H | CH₃ | COCH₃ |
| 303 | Cl | X | CN₄H | single bond | H | C₂H₅ | COCH₃ |
| 304 | Cl | X | CN₄H | —C₆H₄—CH₂—CH₂— | H | H | COCH₃ |
| 305 | Cl | X | CO₂H | single bond | H | CH₃ | H |
| 306 | Cl | X | CO₂H | single bond | H | C₂H₅ | H |
| 307 | Cl | X | CN₄H | —C₆H₄—CH₂—CH₂— | H | H | H |
| 308 | Cl | X | CN₄H | single bond | H | CH₃ | H |
| 309 | Cl | X | CN₄H | single bond | H | C₂H₅ | H |
| 310 | Cl | X | CO₂H | cyclohexyl | H | H | COCH₃ |
| 311 | Cl | X | CO₂H | single bond | H | H | COCH₂Cl |
| 312 | Cl | X | CO₂H | single bond | H | H | COC₄H₉ |
| 313 | Cl | X | CO₂H | single bond | H | CH₃ | COCH₃ |
| 314 | Cl | X | CO₂H | single bond | H | C₂H₅ | COCH₃ |
| 315 | Cl | X | CN₄H | cyclohexyl | H | H | COCH₃ |

TABLE VI-continued $$X = A-N-\overset{B}{\underset{}{}}-\overset{O}{\underset{\|}{C}}-CH_2-CH_2-\overset{CO_2E}{\underset{\underset{P}{\overset{|}{N-H}}}{CH}}$$

| Ex: # | R¹ | R² | R₅ | A | B | E | P |
|---|---|---|---|---|---|---|---|
| 316 | Cl | X | CN₄H | single bond | H | H | COCH₂Cl |
| 317 | Cl | X | CN₄H | single bond | H | H | COC₄H₉ |
| 318 | Cl | X | CN₄H | single bond | H | CH₃ | COCH₃ |
| 319 | Cl | X | CN₄H | single bond | H | C₂H₅ | COCH₃ |
| 320 | Cl | X | CO₂H | cyclohexyl | H | H | H |
| 321 | Cl | X | CO₂H | single bond | H | CH₃ | H |
| 322 | Cl | X | CO₂H | single bond | H | C₂H₅ | H |
| 323 | Cl | X | CN₄H | cyclohexyl | H | H | H |
| 324 | Cl | X | CN₄H | single bond | H | CH₃ | H |
| 325 | Cl | X | CN₄H | single bond | H | C₂H₅ | H |
| 326 | Cl | X | CO₂H | —CH₂—cyclohexyl | H | H | COCH₃ |
| 327 | Cl | X | CO₂H | single bond | H | H | COCH₂Cl |
| 328 | Cl | X | CO₂H | single bond | H | H | COC₄H₉ |
| 329 | Cl | X | CO₂H | single bond | H | CH₃ | COCH₃ |
| 330 | Cl | X | CO₂H | single bond | H | C₂H₅ | COCH₃ |
| 331 | Cl | X | CN₄H | —CH₂—cyclohexyl | H | H | COCH₃ |
| 332 | Cl | X | CN₄H | single bond | H | H | COCH₂Cl |
| 333 | Cl | X | CN₄H | single bond | H | H | COC₄H₉ |
| 334 | Cl | X | CN₄H | single bond | H | CH₃ | COCH₃ |
| 335 | Cl | X | CN₄H | single bond | H | C₂H₅ | COCH₃ |
| 336 | Cl | X | CO₂H | —CH₂—cyclohexyl | H | H | H |
| 337 | Cl | X | CO₂H | single bond | H | CH₃ | H |
| 338 | Cl | X | CO₂H | single bond | H | C₂H₅ | H |
| 339 | Cl | X | CN₄H | —CH₂—cyclohexyl | H | H | H |
| 340 | Cl | X | CN₄H | single bond | H | CH₃ | H |
| 341 | Cl | X | CN₄H | single bond | H | C₂H₅ | H |
| 342 | Cl | X | CO₂H | cyclohexyl—CH₂— | H | H | COCH₃ |
| 343 | Cl | X | CO₂H | single bond | H | H | COCH₂Cl |
| 344 | Cl | X | CO₂H | single bond | H | H | COC₄H₉ |
| 345 | Cl | X | CO₂H | single bond | H | CH₃ | COCH₃ |

TABLE VI-continued $$X = A-N-\overset{\overset{\displaystyle B}{|}}{\underset{}{N}}-\overset{\overset{\displaystyle O}{\|}}{C}-CH_2-CH_2-\overset{\overset{\displaystyle CO_2E}{|}}{\underset{\underset{\displaystyle P}{|}}{\underset{\displaystyle N-H}{CH}}}$$

| Ex: # | R¹ | R² | R₅ | A | B | E | P |
|---|---|---|---|---|---|---|---|
| 346 | Cl | X | CO₂H | single bond | H | C₂H₅ | COCH₃ |
| 347 | Cl | X | CN₄H | ⌬-CH₂— | H | H | COCH₃ |
| 348 | Cl | X | CN₄H | single bond | H | H | COCH₂Cl |
| 349 | Cl | X | CN₄H | single bond | H | H | COC₄H₉ |
| 350 | Cl | X | CN₄H | single bond | H | CH₃ | COCH₃ |
| 351 | Cl | X | CN₄H | single bond | H | C₂H₅ | COCH₃ |
| 352 | Cl | X | CO₂H | ⌬-CH₂— | H | H | H |
| 353 | Cl | X | CO₂H | single bond | H | CH₃ | H |
| 354 | Cl | X | CO₂H | single bond | H | C₂H₅ | H |
| 355 | Cl | X | CN₄H | ⌬-CH₂— | H | H | H |
| 356 | Cl | X | CN₄H | single bond | H | CH₃ | H |
| 357 | Cl | X | CN₄H | single bond | H | C₂H₅ | H |
| 358 | Cl | X | CO₂H | —CH₂-⌬-CH₂— | H | H | COCH₃ |
| 359 | Cl | X | CO₂H | single bond | H | H | COCH₂Cl |
| 360 | Cl | X | CO₂H | single bond | H | H | COC₄H₉ |
| 361 | Cl | X | CO₂H | single bond | H | CH₃ | COCH₃ |
| 362 | Cl | X | CO₂H | single bond | H | C₂H₅ | COCH₃ |
| 363 | Cl | X | CN₄H | —CH₂-⌬-CH₂— | H | H | COCH₃ |
| 364 | Cl | X | CN₄H | single bond | H | H | COCH₂Cl |
| 365 | Cl | X | CN₄H | single bond | H | H | COC₄H₉ |
| 366 | Cl | X | CN₄H | single bond | H | CH₃ | COCH₃ |
| 367 | Cl | X | CN₄H | single bond | H | C₂H₅ | COCH₃ |
| 368 | Cl | X | CO₂H | —CH₂-⌬-CH₂— | H | H | H |
| 369 | Cl | X | CO₂H | single bond | H | CH₃ | H |
| 370 | Cl | X | CO₂H | single bond | H | C₂H₅ | H |
| 371 | Cl | X | CN₄H | —CH₂-⌬-CH₂— | H | H | H |
| 372 | Cl | X | CN₄H | single bond | H | CH₃ | H |
| 373 | Cl | X | CN₄H | single bond | H | C₂H₅ | H |

TABLE VI-continued

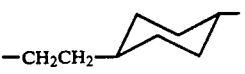

X = A—N(B)—C(=O)—CH2—CH2—CH(CO2E)—N(P)—H

| Ex: # | R¹ | R² | R₅ | A | B | E | P |
|---|---|---|---|---|---|---|---|
| 374 | Cl | X | CN₄H | —CH₂CH₂—(cyclohexyl) | H | H | COCH₃ |
| 375 | Cl | X | CO₂H | single bond | H | H | COCH₂Cl |
| 376 | Cl | X | CO₂H | single bond | H | H | COC₄H₉ |
| 377 | Cl | X | CO₂H | single bond | H | CH₃ | COCH₃ |
| 378 | Cl | X | CO₂H | single bond | H | C₂H₅ | COCH₃ |
| 379 | Cl | X | CN₄H | —CH₂CH₂—(cyclohexyl) | H | H | H |
| 380 | Cl | X | CN₄H | single bond | H | H | COCH₂Cl |
| 381 | Cl | X | CN₄H | single bond | H | H | COC₄H₉ |
| 382 | Cl | X | CN₄H | single bond | H | CH₃ | COCH₃ |
| 383 | Cl | X | CN₄H | single bond | H | C₂H₅ | COCH₃ |
| 384 | Cl | X | CN₄H | (cyclohexyl)—CH₂CH₂— | H | H | COCH₃ |
| 385 | Cl | X | CO₂H | single bond | H | CH₃ | H |
| 386 | Cl | X | CO₂H | single bond | H | C₂H₅ | H |
| 387 | Cl | X | CN₄H | (cyclohexyl)—CH₂CH₂— | H | H | H |
| 388 | Cl | X | CN₄H | single bond | H | CH₃ | H |
| 389 | Cl | X | CN₄H | single bond | H | C₂H₅ | H |
| 390 | Cl | X | CN₄H | (piperidinyl)N— | * | H | COCH₃ |
| 391 | Cl | X | CO₂H | single bond | H | H | COCH₂Cl |
| 392 | Cl | X | CO₂H | single bond | H | H | COC₄H₉ |
| 393 | Cl | X | CO₂H | single bond | H | CH₃ | COCH₃ |
| 394 | Cl | X | CO₂H | single bond | H | C₂H₅ | COCH₃ |
| 395 | Cl | X | CN₄H | (piperidinyl)N— | * | H | H |
| 396 | Cl | X | CN₄H | single bond | H | H | COCH₂Cl |
| 397 | Cl | X | CN₄H | single bond | H | H | COC₄H₉ |
| 398 | Cl | X | CN₄H | single bond | H | CH₃ | COCH₃ |
| 399 | Cl | X | CN₄H | single bond | H | C₂H₅ | COCH₃ |
| 400 | Cl | X | CN₄H | —CH₂—(piperidinyl)N— | * | H | COCH₃ |
| 401 | Cl | X | CO₂H | single bond | H | CH₃ | H |
| 402 | Cl | X | CO₂H | single bond | H | C₂H₅ | H |

TABLE VI-continued $$X = A-N(B)-C(=O)-CH_2-CH_2-CH(CO_2E)-N(H)(P)$$

| Ex: # | R¹ | R² | R₅ | A | B | E | P |
|---|---|---|---|---|---|---|---|
| 403 | Cl | X | CN₄H | —CH₂—(cyclohexyl)—N— | * | H | H |
| 404 | Cl | X | CN₄H | single bond | H | CH₃ | H |
| 405 | Cl | X | CN₄H | single bond | H | C₂H₅ | H |
| 406 | Cl | X | CN₄H | —CH₂—CH₂—(cyclohexyl)—N— | * | H | COCH₃ |
| 407 | Cl | X | CO₂H | single bond | H | H | COCH₂Cl |
| 408 | Cl | X | CO₂H | single bond | H | H | COC₄H₉ |
| 409 | Cl | X | CO₂H | single bond | H | CH₃ | COCH₃ |
| 410 | Cl | X | CO₂H | single bond | H | C₂H₅ | COCH₃ |
| 411 | Cl | X | CN₄H | —CH₂—CH₂—(cyclohexyl)—N— | * | H | H |
| 412 | Cl | X | CN₄H | single bond | H | H | COCH₂Cl |
| 413 | Cl | X | CN₄H | single bond | H | H | COC₄H₉ |
| 414 | Cl | X | CN₄H | single bond | H | CH₃ | COCH₃ |
| 415 | Cl | X | CN₄H | single bond | H | C₂H₅ | COCH₃ |
| 416 | Cl | X | CN₄H | —CH₂—N(piperidine)— | * | H | COCH₃ |
| 417 | Cl | X | CO₂H | single bond | H | CH₃ | H |
| 418 | Cl | X | CO₂H | single bond | H | C₂H₅ | H |
| 419 | Cl | X | CN₄H | —CH₂—N(piperidine)— | * | H | H |
| 420 | Cl | X | CN₄H | single bond | H | CH₃ | H |
| 421 | Cl | X | CN₄H | single bond | H | C₂H₅ | H |
| 422 | Cl | X | CN₄H | —CH₂—CH₂—N(piperidine)— | * | H | COCH₃ |
| 423 | Cl | X | CN₄H | single bond | H | H | COCH₂Cl |
| 424 | Cl | X | CN₄H | single bond | H | H | COC₄H₉ |
| 425 | Cl | X | CN₄H | single bond | H | CH₃ | COCH₃ |
| 426 | Cl | X | CN₄H | single bond | H | C₂H₅ | COCH₃ |
| 427 | Cl | X | CN₄H | —CH₂CH₂—N(piperidine)— | * | H | H |
| 428 | Cl | X | CN₄H | single bond | H | CH₃ | H |
| 429 | Cl | X | CN₄H | single bond | H | C₂H₅ | H |
| 430 | X | Cl | CO₂H | single bond | H | H | COCH₃ |
| 431 | X | Cl | CO₂H | single bond | H | H | COCH₂Cl |
| 432 | X | Cl | CO₂H | single bond | H | H | COC₄H₉ |
| 433 | X | Cl | CO₂H | single bond | H | CH₃ | COCH₃ |

TABLE VI-continued

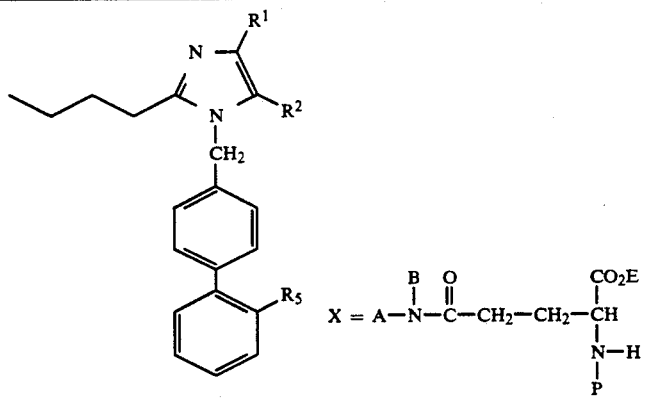

$$X = A-N(B)-C(=O)-CH_2-CH_2-CH(CO_2E)-N(H)-P$$

| Ex: # | $R^1$ | $R^2$ | $R_5$ | A | B | E | P |
|---|---|---|---|---|---|---|---|
| 434 | X | Cl | $CO_2H$ | single bond | H | $C_2H_5$ | $COCH_3$ |
| 435 | X | Cl | $CN_4H$ | single bond | H | H | $COCH_3$ |
| 436 | X | Cl | $CN_4H$ | single bond | H | H | $COCH_2Cl$ |
| 437 | X | Cl | $CN_4H$ | single bond | H | H | $COC_4H_9$ |
| 438 | X | Cl | $CN_4H$ | single bond | H | $CH_3$ | $COCH_3$ |
| 439 | X | Cl | $CN_4H$ | single bond | H | $C_2H_5$ | $COCH_3$ |
| 440 | X | Cl | $CO_2H$ | single bond | H | H | H |
| 441 | X | Cl | $CO_2H$ | single bond | H | $CH_3$ | H |
| 442 | X | Cl | $CO_2H$ | single bond | H | $C_2H_5$ | H |
| 443 | X | Cl | $CN_4H$ | single bond | H | H | H |
| 444 | X | Cl | $CN_4H$ | single bond | H | $CH_3$ | H |
| 445 | X | Cl | $CN_4H$ | single bond | H | $C_2H_5$ | H |
| 446 | X | Cl | $CO_2H$ | $-CH_2-$ | H | H | $COCH_3$ |
| 447 | X | Cl | $CO_2H$ | single bond | H | H | $COCH_2Cl$ |
| 448 | X | Cl | $CO_2H$ | single bond | H | H | $COC_4H_9$ |
| 449 | X | Cl | $CO_2H$ | single bond | H | $CH_3$ | $COCH_3$ |
| 450 | X | Cl | $CO_2H$ | single bond | H | $C_2H_5$ | $COCH_3$ |
| 451 | X | Cl | $CN_4H$ | single bond | H | H | $COCH_2Cl$ |
| 452 | X | Cl | $CN_4H$ | single bond | H | H | $COC_4H_9$ |
| 453 | X | Cl | $CN_4H$ | single bond | H | $CH_3$ | $COCH_3$ |
| 454 | X | Cl | $CN_4H$ | single bond | H | $C_2H_5$ | $COCH_3$ |
| 455 | X | Cl | $CO_2H$ | $-CH_2-$ | H | H | H |
| 456 | X | Cl | $CO_2H$ | single bond | H | $CH_3$ | H |
| 457 | X | Cl | $CO_2H$ | single bond | H | $C_2H_5$ | H |
| 458 | X | Cl | $CN_4H$ | $-CH_2-$ | H | H | H |
| 459 | X | Cl | $CN_4H$ | single bond | H | $CH_3$ | H |
| 460 | X | Cl | $CN_4H$ | single bond | H | $C_2H_5$ | H |
| 461 | X | Cl | $CN_4H$ | $-CH_2-$ | $CH_3$ | H | H |
| 462 | X | Cl | $CN_4H$ | $-CH_2-$ | $CH_3$ | H | $COCH_3$ |
| 463 | X | Cl | $CO_2H$ | $-CH_2CH_2-$ | H | H | $COCH_3$ |
| 464 | X | Cl | $CO_2H$ | single bond | H | H | $COCH_2Cl$ |
| 465 | X | Cl | $CO_2H$ | single bond | H | H | $COC_4H_9$ |
| 466 | X | Cl | $CO_2H$ | single bond | H | $CH_3$ | $COCH_3$ |
| 467 | X | Cl | $CO_2H$ | single bond | H | $C_2H_5$ | $COCH_3$ |
| 468 | X | Cl | $CN_4H$ | $-CH_2CH_2-$ | H | H | $COCH_3$ |
| 469 | X | Cl | $CN_4H$ | single bond | H | H | $COCH_2Cl$ |
| 470 | X | Cl | $CN_4H$ | single bond | H | H | $COC_4H_9$ |
| 471 | X | Cl | $CN_4H$ | single bond | H | $CH_3$ | $COCH_3$ |
| 472 | X | Cl | $CN_4H$ | single bond | H | $C_2H_5$ | $COCH_3$ |
| 473 | X | Cl | $CO_2H$ | $-CH_2CH_2-$ | H | H | H |
| 474 | X | Cl | $CO_2H$ | single bond | H | $CH_3$ | H |
| 475 | X | Cl | $CO_2H$ | single bond | H | $C_2H_5$ | H |
| 476 | X | Cl | $CO_2H$ | $-CH_2CH_2-$ | H | H | H |
| 477 | X | Cl | $CN_4H$ | single bond | H | $CH_3$ | H |
| 478 | X | Cl | $CN_4H$ | single bond | H | $C_2H_5$ | H |
| 479 | X | Cl | $CO_2H$ | $C_3H_6(n)$ | H | H | $COCH_3$ |
| 480 | X | Cl | $CO_2H$ | single bond | H | H | $COCH_2Cl$ |
| 481 | X | Cl | $CO_2H$ | single bond | H | H | $COC_4H_9$ |
| 482 | X | Cl | $CO_2H$ | single bond | H | $CH_3$ | $COCH_3$ |
| 483 | X | Cl | $CO_2H$ | single bond | H | $C_2H_5$ | $COCH_3$ |
| 484 | X | Cl | $CN_4H$ | $C_3H_6(n)$ | H | H | $COCH_3$ |
| 485 | X | Cl | $CN_4H$ | single bond | H | H | $COCH_2Cl$ |
| 486 | X | Cl | $CN_4H$ | single bond | H | H | $COC_4H_9$ |
| 487 | X | Cl | $CN_4H$ | single bond | H | $CH_3$ | $COCH_3$ |
| 488 | X | Cl | $CN_4H$ | single bond | H | $C_2H_5$ | $COCH_3$ |
| 489 | X | Cl | $CO_2H$ | $C_3H_6(n)$ | H | H | H |
| 490 | X | Cl | $CO_2H$ | single bond | H | $CH_3$ | H |
| 491 | X | Cl | $CO_2H$ | single bond | H | $C_2H_5$ | H |
| 492 | X | Cl | $CN_4H$ | $C_3H_6(n)$ | H | H | H |
| 493 | X | Cl | $CN_4H$ | single bond | H | $CH_3$ | H |
| 494 | X | Cl | $CN_4H$ | single bond | H | $C_2H_5$ | H |

TABLE VI-continued

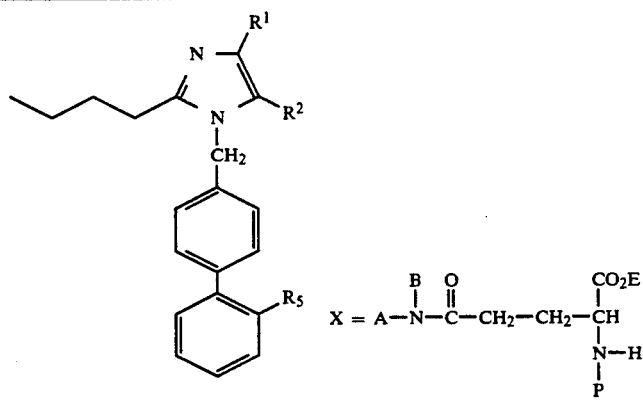

| Ex: # | R¹ | R² | R₅ | A | B | E | P |
|---|---|---|---|---|---|---|---|
| 495 | X | Cl | $CO_2H$ | $C_4H_8(n)$ | H | H | $COCH_3$ |
| 496 | X | Cl | $CO_2H$ | single bond | H | H | $COCH_2Cl$ |
| 497 | X | Cl | $CO_2H$ | single bond | H | H | $COC_4H_9$ |
| 498 | X | Cl | $CO_2H$ | single bond | H | $CH_3$ | $COCH_3$ |
| 499 | X | Cl | $CO_2H$ | single bond | H | $C_2H_5$ | $COCH_3$ |
| 500 | X | Cl | $CN_4H$ | $C_4H_8(n)$ | H | H | $COCH_3$ |
| 501 | X | Cl | $CN_4H$ | single bond | H | H | $COCH_2Cl$ |
| 502 | X | Cl | $CN_4H$ | single bond | H | H | $COC_4H_9$ |
| 503 | X | Cl | $CN_4H$ | single bond | H | $CH_3$ | $COCH_3$ |
| 504 | X | Cl | $CN_4H$ | single bond | H | $C_2H_5$ | $COCH_3$ |
| 505 | X | Cl | $CO_2H$ | $C_4H_8(n)$ | H | H | H |
| 506 | X | Cl | $CO_2H$ | single bond | H | $CH_3$ | H |
| 507 | X | Cl | $CO_2H$ | single bond | H | $C_2H_5$ | H |
| 508 | X | Cl | $CN_4H$ | $C_4H_8(n)$ | H | H | H |
| 509 | X | Cl | $CN_4H$ | single bond | H | $CH_3$ | H |
| 510 | X | Cl | $CN_4H$ | single bond | H | $C_2H_5$ | H |
| 511 | X | Cl | $CO_2H$ | ⟨phenylene⟩ | H | H | $COCH_3$ |
| 512 | X | Cl | $CO_2H$ | single bond | H | H | $COCH_2Cl$ |
| 513 | X | Cl | $CO_2H$ | single bond | H | H | $COC_4H_9$ |
| 514 | X | Cl | $CO_2H$ | single bond | H | $CH_3$ | $COCH_3$ |
| 515 | X | Cl | $CO_2H$ | single bond | H | $C_2H_5$ | $COCH_3$ |
| 516 | X | Cl | $CN_4H$ | ⟨phenylene⟩ | H | H | $COCH_3$ |
| 517 | X | Cl | $CN_4H$ | single bond | H | H | $COCH_2Cl$ |
| 518 | X | Cl | $CN_4H$ | single bond | H | H | $COC_4H_9$ |
| 519 | X | Cl | $CN_4H$ | single bond | H | $CH_3$ | $COCH_3$ |
| 520 | X | Cl | $CN_4H$ | single bond | H | $C_2H_5$ | $COCH_3$ |
| 521 | X | Cl | $CO_2H$ | ⟨phenylene⟩ | H | H | H |
| 522 | X | Cl | $CO_2H$ | single bond | H | $CH_3$ | H |
| 523 | X | Cl | $CO_2H$ | single bond | H | $C_2H_5$ | H |
| 524 | X | Cl | $CN_4H$ | ⟨phenylene⟩ | H | H | H |
| 525 | X | Cl | $CN_4H$ | single bond | H | $CH_3$ | H |
| 526 | X | Cl | $CN_4H$ | single bond | H | $C_2H_5$ | H |

TABLE VI-continued

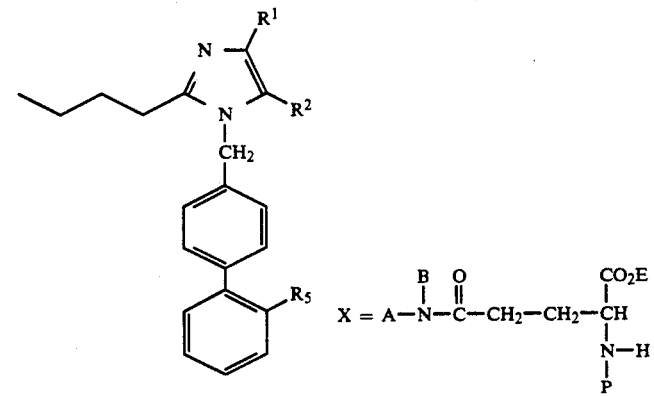

| Ex: # | R¹ | R² | R₅ | A | B | E | P |
|---|---|---|---|---|---|---|---|
| 527 | X | Cl | $CO_2H$ | —CH₂—⟨C₆H₄⟩— | H | H | $COCH_3$ |
| 528 | X | Cl | $CO_2H$ | single bond | H | H | $COCH_2Cl$ |
| 529 | X | Cl | $CO_2H$ | single bond | H | H | $COC_4H_9$ |
| 530 | X | Cl | $CO_2H$ | single bond | H | $CH_3$ | $COCH_3$ |
| 531 | X | Cl | $CO_2H$ | single bond | H | $C_2H_5$ | $COCH_3$ |
| 532 | X | Cl | $CN_4H$ | —CH₂—⟨C₆H₄⟩— | H | H | $COCH_3$ |
| 533 | X | Cl | $CN_4H$ | single bond | H | H | $COCH_2Cl$ |
| 534 | X | Cl | $CN_4H$ | single bond | H | H | $COC_4H_9$ |
| 535 | X | Cl | $CN_4H$ | single bond | H | $CH_3$ | $COCH_3$ |
| 536 | X | Cl | $CN_4H$ | single bond | H | $C_2H_5$ | $COCH_3$ |
| 537 | X | Cl | $CO_2H$ | —CH₂—⟨C₆H₄⟩— | H | H | H |
| 538 | X | Cl | $CO_2H$ | single bond | H | $CH_3$ | H |
| 539 | X | Cl | $CO_2H$ | single bond | H | $C_2H_5$ | H |
| 540 | X | Cl | $CN_4H$ | —CH₂—⟨C₆H₄⟩— | H | H | H |
| 541 | X | Cl | $CN_4H$ | single bond | H | $CH_3$ | H |
| 542 | X | Cl | $CN_4H$ | single bond | H | $C_2H_5$ | H |
| 543 | X | Cl | $CO_2H$ | —⟨C₆H₄⟩—CH₂— | H | H | $COCH_3$ |
| 544 | X | Cl | $CO_2H$ | single bond | H | H | $COCH_2Cl$ |
| 545 | X | Cl | $CO_2H$ | single bond | H | H | $COC_4H_9$ |
| 546 | X | Cl | $CO_2H$ | single bond | H | $CH_3$ | $COCH_3$ |
| 547 | X | Cl | $CO_2H$ | single bond | H | $C_2H_5$ | $COCH_3$ |
| 548 | X | Cl | $CN_4H$ | —⟨C₆H₄⟩—CH₂— | H | H | $\overline{COCH_3}$ |
| 549 | X | Cl | $CN_4H$ | single bond | H | H | $COCH_2Cl$ |
| 550 | X | Cl | $CN_4H$ | single bond | H | H | $COC_4H_9$ |
| 551 | X | Cl | $CN_4H$ | single bond | H | $CH_3$ | $COCH_3$ |
| 552 | X | Cl | $CN_4H$ | single bond | H | $C_2H_5$ | $COCH_3$ |

TABLE VI-continued $$X = A-\overset{B}{N}-\overset{O}{\overset{\|}{C}}-CH_2-CH_2-\overset{CO_2E}{\overset{|}{CH}}$$
$$\overset{|}{\underset{P}{N-H}}$$

| Ex: # | R¹ | R² | R₅ | A | B | E | P |
|---|---|---|---|---|---|---|---|
| 553 | X | Cl | CO₂H | —⟨C₆H₄⟩—CH₂— | H | H | H |
| 554 | X | Cl | CO₂H | single bond | H | CH₃ | H |
| 555 | X | Cl | CO₂H | single bond | H | C₂H₅ | H |
| 556 | X | Cl | CN₄H | —⟨C₆H₄⟩—CH₂— | H | H | H |
| 557 | X | Cl | CN₄H | single bond | H | CH₃ | H |
| 558 | X | Cl | CN₄H | single bond | H | C₂H₅ | H |
| 559 | X | Cl | CO₂H | —CH₂—⟨C₆H₄⟩—CH₂— | H | H | COCH₃ |
| 560 | X | Cl | CO₂H | single bond | H | H | COCH₂Cl |
| 561 | X | Cl | CO₂H | single bond | H | H | COC₄H₉ |
| 562 | X | Cl | CO₂H | single bond | H | CH₃ | COCH₃ |
| 563 | X | Cl | CO₂H | single bond | H | C₂H₅ | COCH₃ |
| 564 | X | Cl | CN₄H | —CH₂—⟨C₆H₄⟩—CH₂— | H | H | COCH₃ |
| 565 | X | Cl | CN₄H | single bond | H | H | COCH₂Cl |
| 566 | X | Cl | CN₄H | single bond | H | H | COC₄H₉ |
| 567 | X | Cl | CN₄H | single bond | H | CH₃ | COCH₃ |
| 568 | X | Cl | CN₄H | single bond | H | C₂H₅ | COCH₃ |
| 569 | X | Cl | CO₂H | —CH₂—⟨C₆H₄⟩—CH₂— | H | H | H |
| 570 | X | Cl | CO₂H | single bond | H | CH₃ | H |
| 571 | X | Cl | CO₂H | single bond | H | C₂H₅ | H |
| 572 | X | Cl | CN₄H | —CH₂—⟨C₆H₄⟩—CH₂— | H | H | H |
| 573 | X | Cl | CN₄H | single bond | H | CH₃ | H |
| 574 | X | Cl | CN₄H | single bond | H | C₂H₅ | H |

TABLE VI-continued

[Structure diagram showing an imidazole ring with butyl group, R¹, R², and connected to a biphenyl group with R₅ substituent, and CH₂ linker. Below: X = A—N(B)—C(=O)—CH₂—CH₂—CH(CO₂E)(NH—P)]

| Ex: # | R¹ | R² | R₅ | A | B | E | P |
|---|---|---|---|---|---|---|---|
| 575 | X | Cl | CN₄H | —CH₂CH₂—(p-C₆H₄)— | H | H | COCH₃ |
| 576 | X | Cl | CO₂H | single bond | H | H | COCH₂Cl |
| 577 | X | Cl | CO₂H | single bond | H | H | COC₄H₉ |
| 578 | X | Cl | CO₂H | single bond | H | CH₃ | COCH₃ |
| 579 | X | Cl | CO₂H | single bond | H | C₂H₅ | COCH₃ |
| 580 | X | Cl | CN₄H | —CH₂CH₂—(p-C₆H₄)— | H | H | H |
| 581 | X | Cl | CN₄H | single bond | H | H | COCH₂Cl |
| 582 | X | Cl | CN₄H | single bond | H | H | COC₄H₉ |
| 583 | X | Cl | CN₄H | single bond | H | CH₃ | COCH₃ |
| 584 | X | Cl | CN₄H | single bond | H | C₂H₅ | COCH₃ |
| 585 | X | Cl | CN₄H | —(p-C₆H₄)—CH₂—CH₂— | H | H | COCH₃ |
| 586 | X | Cl | CO₂H | single bond | H | CH₃ | H |
| 587 | X | Cl | CO₂H | single bond | H | C₂H₅ | H |
| 588 | X | Cl | CN₄H | —(p-C₆H₄)—CH₂—CH₂— | H | H | H |
| 589 | X | Cl | CN₄H | single bond | H | CH₃ | H |
| 590 | X | Cl | CN₄H | single bond | H | C₂H₅ | H |
| 591 | X | Cl | CO₂H | cyclohexylene | H | H | COCH₃ |
| 592 | X | Cl | CO₂H | single bond | H | H | COCH₂Cl |
| 593 | X | Cl | CO₂H | single bond | H | H | COC₄H₉ |
| 594 | X | Cl | CO₂H | single bond | H | CH₃ | COCH₃ |
| 595 | X | Cl | CO₂H | single bond | H | C₂H₅ | COCH₃ |
| 596 | X | Cl | CN₄H | cyclohexylene | H | H | COCH₃ |
| 597 | X | Cl | CN₄H | single bond | H | H | COCH₂Cl |
| 598 | X | Cl | CN₄H | single bond | H | H | COC₄H₉ |
| 599 | X | Cl | CN₄H | single bond | H | CH₃ | COCH₃ |
| 600 | X | Cl | CN₄H | single bond | H | C₂H₅ | COCH₃ |
| 601 | X | Cl | CO₂H | cyclohexylene | H | H | H |

TABLE VI-continued

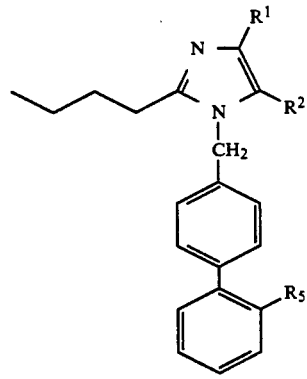

$$X = A-\overset{B}{N}-\overset{O}{\underset{\|}{C}}-CH_2-CH_2-\overset{CO_2E}{\underset{\underset{P}{\overset{|}{N-H}}}{CH}}$$

| Ex: # | R¹ | R² | R₅ | A | B | E | P |
|---|---|---|---|---|---|---|---|
| 602 | X | Cl | CO₂H | single bond | H | CH₃ | H |
| 603 | X | Cl | CO₂H | single bond | H | C₂H₅ | H |
| 604 | X | Cl | CN₄H | 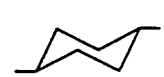 | H | H | H |
| 605 | X | Cl | CN₄H | single bond | H | CH₃ | H |
| 606 | X | Cl | CN₄H | single bond | H | C₂H₅ | H |
| 607 | X | Cl | CO₂H | —CH₂— | H | H | COCH₃ |
| 608 | X | Cl | CO₂H | single bond | H | H | COCH₂Cl |
| 609 | X | Cl | CO₂H | single bond | H | H | COC₄H₉ |
| 610 | X | Cl | CO₂H | single bond | H | CH₃ | COCH₃ |
| 611 | X | Cl | CO₂H | single bond | H | C₂H₅ | COCH₃ |
| 612 | X | Cl | CN₄H | —CH₂— | H | H | COCH₃ |
| 613 | X | Cl | CN₄H | single bond | H | H | COCH₂Cl |
| 614 | X | Cl | CN₄H | single bond | H | H | COC₄H₉ |
| 615 | X | Cl | CN₄H | single bond | H | CH₃ | COCH₃ |
| 616 | X | Cl | CN₄H | single bond | H | C₂H₅ | COCH₃ |
| 617 | X | Cl | CO₂H | —CH₂— | H | H | H |
| 618 | X | Cl | CO₂H | single bond | H | CH₃ | H |
| 619 | X | Cl | CO₂H | single bond | H | C₂H₅ | H |
| 620 | X | Cl | CN₄H | —CH₂—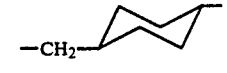 | H | H | H |
| 621 | X | Cl | CN₄H | single bond | H | CH₃ | H |
| 622 | X | Cl | CN₄H | single bond | H | C₂H₅ | H |
| 623 | X | Cl | CO₂H | —CH₂— | H | H | COCH₃ |
| 624 | X | Cl | CO₂H | single bond | H | H | COCH₂Cl |
| 625 | X | Cl | CO₂H | single bond | H | H | COC₄H₉ |
| 626 | X | Cl | CO₂H | single bond | H | CH₃ | COCH₃ |
| 627 | X | Cl | CO₂H | single bond | H | C₂H₅ | COCH₃ |
| 628 | X | Cl | CN₄H | —CH₂— | H | H | COCH₃ |
| 629 | X | Cl | CN₄H | single bond | H | H | COCH₂Cl |
| 630 | X | Cl | CN₄H | single bond | H | H | COC₄H₉ |
| 631 | X | Cl | CN₄H | single bond | H | CH₃ | COCH₃ |

TABLE VI-continued

[Structure diagram: 2-butyl-imidazole with R¹, R² substituents, N-CH₂-biphenyl with R₅ substituent; X = A—N(B)—C(=O)—CH₂—CH₂—CH(CO₂E)(NH-P)]

| Ex: # | R¹ | R² | R₅ | A | B | E | P |
|---|---|---|---|---|---|---|---|
| 632 | X | Cl | CN₄H | single bond | H | C₂H₅ | COCH₃ |
| 633 | X | Cl | CO₂H | —⟨cyclohexyl⟩—CH₂— | H | H | H |
| 634 | X | Cl | CO₂H | single bond | H | CH₃ | H |
| 635 | X | Cl | CO₂H | single bond | H | C₂H₅ | H |
| 636 | X | Cl | CN₄H | —⟨cyclohexyl⟩—CH₂— | H | H | H |
| 637 | X | Cl | CN₄H | single bond | H | CH₃ | H |
| 638 | X | Cl | CN₄H | single bond | H | C₂H₅ | H |
| 639 | X | Cl | CO₂H | —CH₂—⟨cyclohexyl⟩—CH₂— | H | H | COCH₃ |
| 640 | X | Cl | CO₂H | single bond | H | H | COCH₂Cl |
| 641 | X | Cl | CO₂H | single bond | H | H | COC₄H₉ |
| 642 | X | Cl | CO₂H | single bond | H | CH₃ | COCH₃ |
| 643 | X | Cl | CO₂H | single bond | H | C₂H₅ | COCH₃ |
| 644 | X | Cl | CN₄H | —CH₂—⟨cyclohexyl⟩—CH₂— | H | H | COCH₃ |
| 645 | X | Cl | CN₄H | single bond | H | H | COCH₂Cl |
| 646 | X | Cl | CN₄H | single bond | H | H | COC₄H₉ |
| 647 | X | Cl | CN₄H | single bond | H | CH₃ | COCH₃ |
| 648 | X | Cl | CN₄H | single bond | H | C₂H₅ | COCH₃ |
| 649 | X | Cl | CO₂H | —CH₂—⟨cyclohexyl⟩—CH₂— | H | H | H |
| 650 | X | Cl | CO₂H | single bond | H | CH₃ | H |
| 651 | X | Cl | CO₂H | single bond | H | C₂H₅ | H |
| 652 | X | Cl | CN₄H | —CH₂—⟨cyclohexyl⟩—CH₂— | H | H | H |
| 653 | X | Cl | CN₄H | single bond | H | CH₃ | H |
| 654 | X | Cl | CN₄H | single bond | H | C₂H₅ | H |
| 655 | X | Cl | CN₄H | —CH₂CH₂—⟨cyclohexyl⟩— | H | H | COCH₃ |
| 656 | X | Cl | CO₂H | single bond | H | H | COCH₂Cl |
| 657 | X | Cl | CO₂H | single bond | H | H | COC₄H₉ |
| 658 | X | Cl | CO₂H | single bond | H | CH₃ | COCH₃ |
| 659 | X | Cl | CO₂H | single bond | H | C₂H₅ | COCH₃ |

TABLE VI-continued $$X = A-N(B)-C(=O)-CH_2-CH_2-CH(CO_2E)-N(H)(P)$$

| Ex: # | R¹ | R² | R₅ | A | B | E | P |
|---|---|---|---|---|---|---|---|
| 660 | X | Cl | CN₄H | —CH₂CH₂—(cyclohexyl) | H | H | H |
| 661 | X | Cl | CN₄H | single bond | H | H | COCH₂Cl |
| 662 | X | Cl | CN₄H | single bond | H | H | COC₄H₉ |
| 663 | X | Cl | CN₄H | single bond | H | CH₃ | COCH₃ |
| 664 | X | Cl | CN₄H | single bond | H | C₂H₅ | COCH₃ |
| 665 | X | Cl | CN₄H | (cyclohexyl)—CH₂CH₂— | H | H | COCH₃ |
| 666 | X | Cl | CO₂H | single bond | H | CH₃ | H |
| 667 | X | Cl | CO₂H | single bond | H | C₂H₅ | H |
| 668 | X | Cl | CN₄H | (cyclohexyl)—CH₂CH₂— | H | H | H |
| 669 | X | Cl | CN₄H | single bond | H | CH₃ | H |
| 670 | X | Cl | CN₄H | single bond | H | C₂H₅ | H |
| 671 | X | Cl | CN₄H | (cyclohexyl)N— | * | H | COCH₃ |
| 672 | X | Cl | CO₂H | single bond | H | H | COCH₂Cl |
| 673 | X | Cl | CO₂H | single bond | H | H | COC₄H₉ |
| 674 | X | Cl | CO₂H | single bond | H | CH₃ | COCH₃ |
| 675 | X | Cl | CO₂H | single bond | H | C₂H₅ | COCH₃ |
| 676 | X | Cl | CN₄H | (cyclohexyl)N— | * | H | H |
| 677 | X | Cl | CN₄H | single bond | H | H | COCH₂Cl |
| 678 | X | Cl | CN₄H | single bond | H | H | COC₄H₉ |
| 679 | X | Cl | CN₄H | single bond | H | CH₃ | COCH₃ |
| 680 | X | Cl | CN₄H | single bond | H | C₂H₅ | COCH₃ |
| 681 | X | Cl | CN₄H | —CH₂—(cyclohexyl)N— | * | H | COCH₃ |
| 682 | X | Cl | CO₂H | single bond | H | CH₃ | H |
| 683 | X | Cl | CO₂H | single bond | H | C₂H₅ | H |
| 684 | X | Cl | CN₄H | —CH₂—(cyclohexyl)N— | * | H | H |
| 685 | X | Cl | CN₄H | single bond | H | CH₃ | H |
| 686 | X | Cl | CN₄H | single bond | H | C₂H₅ | H |
| 687 | X | Cl | CN₄H | —CH₂CH₂—(cyclohexyl)N— | * | H | COCH₃ |

TABLE VI-continued

$$X = A-\overset{B}{N}-\overset{O}{\overset{\|}{C}}-CH_2-CH_2-\overset{CO_2E}{\underset{\underset{P}{\overset{|}{N-H}}}{\overset{|}{CH}}}$$

| Ex: # | R¹ | R² | R₅ | A | B | E | P |
|---|---|---|---|---|---|---|---|
| 688 | X | Cl | CO₂H | single bond | H | H | COCH₂Cl |
| 689 | X | Cl | CO₂H | single bond | H | H | COC₄H₉ |
| 690 | X | Cl | CO₂H | single bond | H | CH₃ | COCH₃ |
| 691 | X | Cl | CO₂H | single bond | H | C₂H₅ | COCH₃ |
| 692 | X | Cl | CN₄H | 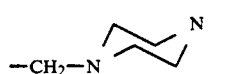 | * | H | H |
| 693 | X | Cl | CN₄H | single bond | H | H | COCH₂Cl |
| 694 | X | Cl | CN₄H | single bond | H | H | COC₄H₉ |
| 695 | X | Cl | CN₄H | single bond | H | CH₃ | COCH₃ |
| 696 | X | Cl | CN₄H | single bond | H | C₂H₅ | COCH₃ |
| 697 | X | Cl | CN₄H | 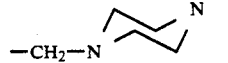 | * | H | COCH₃ |
| 698 | X | Cl | CO₂H | single bond | H | CH₃ | H |
| 699 | X | Cl | CO₂H | single bond | H | C₂H₅ | H |
| 700 | X | Cl | CN₄H | 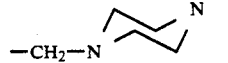 | * | H | H |
| 701 | X | Cl | CN₄H | single bond | H | CH₃ | H |
| 702 | X | Cl | CN₄H | single bond | H | C₂H₅ | H |
| 703 | X | Cl | CN₄H | 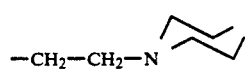 | * | H | COCH₃ |
| 704 | X | Cl | CN₄H | single bond | H | H | COCH₂Cl |
| 705 | X | Cl | CN₄H | single bond | H | H | COC₄H₉ |
| 706 | X | Cl | CN₄H | single bond | H | CH₃ | COCH₃ |
| 707 | X | Cl | CN₄H | single bond | H | C₂H₅ | COCH₃ |
| 708 | X | Cl | CN₄H | 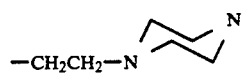 | * | H | H |
| 709 | X | Cl | CN₄H | single bond | H | CH₃ | H |
| 710 | X | Cl | CN₄H | single bond | H | C₂H₅ | H |

*B is incorporated in A

Another class of highly preferred specific conjugates of the invention is provided by conjugates formed from a biphenylmethyl 1H-substituted imidazole AII antagonist compound having a terminal carboxyl group attached to the imidazo nucleus. In this family of conjugates, the cleavable glutamyl residue is attached through a diamino linker moiety which connects the imidazo AII antagonist terminal carboxylic moiety through two amide bonds to the gamma carbon of the glutamyl residue Such conjugates are shown as Examples 711-1526. General procedures for preparation of the conjugates of Examples #711-#1526 are described in Schemes VI-VII. Detailed procedures for preparation of representative conjugates are described in Examples #711 and #712. Procedures similar to these aforementioned general and specific procedures may be used for preparation of the conjugates identified as Examples #711-#1526 shown in Table VII.

EXAMPLE 711

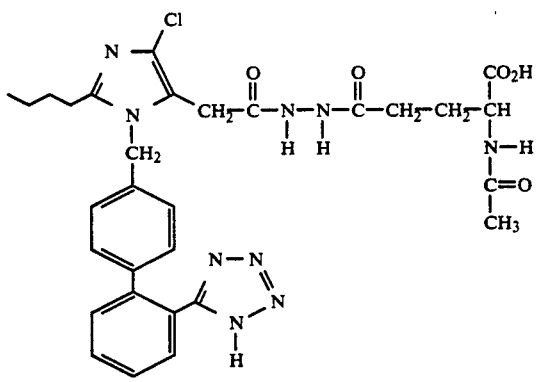

N-acetyl-L-glutamic acid,
5-[2-butyl-4-chloro-1-[[2'-(1H-tetrazol-5-yl)[1,1'-biphenyl]-4-yl]methyl]-1H-imidazol-5-yl]acetylhydrazide

Step 1: Preparation of 2-butyl-5-cyanomethyl-4-chloro-1-(2'-(1H-tetrazol-5-yl)biphenyl-4-methyl]imidazole.

Thionyl chloride (7.2 mL, 98 mmol) is slowly dripped into a solution of 8.45 g (20.0 mmol) of the compound of Example 78 in a minimum of chloroform. The mixture is stirred for 2 h at ambient temperature and the solvent is removed in vacuo. The chloride is dissolved in dimethylsulfoxide (DMSO) and is added to a solution of 5.80 g (118 mmol) of sodium cyanide in 400 mL of DMSO. The solution is stirred overnight under nitrogen at ambient temperature; water is added and the aqueous layer is extracted with ethyl acetate. The extracts are combined, are dried ($MgSO_4$), and are concentrated in vacuo to give the crude product. Purification by silica gel chromatography (Waters DeltaPrep-500A) provides the pure 5-cyanomethyl derivative.

Step 2: Preparation of 2-butyl-5-carboxymethyl-4-chloro-1-[(2'-(1H-tetrazol-5-yl)biphenyl-4-methyl]imidazole.

A solution of 6.5 g (15 mmol) of the 5-cyanomethyl derivative from step 1 in 150 mL of concentrated hydrochloric acid/acetic acid (1:1) is stirred at reflux overnight. The solvents are removed in vacuo to give the crude product. Purification by reverse phase chromatography (Waters Deltaprep-3000) provides the pure 5-acetic acid derivative.

Step 3: Preparation of 2-butyl-4-chloro-5-methoxycarbonylmethyl-1-[(2'-(1H-tetrazol-5-yl)biphenyl-4-methyl]imidazole.

A solution of 4.5 g (10 mmol) of the 5-acetic acid derivative from step 2 in 150 mL of absolute methanol is cooled to −10° C. and is treated with 1.5 mL (20 mmol) of thionyl chloride under nitrogen. The reaction is allowed to warm to ambient temperature and is stirred at reflux overnight. The methanol is removed in vacuo and the crude product is dissolved in water. The pH is adjusted to pH 4 with 1N NaOH and the solution is extracted with ethyl acetate. The extracts are combined, are dried ($MgSO_4$), and are concentrated in vacuo to give the crude product. Purification by silica gel chromatography (Waters Prep-500A) provides the pure 5-methyl acetate derivative.

Step 4: Preparation of 2-butyl-4-chloro-5-hydrazinylcarbonylmethyl-1-[(2'-(1H-tetrazol-5-yl)biphenyl-4-methyl]imidazole.

Under nitrogen, 2.32 g (5.0 mmol) of the 5-methyl acetate derivative from step 3 is dissolved in 50 mL of methanol and is treated with 5mL (160 mmol) of anhydrous hydrazine. The reaction is allowed to stir at reflux overnight; concentration in vacuo gives the crude material. Purification by silica gel chromatography (Waters Prep-500A) provides the pure 5-acetic acid hydrazide derivative.

Step 5: Preparation of N-acetyl-L-glutamic acid, 5-[2-butyl-4-chloro-1-[[2'-(1H-tetrazol-5-yl)[1,1'-biphenyl]-4-yl]methyl]-1H-imidazol-5-yl]acetyl]hydrazide To a solution of 1.70 g (5.6 mmol) glutamic acid-o-tertbutyl ester (BACHEM) in 50 mL of methylene chloride under nitrogen is added 580 mg (2.8 mmol) of solid dicylcohexylcarbodiimide (DCC). The reaction is allowed to stir for 2 h and is filtered under nitrogen. The anhydride solution is then added to a solution of 1.01 g (2.4 mmol) of the hydrazide from step 4 in 75 mL of methylene chloride under nitrogen. The reaction is stirred overnight, is concentrated to a volume of 25 mL, is cooled to 0° C., and is treated with 25 mL of TFA under nitrogen. The stirred reaction is allowed to warm to ambient temperature overnight and is concentrated in vacuo. The crude product is dissolved in 100 mL of acetonitrile/water (1:1) and the pH is adjusted to 8 with 1M $K_2CO_3$. The solution is cooled to 0° C. and 0.23 mL (2.4 mmol) of acetic anhydride and 2.4 mL (2.4 mmol) of 1M $K_2CO_3$ is added every 30 min for 5 h; the pH is maintained at 9 and the reaction temperature is kept below 5° C. After the last addition, the reaction is allowed to warm to ambient temperature overnight. The pH is adjusted to 4 with 3M HCl and the reaction is concentrated to 100 mL. Purification by reverse phase chromatography (Waters Deltaprep-3000) gives the pure product.

EXAMPLE 712

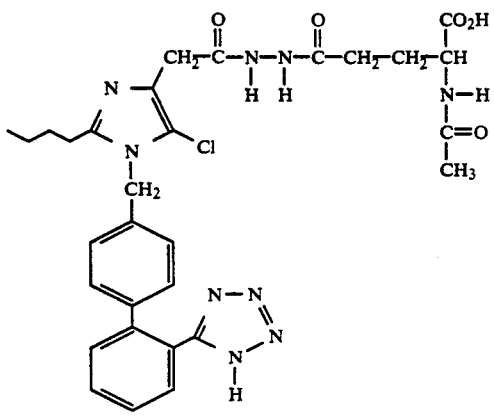

N-acetyl-L-glutamic acid, 5-[2-butyl-5-chloro-1-[[2'-(1H-tetrazol-5-yl)[1,1'-biphenyl]-4-yl]methyl]-1H-imidazol-4-yl]acetylhydrazide

Step 1: Preparation of 2-butyl-4-cyanomethyl-5-chloro-1-(2'-(1H-tetrazol-5-yl)biphenyl-4-methyl]imidazole.

Thionyl chloride (7.2 mL, 98 mmol) is slowly dripped into a solution of 8.45 g (20.0 mmol) of the compound of Example 79 in a minimum of chloroform. The mixture is stirred for 2 h at ambient temperature and the solvent is removed in vacuo. The chloride is dissolved in DMSO and is added to a solution of 5.80 g (118 mmol) of sodium cyanide in 400 mL of DMSO. The solution is stirred overnight under nitrogen at ambient temperature; water is added and the aqueous layer is extracted with ethyl acetate. The extracts are combined, are dried (MgSO$_4$), and are concentrated in vacuo to give the crude product. Purification by silica gel chromatography (Waters Prep-500A) provides the pure 4-cyanomethyl derivative.

Step 2: Preparation of 2-butyl-4-carboxymethyl-5-chloro-1-[(2'-(1H-tetrazol-5-yl)biphenyl-4-methyl]imidazole.

A solution of 6.5 g (15 mmol) of the 4-cyanomethyl derivative from step 1 in 150 mL of concentrated hydrochloric acid/acetic acid (1:1) is stirred at reflux overnight. The solvents are removed in vacuo to give the crude product. Purification by reverse phase chromatography provides (Waters Deltaprep-3000) the pure 4-acetic acid derivative.

Step 3: Preparation of 2-butyl-5-chloro-4-methoxycarbonylmethyl-1-[(2'-(1H-tetrazol-5-yl]biphenyl-4-methyl]imidazole.

A solution of 4.5 g (10 mmol) of the 4-acetic acid derivative from step 2 in 150 mL of absolute methanol is cooled to −10° C. and is treated with 1.5 mL (20 mmol) of thionyl chloride under nitrogen. The reaction is allowed to warm to ambient temperature and is stirred at reflux overnight. The methanol is removed in vacuo and the crude product is dissolved in water. The pH is adjusted to pH 4 with 1N NaOH and the solution is extracted with ethyl acetate. The extracts are combined, are dried (MgSO$_4$), and are concentrated in vacuo to give the crude product. Purification by silica gel chromatography (Waters Prep-500A) provides the pure 4-methyl acetate derivative.

Step 4: Preparation of 2-butyl-5-chloro-4-hydrazinylcarbonylmethyl-1-[(2'-(1H-tetrazole-5-yl)biphenyl-4-methyl]imidazole.

Under nitrogen, 2.32 g (5.0 mmol) of the 4-methyl acetate derivative from step 3 is dissolved in 50 mL of methanol and is treated with 5 mL (160 mmol) of anhydrous hydrazine. The reaction is allowed to stir at reflux overnight; concentration in vacuo gives the crude material. Purification by silica gel chromatography (Waters Prep-500A) provides the pure 4-acetic acid hydrazide derivative.

Step 5: Preparation of N-acetyl-L-glutamic acid, 5-[2-butyl-5-chloro-1-[[2'-(1H-tetrazol-5-yl)[1,1'-biphenyl]-4-yl]methyl]-1H-imidazol-4-yl]acetylhydrazide To a solution of 1.70 g (5.6 mmol) of N-Boc-L-glutamic acid-α-tertbutyl ester (BACHEM) in 50 mL of methylene chloride under nitrogen is added 580 mg (2.8 mmol) of solid dicylcohexylcarbodiimide (DCC). The reaction is allowed to stir for 2 h and is filtered under nitrogen. The anhydride solution is then added to a solution of 1.01 g (2.4 mmol) of the hydrazide from step 4 in 75 mL of methylene chloride under nitrogen. The reaction is stirred overnight, is concentrated to a volume of 25 mL, is cooled to 0° C., and is treated with 25 mL of TFA under nitrogen. The stirred reaction is allowed to warm to ambient temperature overnight and is concentrated in vacuo. The crude product is dissolved in 100 mL of acetonitrile/water (1:1) and the pH is adjusted to 8 with 1M K$_2$CO$_3$. The solution is cooled to 0° C. and 0.23 mL(2.4 mmol) of acetic anhydride and 2.4 mL (2.4 mmol) of 1M K$_2$CO$_3$ is added every 30 min for 5 h; the pH is maintained at 9 and the reaction temperature is kept below 5° C. After the last addition, the reaction is allowed to warm to ambient temperature overnight. The pH is adjusted to 4 with 3M HCl and the reaction is concentrated to 100 mL. Purification by reverse phase chromatography (Waters Deltaprep-3000) gives the pure product.

TABLE VII

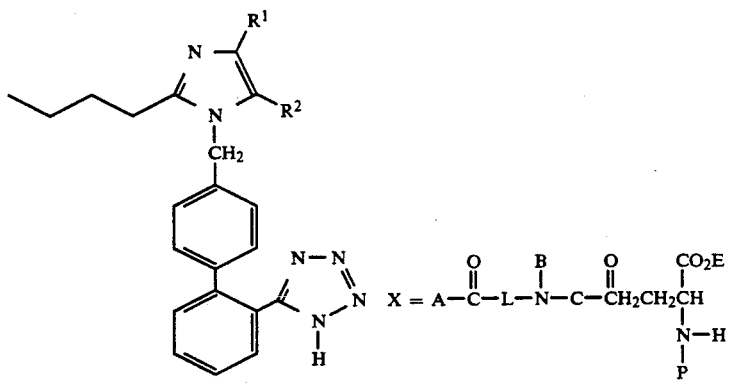

| Ex. # | R$^1$ | R$^2$ | A | L | B | E | P |
|---|---|---|---|---|---|---|---|
| 713 | Cl | X | single bond | —NH— | H | H | COCH3 |

-continued

| | | | | | | | |
|---|---|---|---|---|---|---|---|
| 714 | Cl | X | single bond | —NH— | H | H | COCH₂Cl |
| 715 | Cl | X | single bond | —NH— | H | H | COC₄H₉ |
| 716 | Cl | X | single bond | —NH— | H | CH₃ | COCH₃ |
| 717 | Cl | X | single bond | —NH— | H | C₂H₅ | COCH₃ |
| 718 | Cl | X | single bond | —NH— | H | H | H |
| 719 | Cl | X | single bond | —NH— | H | CH₃ | H |
| 720 | Cl | X | single bond | —NH— | H | C₂H₅ | H |
| 721 | Cl | X | single bond | —NHCH₂CH₂— | H | H | COCH₃ |
| 722 | Cl | X | single bond | —NHCH₂CH₂— | H | H | COCH₂Cl |
| 723 | Cl | X | single bond | —NHCH₂CH₂— | H | H | COC₄H₉ |
| 724 | Cl | X | single bond | —NHCH₂CH₂— | H | CH₃ | COCH₃ |
| 725 | Cl | X | single bond | —NHCH₂CH₂— | H | C₂H₅ | COCH₃ |
| 726 | Cl | X | single bond | —NHCH₂CH₂— | H | H | H |
| 727 | Cl | X | single bond | —NHCH₂CH₂— | H | CH₃ | H |
| 728 | Cl | X | single bond | —NHCH₂CH₂— | H | C₂H₅ | H |
| 729 | Cl | X | single bond | 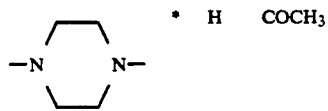 | * | H | COCH₃ |
| 730 | Cl | X | single bond | 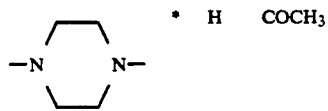 | H | H | COCH₂Cl |
| 731 | Cl | X | single bond | 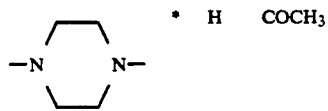 | H | H | COC₄H₉ |
| 732 | Cl | X | single bond | 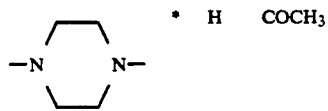 | H | CH₃ | COCH₃ |
| 733 | Cl | X | single bond | 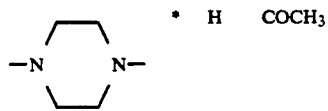 | H | C₂H₅ | COCH₃ |
| 734 | Cl | X | single bond | 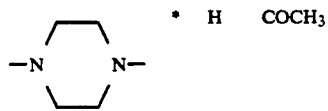 | * | H | H |
| 735 | Cl | X | single bond | 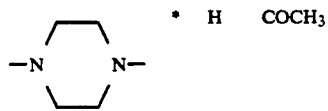 | H | CH₃ | H |
| 736 | Cl | X | single bond | 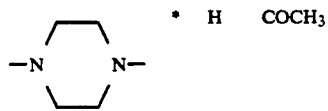 | H | C₂H₅ | H |
| 737 | Cl | X | CH₂ | —NH— | H | H | COCH₂Cl |
| 738 | Cl | X | CH₂ | —NH— | H | H | COC₄H₉ |
| 739 | Cl | X | CH₂ | —NH— | H | CH₃ | COCH₃ |
| 740 | Cl | X | CH₂ | —NH— | H | C₂H₅ | COCH₃ |
| 741 | Cl | X | CH₂ | —NH— | H | H | H |
| 742 | Cl | X | CH₂ | —NH— | H | CH₃ | H |
| 743 | Cl | X | CH₂ | —NH— | H | C₂H₅ | H |
| 744 | Cl | X | CH₂ | —NHCH₂CH₂— | H | H | COCH₃ |
| 745 | Cl | X | CH₂ | —NHCH₂CH₂— | H | H | COCH₂Cl |
| 746 | Cl | X | CH₂ | —NHCH₂CH₂— | H | H | COC₄H₉ |
| 747 | Cl | X | CH₂ | —NHCH₂CH₂— | H | CH₃ | COCH₃ |
| 748 | Cl | X | CH₂ | —NHCH₂CH₂— | H | C₂H₅ | COCH₃ |
| 749 | Cl | X | CH₂ | —NHCH₂CH₂— | H | H | H |
| 750 | Cl | X | CH₂ | —NHCH₂CH₂— | H | CH₃ | H |
| 751 | Cl | X | CH₂ | —NHCH₂CH₂— | H | C₂H₅ | H |

-continued

| | | | | | | | |
|---|---|---|---|---|---|---|---|
| 752 | Cl | X | CH$_2$ |  | * | H | COCH$_3$ |
| 753 | Cl | X | CH$_2$ |  | H | H | COCH$_2$Cl |
| 754 | Cl | X | CH$_2$ | 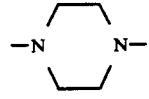 | H | H | COC$_4$H$_9$ |
| 755 | Cl | X | CH$_2$ | 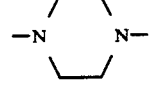 | H | CH$_3$ | COCH$_3$ |
| 756 | Cl | X | CH$_2$ | 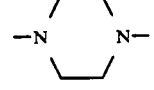 | H | C$_2$H$_5$ | COCH$_3$ |
| 757 | Cl | X | CH$_2$ | 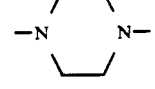 | * | H | H |
| 758 | Cl | X | CH$_2$ | 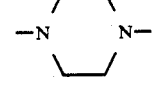 | H | CH$_3$ | H |
| 759 | Cl | X | CH$_2$ | | H | C$_2$H$_5$ | H |
| 760 | Cl | X | CH$_2$CH$_2$ | —NH— | H | H | COCH$_3$ |
| 761 | Cl | X | CH$_2$CH$_2$ | —NH— | H | H | COCH$_2$Cl |
| 762 | Cl | X | CH$_2$CH$_2$ | —NH— | H | H | COC$_4$H$_9$ |
| 763 | Cl | X | CH$_2$CH$_2$ | —NH— | H | CH$_3$ | COCH$_3$ |
| 764 | Cl | X | CH$_2$CH$_2$ | —NH— | H | C$_2$H$_5$ | COCH$_3$ |
| 765 | Cl | X | CH$_2$CH$_2$ | —NH— | H | H | H |
| 766 | Cl | X | CH$_2$CH$_2$ | —NH— | H | CH$_3$ | H |
| 767 | Cl | X | CH$_2$CH$_2$ | —NH— | H | C$_2$H$_5$ | H |
| 768 | Cl | X | CH$_2$CH$_2$ | —NHCH$_2$CH$_2$— | H | H | COCH$_3$ |
| 769 | Cl | X | CH$_2$CH$_2$ | —NHCH$_2$CH$_2$— | H | H | COCH$_2$Cl |
| 770 | Cl | X | CH$_2$CH$_2$ | —NHCH$_2$CH$_2$— | H | H | COC$_4$H$_9$ |
| 771 | Cl | X | CH$_2$CH$_2$ | —NHCH$_2$CH$_2$— | H | CH$_3$ | COCH$_3$ |
| 772 | Cl | X | CH$_2$CH$_2$ | —NHCH$_2$CH$_2$— | H | C$_2$H$_5$ | COCH$_3$ |
| 773 | Cl | X | CH$_2$CH$_2$ | —NHCH$_2$CH$_2$— | H | H | H |
| 774 | Cl | X | CH$_2$CH$_2$ | —NHCH$_2$CH$_2$— | H | CH$_3$ | H |
| 775 | Cl | X | CH$_2$CH$_2$ | —NHCH$_2$CH$_2$— | H | C$_2$H$_5$ | H |
| 776 | Cl | X | CH$_2$CH$_2$ | 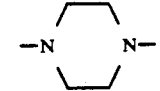 | * | H | COCH$_3$ |
| 777 | Cl | X | CH$_2$CH$_2$ | 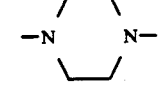 | H | H | COCH$_2$Cl |
| 778 | Cl | X | CH$_2$CH$_2$ | 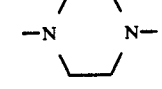 | H | H | COC$_4$H$_9$ |

| | | | | | | | |
|---|---|---|---|---|---|---|---|
| 779 | Cl | X | CH$_2$CH$_2$ | 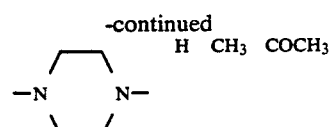 | H | CH$_3$ | COCH$_3$ |
| 780 | Cl | X | CH$_2$CH$_2$ | 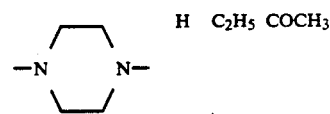 | H | C$_2$H$_5$ | COCH$_3$ |
| 781 | Cl | X | CH$_2$CH$_2$ | 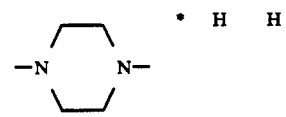 | • | H | H |
| 782 | Cl | X | CH$_2$CH$_2$ | 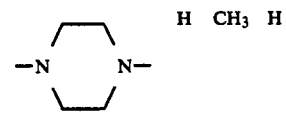 | H | CH$_3$ | H |
| 783 | Cl | X | CH$_2$CH$_2$ | 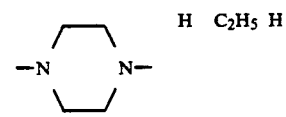 | H | C$_2$H$_5$ | H |
| 784 | Cl | X | C$_3$H$_6$(n) | —NH— | H | H | COCH$_3$ |
| 785 | Cl | X | C$_3$H$_6$(n) | —NH— | H | H | COCH$_2$Cl |
| 786 | Cl | X | C$_3$H$_6$(n) | —NH— | H | H | COC$_4$H$_9$ |
| 787 | Cl | X | C$_3$H$_6$(n) | —NH— | H | CH$_3$ | COCH$_3$ |
| 788 | Cl | X | C$_3$H$_6$(n) | —NH— | H | C$_2$H$_5$ | COCH$_3$ |
| 789 | Cl | X | C$_3$H$_6$(n) | —NH— | H | H | H |
| 790 | Cl | X | C$_3$H$_6$(n) | —NH— | H | CH$_3$ | H |
| 791 | Cl | X | C$_3$H$_6$(n) | —NH— | H | C$_2$H$_5$ | H |
| 792 | Cl | X | C$_3$H$_6$(n) | —NHCH$_2$CH$_2$— | H | H | COCH$_3$ |
| 793 | Cl | X | C$_3$H$_6$(n) | —NHCH$_2$CH$_2$— | H | H | COCH$_2$Cl |
| 794 | Cl | X | C$_3$H$_6$(n) | —NHCH$_2$CH$_2$— | H | H | COC$_4$H$_9$ |
| 795 | Cl | X | C$_3$H$_6$(n) | —NHCH$_2$CH$_2$— | H | CH$_3$ | COCH$_3$ |
| 796 | Cl | X | C$_3$H$_6$(n) | —NHCH$_2$CH$_2$— | H | C$_2$H$_5$ | COCH$_3$ |
| 797 | Cl | X | C$_3$H$_6$(n) | —NHCH$_2$CH$_2$— | H | H | H |
| 798 | Cl | X | C$_3$H$_6$(n) | —NHCH$_2$CH$_2$— | H | CH$_3$ | H |
| 799 | Cl | X | C$_3$H$_6$(n) | —NHCH$_2$CH$_2$— | H | C$_2$H$_5$ | H |
| 800 | Cl | X | C$_3$H$_6$(n) | 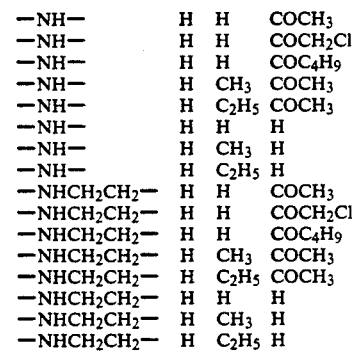 | • | H | COCH$_3$ |
| 801 | Cl | X | C$_3$H$_6$(n) | 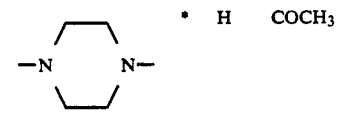 | H | H | COCH$_2$Cl |
| 802 | Cl | X | C$_3$H$_6$(n) | 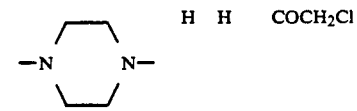 | H | H | COC$_4$H$_9$ |
| 803 | Cl | X | C$_3$H$_6$(n) | 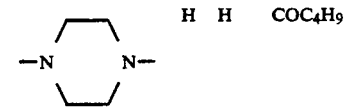 | H | CH$_3$ | COCH$_3$ |
| 804 | Cl | X | C$_3$H$_6$(n) | 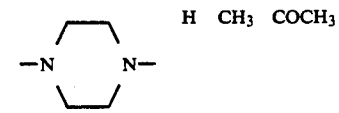 | H | C$_2$H$_5$ | COCH$_3$ |
| 805 | Cl | X | C$_3$H$_6$(n) | 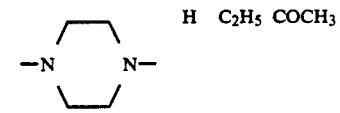 | • | H | H |

-continued

| | | | | | | | |
|---|---|---|---|---|---|---|---|
| 806 | Cl | X | C$_3$H$_6$(n) | 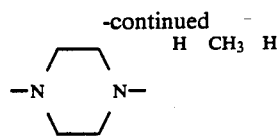 | H | CH$_3$ | H |
| 807 | Cl | X | C$_3$H$_6$(n) | 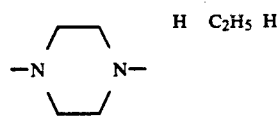 | H | C$_2$H$_5$ | H |
| 808 | Cl | X | C$_4$H$_8$(n) | —NH— | H | H | COCH$_3$ |
| 809 | Cl | X | C$_4$H$_8$(n) | —NH— | H | H | COCH$_2$Cl |
| 810 | Cl | X | C$_4$H$_8$(n) | —NH— | H | H | COC$_4$H$_9$ |
| 811 | Cl | X | C$_4$H$_8$(n) | —NH— | H | CH$_3$ | COCH$_3$ |
| 812 | Cl | X | C$_4$H$_8$(n) | —NH— | H | C$_2$H$_5$ | COCH$_3$ |
| 813 | Cl | X | C$_4$H$_8$(n) | —NH— | H | H | H |
| 814 | Cl | X | C$_4$H$_8$(n) | —NH— | H | CH$_3$ | H |
| 815 | Cl | X | C$_4$H$_8$(n) | —NH— | H | C$_2$H$_5$ | H |
| 816 | Cl | X | C$_4$H$_8$(n) | —NHCH$_2$CH$_2$— | H | H | COCH$_3$ |
| 817 | Cl | X | C$_4$H$_8$(n) | —NHCH$_2$CH$_2$— | H | H | COCH$_2$Cl |
| 818 | Cl | X | C$_4$H$_8$(n) | —NHCH$_2$CH$_2$— | H | H | COC$_4$H$_9$ |
| 819 | Cl | X | C$_4$H$_8$(n) | —NHCH$_2$CH$_2$— | H | CH$_3$ | COCH$_3$ |
| 820 | Cl | X | C$_4$H$_8$(n) | —NHCH$_2$CH$_2$— | H | C$_2$H$_5$ | COCH$_3$ |
| 821 | Cl | X | C$_4$H$_8$(n) | —NHCH$_2$CH$_2$— | H | H | H |
| 822 | Cl | X | C$_4$H$_8$(n) | —NHCH$_2$CH$_2$— | H | CH$_3$ | H |
| 823 | Cl | X | C$_4$H$_8$(n) | —NHCH$_2$CH$_2$— | H | C$_2$H$_5$ | H |
| 824 | Cl | X | C$_4$H$_8$(n) | 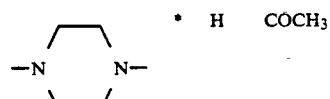 | * | H | COCH$_3$ |
| 825 | Cl | X | C$_4$H$_8$(n) | 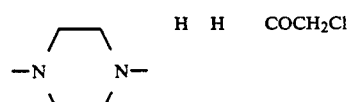 | H | H | COCH$_2$Cl |
| 826 | Cl | X | C$_4$H$_8$(n) | 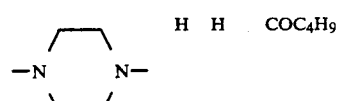 | H | H | COC$_4$H$_9$ |
| 827 | Cl | X | C$_4$H$_8$(n) | 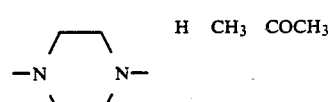 | H | CH$_3$ | COCH$_3$ |
| 828 | Cl | X | C$_4$H$_8$(n) | 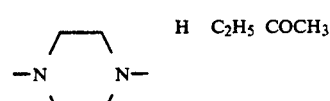 | H | C$_2$H$_5$ | COCH$_3$ |
| 829 | Cl | X | C$_4$H$_8$(n) | 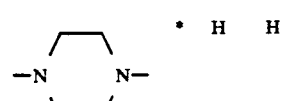 | * | H | H |
| 830 | Cl | X | C$_4$H$_8$(n) | 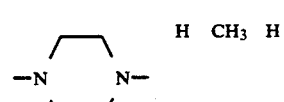 | H | CH$_3$ | H |
| 831 | Cl | X | C$_4$H$_8$(n) | 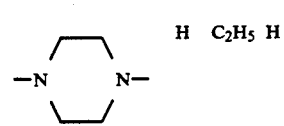 | H | C$_2$H$_5$ | H |
| 832 | Cl | X | 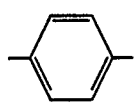 | —NH— | H | H | COCH$_3$ |

| | | | | | | |
|---|---|---|---|---|---|---|
| 833 | Cl | X |  | —NH— | H H | COCH$_2$Cl |
| 834 | Cl | X |  | —NH— | H H | COC$_4$H$_9$ |
| 835 | Cl | X | 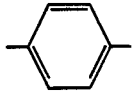 | —NH— | H CH$_3$ | COCH$_3$ |
| 836 | Cl | X | 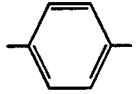 | —NH— | H C$_2$H$_5$ | COCH$_3$ |
| 837 | Cl | X | 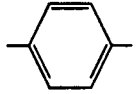 | —NH— | H H | H |
| 838 | Cl | X |  | —NH— | H CH$_3$ | H |
| 839 | Cl | X | 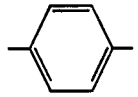 | —NH— | H C$_2$H$_5$ | H |
| 840 | Cl | X | 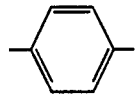 | —NHCH$_2$CH$_2$— | H H | COCH$_3$ |
| 841 | Cl | X | 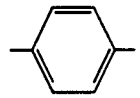 | —NHCH$_2$CH$_2$— | H H | COCH$_2$Cl |
| 842 | Cl | X | 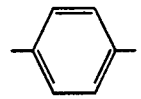 | —NHCH$_2$CH$_2$— | H H | COC$_4$H$_9$ |
| 843 | Cl | X | 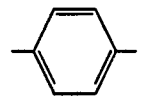 | —NHCH$_2$CH$_2$— | H CH$_3$ | COCH$_3$ |
| 844 | Cl | X | 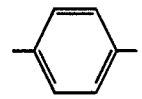 | —NHCH$_2$CH$_2$— | H C$_2$H$_5$ | COCH$_3$ |
| 845 | Cl | X | 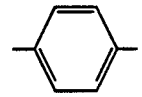 | —NHCH$_2$CH$_2$— | H H | H |
| 846 | Cl | X | 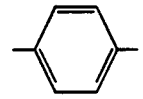 | —NHCH$_2$CH$_2$— | H CH$_3$ | H |

-continued
| | | | | | | | | |
|---|---|---|---|---|---|---|---|---|
| 847 | Cl | X | 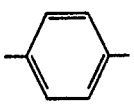 | —NHCH₂CH₂— | H | C₂H₅ | H | |
| 848 | Cl | X | 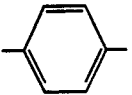 | 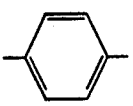 | * | H | COCH₃ | |
| 849 | Cl | X |  | 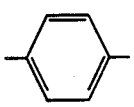 | H | H | COCH₂Cl | |
| 850 | Cl | X | 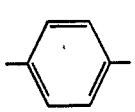 | 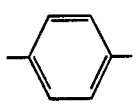 | H | H | COC₄H₉ | |
| 851 | Cl | X | 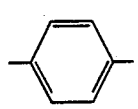 | 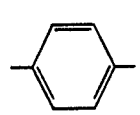 | H | CH₃ | COCH₃ | |
| 852 | Cl | X | 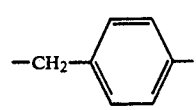 | 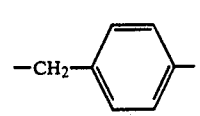 | H | C₂H₅ | COCH₃ | |
| 853 | Cl | X | 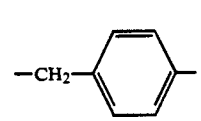 | 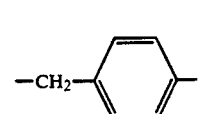 | * | H | H | |
| 854 | Cl | X | | | H | CH₃ | H | |
| 855 | Cl | X | | | H | C₂H₅ | H | |
| 856 | Cl | X | | —NH— | H | H | COCH₃ | |
| 857 | Cl | X | | —NH— | H | H | COCH₂Cl | |
| 858 | Cl | X | | —NH— | H | H | COC₄H₉ | |
| 859 | Cl | X | | —NH— | H | CH₃ | COCH₃ | |

-continued
| | | | | | | | |
|---|---|---|---|---|---|---|---|
| 860 | Cl | X | 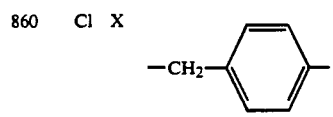 | —NH— | H | C₂H₅ | COCH₃ |
| 861 | Cl | X | 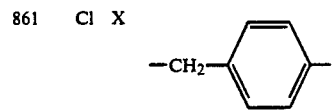 | —NH— | H | H | H |
| 862 | Cl | X | 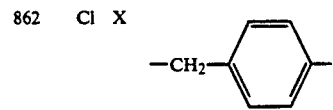 | —NH— | H | CH₃ | H |
| 863 | Cl | X | 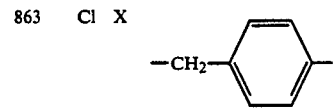 | —NH— | H | C₂H₅ | H |
| 864 | Cl | X | 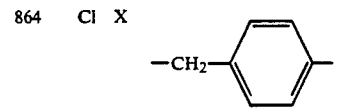 | —NHCH₂CH₂— | H | H | COCH₃ |
| 865 | Cl | X | 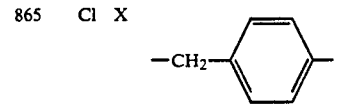 | —NHCH₂CH₂— | H | H | COCH₂Cl |
| 866 | Cl | X | 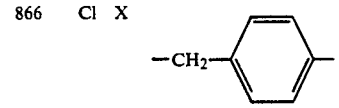 | —NHCH₂CH₂— | H | H | COC₄H₉ |
| 867 | Cl | X | 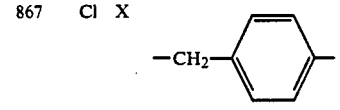 | —NHCH₂CH₂— | H | CH₃ | COCH₃ |
| 868 | Cl | X | 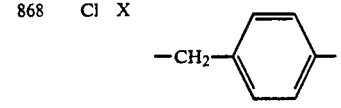 | —NHCH₂CH₂— | H | C₂H₅ | COCH₃ |
| 869 | Cl | X | 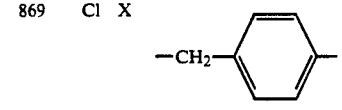 | —NHCH₂CH₂— | H | H | H |
| 870 | Cl | X | 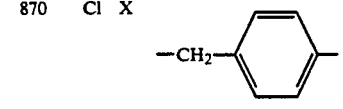 | —NHCH₂CH₂— | H | CH₃ | H |
| 871 | Cl | X | 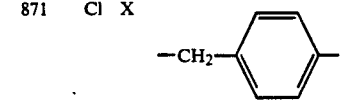 | —NHCH₂CH₂— | H | C₂H₅ | H |
| 872 | Cl | X | 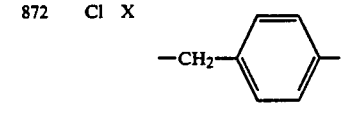 | piperazine | • | H | COCH₃ |
| 873 | Cl | X | 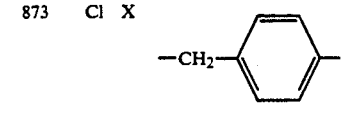 | piperazine | H | H | COCH₂Cl |

| | | | | | | |
|---|---|---|---|---|---|---|
| 874 | Cl X | —CH₂—⟨C₆H₄⟩— | —N(piperazine)N— | H | H | COC₄H₉ |
| 875 | Cl X | —CH₂—⟨C₆H₄⟩— | —N(piperazine)N— | H | CH₃ | COCH₃ |
| 876 | Cl X | —CH₂—⟨C₆H₄⟩— | —N(piperazine)N— | H | C₂H₅ | COCH₃ |
| 877 | Cl X | —CH₂—⟨C₆H₄⟩— | —N(piperazine)N— | * | H | H |
| 878 | Cl X | —CH₂—⟨C₆H₄⟩— | —N(piperazine)N— | H | CH₃ | H |
| 879 | Cl X | —CH₂—⟨C₆H₄⟩— | —N(piperazine)N— | H | C₂H₅ | H |
| 880 | Cl X | —CH₂CH₂—⟨C₆H₄⟩— | —NH— | H | H | COCH₃ |
| 881 | Cl X | —CH₂CH₂—⟨C₆H₄⟩— | —NH— | H | H | COCH₂Cl |
| 882 | Cl X | —CH₂CH₂—⟨C₆H₄⟩— | —NH— | H | H | COC₄H₉ |
| 883 | Cl X | —CH₂CH₂—⟨C₆H₄⟩— | —NH— | H | CH₃ | COCH₃ |
| 884 | Cl X | —CH₂CH₂—⟨C₆H₄⟩— | —NH— | H | C₂H₅ | COCH₃ |
| 885 | Cl X | —CH₂CH₂—⟨C₆H₄⟩— | —NH— | H | H | H |
| 886 | Cl X | —CH₂CH₂—⟨C₆H₄⟩— | —NH— | H | CH₃ | H |

| | | | | | | |
|---|---|---|---|---|---|---|
| 887 | Cl | X | —CH₂CH₂—⌬— | —NH— | H C₂H₅ | H |
| 888 | Cl | X | —CH₂CH₂—⌬— | —NHCH₂CH₂— | H H | COCH₃ |
| 889 | Cl | X | —CH₂CH₂—⌬— | —NHCH₂CH₂— | H H | COCH₂Cl |
| 890 | Cl | X | —CH₂CH₂—⌬— | —NHCH₂CH₂— | H H | COC₄H₉ |
| 891 | Cl | X | —CH₂CH₂—⌬— | —NHCH₂CH₂— | H CH₃ | COCH₃ |
| 892 | Cl | X | —CH₂CH₂—⌬— | —NHCH₂CH₂— | H C₂H₅ | COCH₃ |
| 893 | Cl | X | —CH₂CH₂—⌬— | —NHCH₂CH₂— | H H | H |
| 894 | Cl | X | —CH₂CH₂—⌬— | —NHCH₂CH₂— | H CH₃ | H |
| 895 | Cl | X | —CH₂CH₂—⌬— | —NHCH₂CH₂— | H C₂H₅ | H |
| 896 | Cl | X | —CH₂CH₂—⌬— | —N⟨piperazine⟩N— | * H | COCH₃ |
| 897 | Cl | X | —CH₂CH₂—⌬— | —N⟨piperazine⟩N— | H H | COCH₂Cl |
| 898 | Cl | X | —CH₂CH₂—⌬— | —N⟨piperazine⟩N— | H H | COC₄H₉ |
| 899 | Cl | X | —CH₂CH₂—⌬— | —N⟨piperazine⟩N— | H CH₃ | COCH₃ |
| 900 | Cl | X | —CH₂CH₂—⌬— | —N⟨piperazine⟩N— | H C₂H₅ | COCH₃ |

-continued

| # | | | | | | |
|---|---|---|---|---|---|---|
| 901 | Cl | X | —CH₂CH₂—C₆H₄— | —N(piperazine)N— | * H | H |
| 902 | Cl | X | —CH₂CH₂—C₆H₄— | —N(piperazine)N— | H CH₃ | H |
| 903 | Cl | X | —CH₂CH₂—C₆H₄— | —N(piperazine)N— | H C₂H₅ | H |
| 904 | Cl | X | —C₆H₄—CH₂— | —NH— | H H | COCH₃ |
| 905 | Cl | X | —C₆H₄—CH₂— | —NH— | H H | COCH₂Cl |
| 906 | Cl | X | —C₆H₄—CH₂— | —NH— | H H | COC₄H₉ |
| 907 | Cl | X | —C₆H₄—CH₂— | —NH— | H CH₃ | COCH₃ |
| 908 | Cl | X | —C₆H₄—CH₂— | —NH— | H C₂H₅ | COCH₃ |
| 909 | Cl | X | —C₆H₄—CH₂— | —NH— | H H | H |
| 910 | Cl | X | —C₆H₄—CH₂— | —NH— | H CH₃ | H |
| 911 | Cl | X | —C₆H₄—CH₂— | —NH— | H C₂H₅ | H |
| 912 | Cl | X | —C₆H₄—CH₂— | —NHCH₂CH₂— | H H | COCH₃ |
| 913 | Cl | X | —C₆H₄—CH₂— | —NHCH₂CH₂— | H H | COCH₂Cl |
| 914 | Cl | X | —C₆H₄—CH₂— | —NHCH₂CH₂— | H H | COC₄H₉ |

-continued
| | | | | | | | |
|---|---|---|---|---|---|---|---|
| 915 | Cl | X | 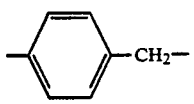 | —NHCH₂CH₂— | H | CH₃ | COCH₃ |
| 916 | Cl | X | 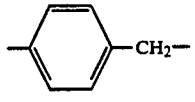 | —NHCH₂CH₂— | H | C₂H₅ | COCH₃ |
| 917 | Cl | X | 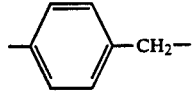 | —NHCH₂CH₂— | H | H | H |
| 918 | Cl | X | 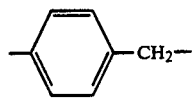 | —NHCH₂CH₂— | H | CH₃ | H |
| 919 | Cl | X | 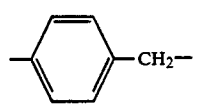 | —NHCH₂CH₂— | H | C₂H₅ | H |
| 920 | Cl | X | 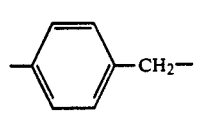 | 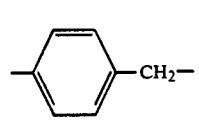 | * | H | COCH₃ |
| 921 | Cl | X | 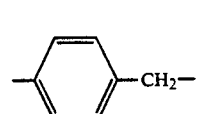 | 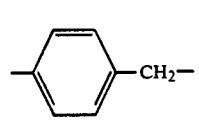 | H | H | COCH₂Cl |
| 922 | Cl | X | 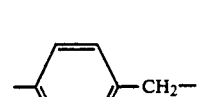 | 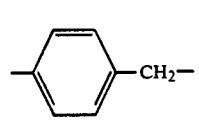 | H | H | COC₄H₉ |
| 923 | Cl | X |  | 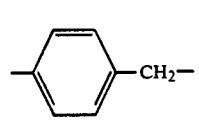 | H | CH₃ | COCH₃ |
| 924 | Cl | X |  | 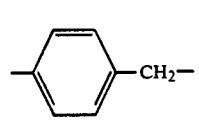 | H | C₂H₅ | COCH₃ |
| 925 | Cl | X | 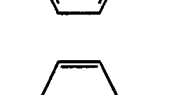 | 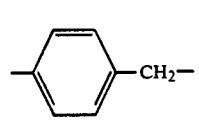 | * | H | H |
| 926 | Cl | X | 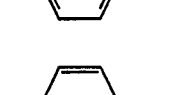 | 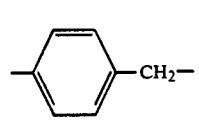 | H | CH₃ | H |
| 927 | Cl | X | 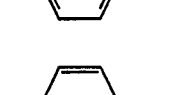 | 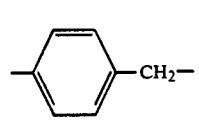 | H | C₂H₅ | H |

| | | | | | | | |
|---|---|---|---|---|---|---|---|
| 928 | Cl | X | 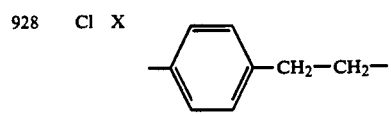 | —NH— | H | H | COCH₃ |
| 929 | Cl | X | 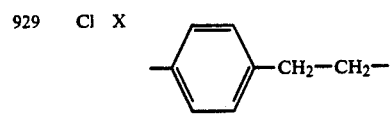 | —NH— | H | H | COCH₂Cl |
| 930 | Cl | X | 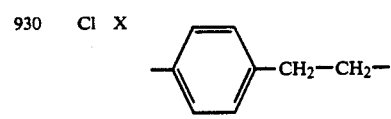 | —NH— | H | H | COC₄H₉ |
| 931 | Cl | X | 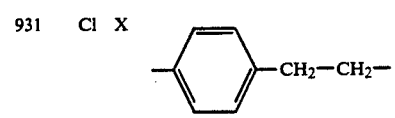 | —NH— | H | CH₃ | COCH₃ |
| 932 | Cl | X | 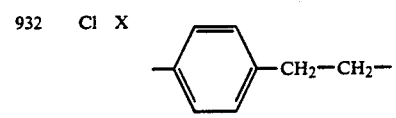 | —NH— | H | C₂H₅ | COCH₃ |
| 933 | Cl | X | 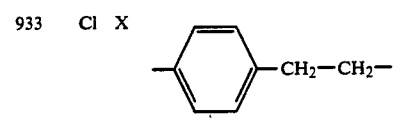 | —NH— | H | H | H |
| 934 | Cl | X | 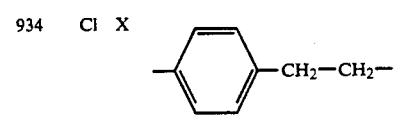 | —NH— | H | CH₃ | H |
| 935 | Cl | X | 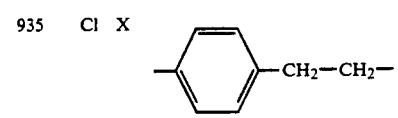 | —NH— | H | C₂H₅ | H |
| 936 | Cl | X | 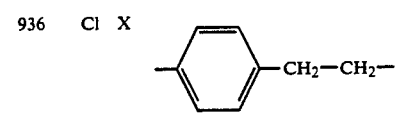 | —NHCH₂CH₂— | H | H | COCH₃ |
| 937 | Cl | X | 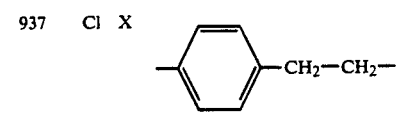 | —NHCH₂CH₂— | H | H | COCH₂Cl |
| 938 | Cl | X | 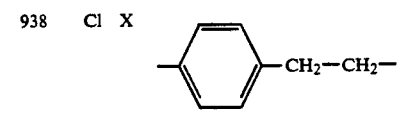 | —NHCH₂CH₂— | H | H | COC₄H₉ |
| 939 | Cl | X | 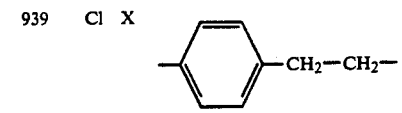 | —NHCH₂CH₂— | H | CH₃ | COCH₃ |
| 940 | Cl | X | 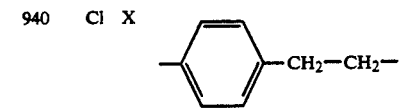 | —NHCH₂CH₂— | H | C₂H₅ | COCH₃ |
| 941 | Cl | X | 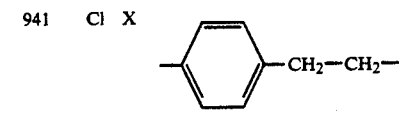 | —NHCH₂CH₂— | H | H | H |

| | | | | | | |
|---|---|---|---|---|---|---|
| 942 | Cl | X | 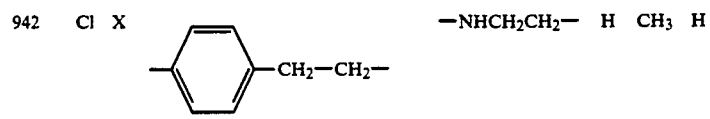 | —NHCH₂CH₂— | H | CH₃ | H |
| 943 | Cl | X | 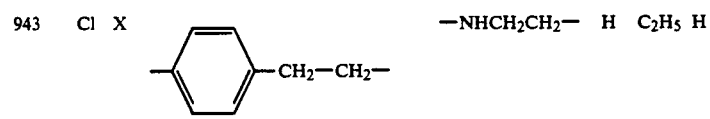 | —NHCH₂CH₂— | H | C₂H₅ | H |
| 944 | Cl | X | 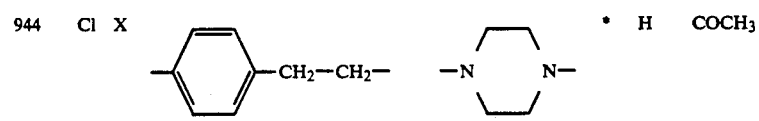 | | * | H | COCH₃ |
| 945 | Cl | X | 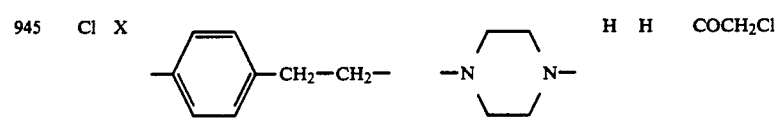 | | H | H | COCH₂Cl |
| 946 | Cl | X | 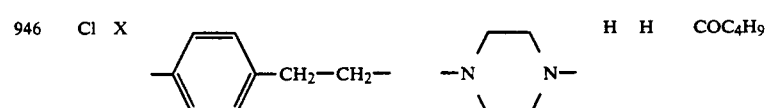 | | H | H | COC₄H₉ |
| 947 | Cl | X | 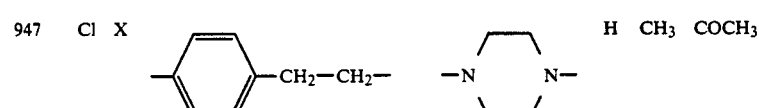 | | H | CH₃ | COCH₃ |
| 948 | Cl | X | 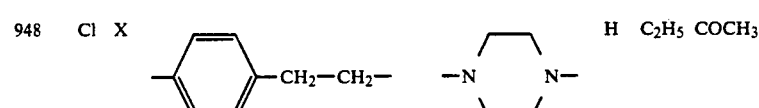 | | H | C₂H₅ | COCH₃ |
| 949 | Cl | X | 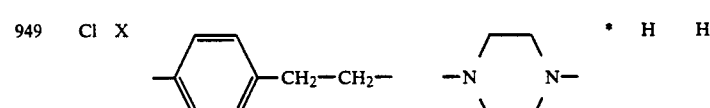 | | * | H | H |
| 950 | Cl | X | 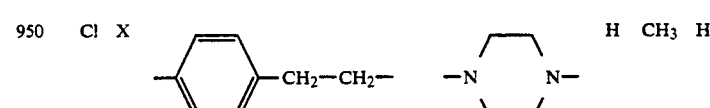 | | H | CH₃ | H |
| 951 | Cl | X | 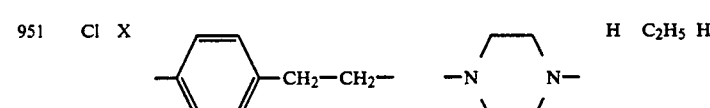 | | H | C₂H₅ | H |
| 952 | Cl | X | 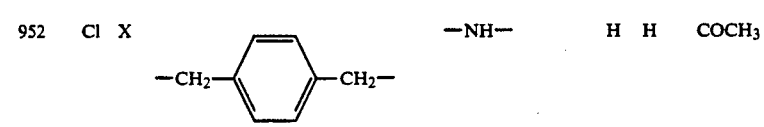 | —NH— | H | H | COCH₃ |
| 953 | Cl | X | 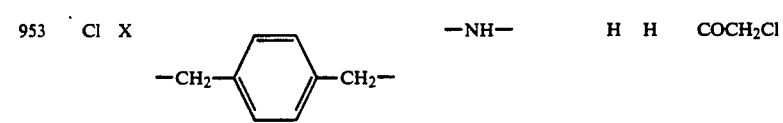 | —NH— | H | H | COCH₂Cl |
| 954 | Cl | X | 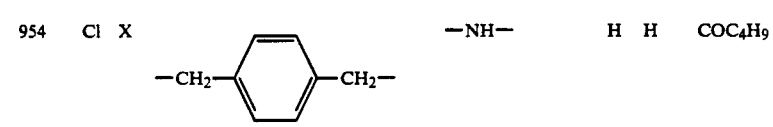 | —NH— | H | H | COC₄H₉ |

| | | | | | | |
|---|---|---|---|---|---|---|
| 955 | Cl | X | 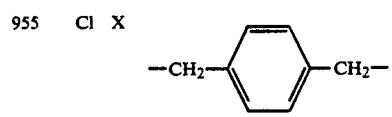 | —NH— | H CH₃ COCH₃ | |
| 956 | Cl | X | 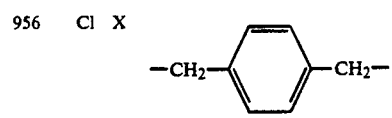 | —NH— | H C₂H₅ COCH₃ | |
| 957 | Cl | X | 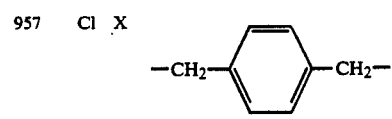 | —NH— | H H H | |
| 958 | Cl | X | 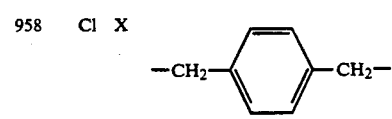 | —NH— | H CH₃ H | |
| 959 | Cl | X | 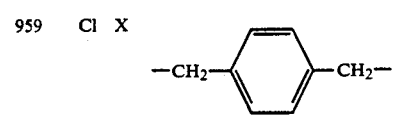 | —NH— | H C₂H₅ H | |
| 960 | Cl | X | 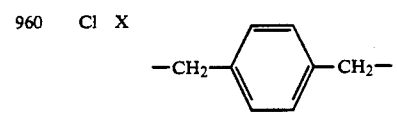 | —NHCH₂CH₂— | H H COCH₃ | |
| 961 | Cl | X | 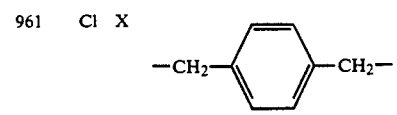 | —NHCH₂CH₂— | H H COCH₂Cl | |
| 962 | Cl | X | 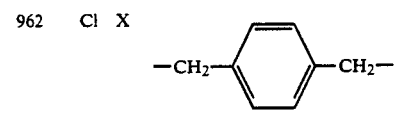 | —NHCH₂CH₂— | H H COC₄H₉ | |
| 963 | Cl | X | 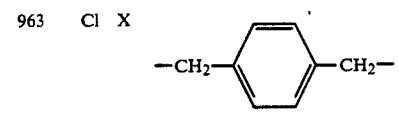 | —NHCH₂CH₂— | H CH₃ COCH₃ | |
| 964 | Cl | X | 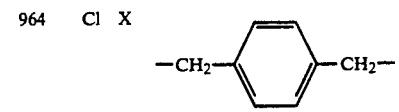 | —NHCH₂CH₂— | H C₂H₅ COCH₃ | |
| 965 | Cl | X | 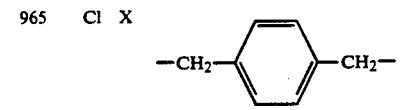 | —NHCH₂CH₂— | H H H | |
| 966 | Cl | X | 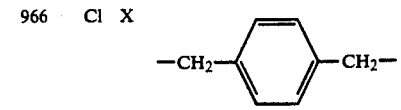 | —NHCH₂CH₂— | H CH₃ H | |
| 967 | Cl | X | 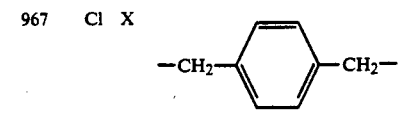 | —NHCH₂CH₂— | H C₂H₅ H | |

-continued
| | | | | | | | |
|---|---|---|---|---|---|---|---|
| 968 | Cl | X | 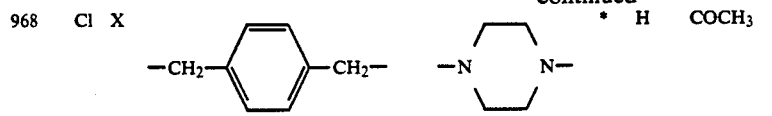 | | * | H | COCH$_3$ |
| 969 | Cl | X | 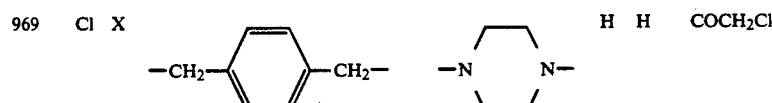 | | H | H | COCH$_2$Cl |
| 970 | Cl | X | 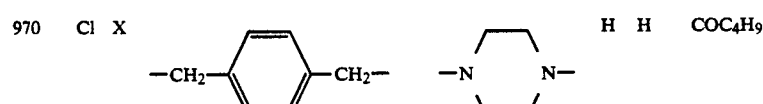 | | H | H | COC$_4$H$_9$ |
| 971 | Cl | X | 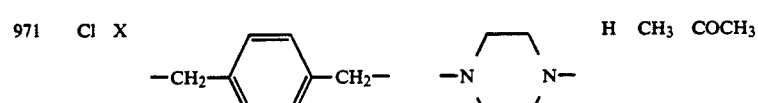 | | H | CH$_3$ | COCH$_3$ |
| 972 | Cl | X | 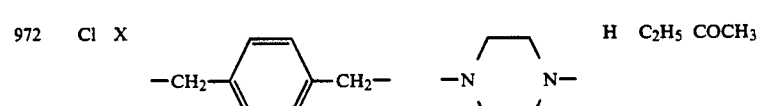 | | H | C$_2$H$_5$ | COCH$_3$ |
| 973 | Cl | X | 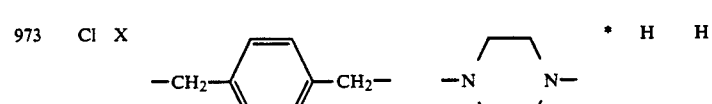 | | * | H | H |
| 974 | Cl | X | 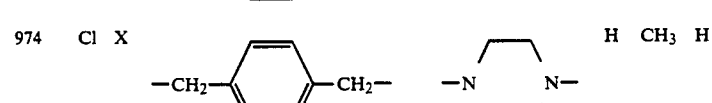 | | H | CH$_3$ | H |
| 975 | Cl | X | 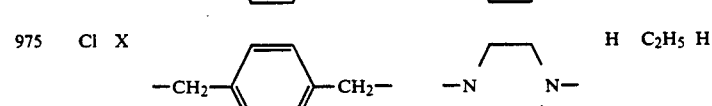 | | H | C$_2$H$_5$ | H |
| 976 | Cl | X |  | —NH— | H | H | COCH$_3$ |
| 977 | Cl | X |  | —NH— | H | H | COCH$_2$Cl |
| 978 | Cl | X |  | —NH— | H | H | COC$_4$H$_9$ |
| 979 | Cl | X |  | —NH— | H | CH$_3$ | COCH$_3$ |
| 980 | Cl | X |  | —NH— | H | C$_2$H$_5$ | COCH$_3$ |
| 981 | Cl | X |  | —NH— | H | H | H |
| 982 | Cl | X |  | —NH— | H | CH$_3$ | H |
| 983 | Cl | X |  | —NH— | H | C$_2$H$_5$ | H |
| 984 | Cl | X |  | —NHCH$_2$CH$_2$— | H | H | COCH$_3$ |

| No. | | | | | | |
|---|---|---|---|---|---|---|
| 985 | Cl X | (cyclohexyl) | —NHCH$_2$CH$_2$— | H | H | COCH$_2$Cl |
| 986 | Cl X | (cyclohexyl) | —NHCH$_2$CH$_2$— | H | H | COC$_4$H$_9$ |
| 987 | Cl X | (cyclohexyl) | —NHCH$_2$CH$_2$— | H | CH$_3$ | COCH$_3$ |
| 988 | Cl X | (cyclohexyl) | —NHCH$_2$CH$_2$— | H | C$_2$H$_5$ | COCH$_3$ |
| 989 | Cl X | (cyclohexyl) | —NHCH$_2$CH$_2$— | H | H | H |
| 990 | Cl X | (cyclohexyl) | —NHCH$_2$CH$_2$— | H | CH$_3$ | H |
| 991 | Cl X | (cyclohexyl) | —NHCH$_2$CH$_2$— | H | C$_2$H$_5$ | H |
| 992 | Cl X | (cyclohexyl) | piperazine | * | H | COCH$_3$ |
| 993 | Cl X | (cyclohexyl) | piperazine | H | H | COCH$_2$Cl |
| 994 | Cl X | (cyclohexyl) | piperazine | H | H | COC$_4$H$_9$ |
| 995 | Cl X | (cyclohexyl) | piperazine | H | CH$_3$ | COCH$_3$ |
| 996 | Cl X | (cyclohexyl) | piperazine | H | C$_2$H$_5$ | COCH$_3$ |
| 997 | Cl X | (cyclohexyl) | piperazine | * | H | H |
| 998 | Cl X | (cyclohexyl) | piperazine | H | CH$_3$ | H |
| 999 | Cl X | (cyclohexyl) | piperazine | H | C$_2$H$_5$ | H |
| 1000 | Cl X | —CH$_2$—(cyclohexyl) | —NH— | H | H | COCH$_3$ |

-continued

| | | | | | | | |
|---|---|---|---|---|---|---|---|
| 1001 | Cl | X | —CH₂—[cyclohexyl] | —NH— | H | H | COCH₂Cl |
| 1002 | Cl | X | —CH₂—[cyclohexyl] | —NH— | H | H | COC₄H₉ |
| 1003 | Cl | X | —CH₂—[cyclohexyl] | —NH— | H | CH₃ | COCH₃ |
| 1004 | Cl | X | —CH₂—[cyclohexyl] | —NH— | H | C₂H₅ | COCH₃ |
| 1005 | Cl | X | —CH₂—[cyclohexyl] | —NH— | H | H | H |
| 1006 | Cl | X | —CH₂—[cyclohexyl] | —NH— | H | CH₃ | H |
| 1007 | Cl | X | —CH₂—[cyclohexyl] | —NH— | H | C₂H₅ | H |
| 1008 | Cl | X | —CH₂—[cyclohexyl] | —NHCH₂CH₂— | H | H | COCH₃ |
| 1009 | Cl | X | —CH₂—[cyclohexyl] | —NHCH₂CH₂— | H | H | COCH₂Cl |
| 1010 | Cl | X | —CH₂—[cyclohexyl] | —NHCH₂CH₂— | H | H | COC₄H₉ |
| 1011 | Cl | X | —CH₂—[cyclohexyl] | —NHCH₂CH₂— | H | CH₃ | COCH₃ |
| 1012 | Cl | X | —CH₂—[cyclohexyl] | —NHCH₂CH₂— | H | C₂H₅ | COCH₃ |
| 1013 | Cl | X | —CH₂—[cyclohexyl] | —NHCH₂CH₂— | H | H | H |
| 1014 | Cl | X | —CH₂—[cyclohexyl] | —NHCH₂CH₂— | H | CH₃ | H |
| 1015 | Cl | X | —CH₂—[cyclohexyl] | —NHCH₂CH₂— | H | C₂H₅ | H |
| 1016 | Cl | X | —CH₂—[cyclohexyl] | —N⌒N— (piperazine) | * | H | COCH₃ |
| 1017 | Cl | X | —CH₂—[cyclohexyl] | —N⌒N— (piperazine) | H | H | COCH₂Cl |
| 1018 | Cl | X | —CH₂—[cyclohexyl] | —N⌒N— (piperazine) | H | H | COC₄H₉ |

-continued

| | | | | | | | |
|---|---|---|---|---|---|---|---|
| 1019 | Cl | X | -CH2-[cyclohexyl]- | -N[piperazine]N- | H | CH3 | COCH3 |
| 1020 | Cl | X | -CH2-[cyclohexyl]- | -N[piperazine]N- | H | C2H5 | COCH3 |
| 1021 | Cl | X | -CH2-[cyclohexyl]- | -N[piperazine]N- | * | H | H |
| 1022 | Cl | X | -CH2-[cyclohexyl]- | -N[piperazine]N- | H | CH3 | H |
| 1023 | Cl | X | -CH2-[cyclohexyl]- | -N[piperazine]N- | H | C2H5 | H |
| 1024 | Cl | X | -CH2CH2-[cyclohexyl]- | -NH- | H | H | COCH3 |
| 1025 | Cl | X | -CH2CH2-[cyclohexyl]- | -NH- | H | H | COCH2Cl |
| 1026 | Cl | X | -CH2CH2-[cyclohexyl]- | -NH- | H | H | COC4H9 |
| 1027 | Cl | X | -CH2CH2-[cyclohexyl]- | -NH- | H | CH3 | COCH3 |
| 1028 | Cl | X | -CH2CH2-[cyclohexyl]- | -NH- | H | C2H5 | COCH3 |
| 1029 | Cl | X | -CH2CH2-[cyclohexyl]- | -NH- | H | H | H |
| 1030 | Cl | X | -CH2CH2-[cyclohexyl]- | -NH- | H | CH3 | H |
| 1031 | Cl | X | -CH2CH2-[cyclohexyl]- | -NH- | H | C2H5 | H |
| 1032 | Cl | X | -CH2CH2-[cyclohexyl]- | -NHCH2CH2- | H | H | COCH3 |
| 1033 | Cl | X | -CH2CH2-[cyclohexyl]- | -NHCH2CH2- | H | H | COCH2Cl |
| 1034 | Cl | X | -CH2CH2-[cyclohexyl]- | -NHCH2CH2- | H | H | COC4H9 |
| 1035 | Cl | X | -CH2CH2-[cyclohexyl]- | -NHCH2CH2- | H | CH3 | COCH3 |

-continued

| | | | | | | | |
|---|---|---|---|---|---|---|---|
| 1036 | Cl | X | 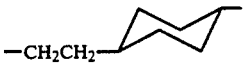 -CH$_2$CH$_2$- | -NHCH$_2$CH$_2$- | H | C$_2$H$_5$ | COCH$_3$ |
| 1037 | Cl | X | 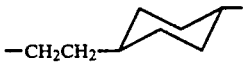 -CH$_2$CH$_2$- | -NHCH$_2$CH$_2$- | H | H | H |
| 1038 | Cl | X | 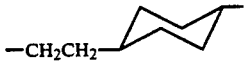 -CH$_2$CH$_2$- | -NHCH$_2$CH$_2$- | H | CH$_3$ | H |
| 1039 | Cl | X | 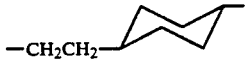 -CH$_2$CH$_2$- | -NHCH$_2$CH$_2$- | H | C$_2$H$_5$ | H |
| 1040 | Cl | X | 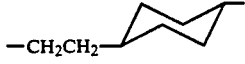 -CH$_2$CH$_2$- | 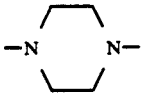 | * | H | COCH$_3$ |
| 1041 | Cl | X | 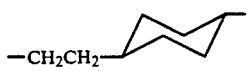 -CH$_2$CH$_2$- | 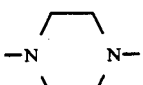 | H | H | COCH$_2$Cl |
| 1042 | Cl | X |  -CH$_2$CH$_2$- | 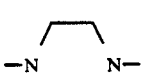 | H | H | COC$_4$H$_9$ |
| 1043 | Cl | X |  -CH$_2$CH$_2$- | 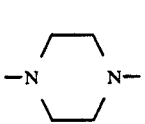 | H | CH$_3$ | COCH$_3$ |
| 1044 | Cl | X |  -CH$_2$CH$_2$- |  | H | C$_2$H$_5$ | COCH$_3$ |
| 1045 | Cl | X |  -CH$_2$CH$_2$- |  | * | H | H |
| 1046 | Cl | X |  -CH$_2$CH$_2$- | 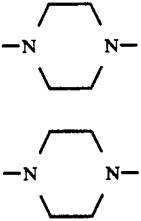 | H | CH$_3$ | H |
| 1047 | Cl | X | 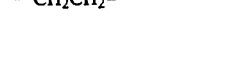 -CH$_2$CH$_2$- |  | H | C$_2$H$_5$ | H |
| 1048 | Cl | X | 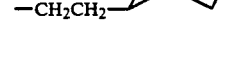 -CH$_2$- | -NH- | H | H | COCH$_3$ |
| 1049 | Cl | X |  -CH$_2$- | -NH- | H | H | COCH$_2$Cl |
| 1050 | Cl | X |  -CH$_2$- | -NH- | H | H | COC$_4$H$_9$ |
| 1051 | Cl | X |  -CH$_2$- | -NH- | H | CH$_3$ | COCH$_3$ |

-continued
| | | | | | | | |
|---|---|---|---|---|---|---|---|
| 1052 | Cl | X |  | —NH— | H | C₂H₅ | COCH₃ |
| 1053 | Cl | X |  | —NH— | H | H | H |
| 1054 | Cl | X |  | —NH— | H | CH₃ | H |
| 1055 | Cl | X |  | —NH— | H | C₂H₅ | H |
| 1056 | Cl | X |  | —NHCH₂CH₂— | H | H | COCH₃ |
| 1057 | Cl | X |  | —NH— | H | H | COCH₂Cl |
| 1058 | Cl | X |  | —NH— | H | H | COC₄H₉ |
| 1059 | Cl | X |  | —NH— | H | CH₃ | COCH₃ |
| 1060 | Cl | X |  | —NH— | H | C₂H₅ | COCH₃ |
| 1061 | Cl | X |  | —NHCH₂CH₂— | H | H | H |
| 1062 | Cl | X |  | —NHCH₂CH₂— | H | CH₃ | H |
| 1063 | Cl | X |  | —NHCH₂CH₂— | H | C₂H₅ | H |
| 1064 | Cl | X |  |  | * | H | COCH₃ |
| 1065 | Cl | X | 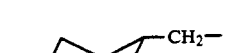 | 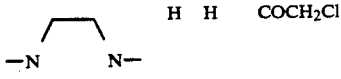 | H | H | COCH₂Cl |
| 1066 | Cl | X | 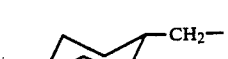 | 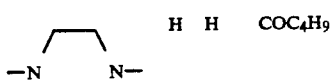 | H | H | COC₄H₉ |
| 1067 | Cl | X |  | 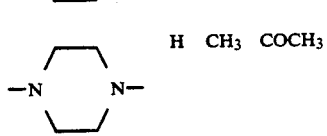 | H | CH₃ | COCH₃ |
| 1068 | Cl | X |  |  | * | C₂H₅ | COCH₃ |

-continued

| # | | | | | | | |
|---|---|---|---|---|---|---|---|
| 1069 | Cl | X | cyclohexyl-CH₂— | piperazine (—N\_\_N—) | · H | H | |
| 1070 | Cl | X | cyclohexyl-CH₂— | piperazine (—N\_\_N—) | H | CH₃ | H |
| 1071 | Cl | X | cyclohexyl-CH₂— | piperazine (—N\_\_N—) | H | C₂H₅ | H |
| 1072 | Cl | X | cyclohexyl-CH₂CH₂— | —NH— | H | H | COCH₃ |
| 1073 | Cl | X | cyclohexyl-CH₂CH₂— | —NH— | H | H | COCH₂Cl |
| 1074 | Cl | X | cyclohexyl-CH₂CH₂— | —NH— | H | H | COC₄H₉ |
| 1075 | Cl | X | cyclohexyl-CH₂CH₂— | —NH— | H | CH₃ | COCH₃ |
| 1076 | Cl | X | cyclohexyl-CH₂CH₂— | —NH— | H | C₂H₅ | COCH₃ |
| 1077 | Cl | X | cyclohexyl-CH₂CH₂— | —NH— | H | H | H |
| 1078 | Cl | X | cyclohexyl-CH₂CH₂— | —NH— | H | CH₃ | H |
| 1079 | Cl | X | cyclohexyl-CH₂CH₂— | —NH— | H | C₂H₅ | H |
| 1080 | Cl | X | cyclohexyl-CH₂CH₂— | —NHCH₂CH₂— | H | H | COCH₃ |
| 1081 | Cl | X | cyclohexyl-CH₂CH₂— | —NHCH₂CH₂— | H | H | COCH₂Cl |
| 1082 | Cl | X | cyclohexyl-CH₂CH₂— | —NHCH₂CH₂— | H | H | COC₄H₉ |
| 1083 | Cl | X | cyclohexyl-CH₂CH₂— | —NHCH₂CH₂— | H | CH₃ | COCH₃ |
| 1084 | Cl | X | cyclohexyl-CH₂CH₂— | —NHCH₂CH₂— | H | C₂H₅ | COCH₃ |
| 1085 | Cl | X | cyclohexyl-CH₂CH₂— | —NHCH₂CH₂— | H | H | H |
| 1086 | Cl | X | cyclohexyl-CH₂CH₂— | —NHCH₂CH₂— | H | CH₃ | H |
| 1087 | Cl | X | cyclohexyl-CH₂CH₂— | —NHCH₂CH₂— | H | C₂H₅ | H |

| | | | | -continued | | | |
|---|---|---|---|---|---|---|---|
| 1088 | Cl X | cyclohexyl–CH₂CH₂– | –N(piperazine)N– | * | H | COCH₃ |
| 1089 | Cl X | cyclohexyl–CH₂CH₂– | –N(piperazine)N– | H | H | COCH₂Cl |
| 1090 | Cl X | cyclohexyl–CH₂CH₂– | –N(piperazine)N– | H | H | COC₄H₉ |
| 1091 | Cl X | cyclohexyl–CH₂CH₂– | –N(piperazine)N– | H | CH₃ | COCH₃ |
| 1092 | Cl X | cyclohexyl–CH₂CH₂– | –N(piperazine)N– | H | C₂H₅ | COCH₃ |
| 1093 | Cl X | cyclohexyl–CH₂CH₂– | –N(piperazine)N– | * | H | H |
| 1094 | Cl X | cyclohexyl–CH₂CH₂– | –N(piperazine)N– | H | CH₃ | H |
| 1095 | Cl X | cyclohexyl–CH₂CH₂– | –N(piperazine)N– | H | C₂H₅ | H |
| 1096 | Cl X | –CH₂–cyclohexyl–CH₂– | –NH– | H | H | COCH₃ |
| 1097 | Cl X | –CH₂–cyclohexyl–CH₂– | –NH– | H | H | COCH₂Cl |
| 1098 | Cl X | –CH₂–cyclohexyl–CH₂– | –NH– | H | H | COC₄H₉ |
| 1099 | Cl X | –CH₂–cyclohexyl–CH₂– | –NH– | H | CH₃ | COCH₃ |
| 1100 | Cl X | –CH₂–cyclohexyl–CH₂– | –NH– | H | C₂H₅ | COCH₃ |
| 1101 | Cl X | –CH₂–cyclohexyl–CH₂– | –NH– | H | H | H |
| 1102 | Cl X | –CH₂–cyclohexyl–CH₂– | –NH– | H | CH₃ | H |
| 1103 | Cl X | –CH₂–cyclohexyl–CH₂– | –NH– | H | C₂H₅ | H |

| | | | | | | | |
|---|---|---|---|---|---|---|---|
| 1104 | Cl | X | 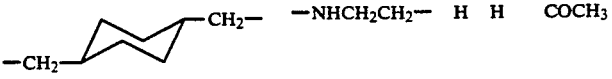 | —NHCH$_2$CH$_2$— | H | H | COCH$_3$ |
| 1105 | Cl | X | 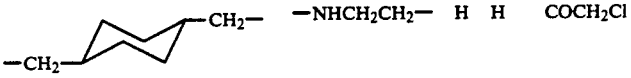 | —NHCH$_2$CH$_2$— | H | H | COCH$_2$Cl |
| 1106 | Cl | X | 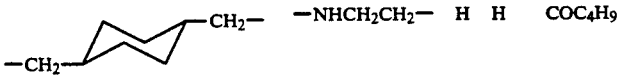 | —NHCH$_2$CH$_2$— | H | H | COC$_4$H$_9$ |
| 1107 | Cl | X | 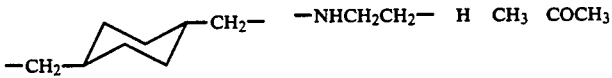 | —NHCH$_2$CH$_2$— | H | CH$_3$ | COCH$_3$ |
| 1108 | Cl | X | 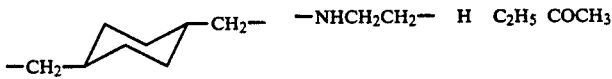 | —NHCH$_2$CH$_2$— | H | C$_2$H$_5$ | COCH$_3$ |
| 1109 | Cl | X | 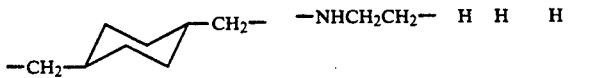 | —NHCH$_2$CH$_2$— | H | H | H |
| 1110 | Cl | X | 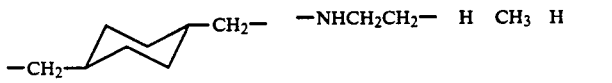 | —NHCH$_2$CH$_2$— | H | CH$_3$ | H |
| 1111 | Cl | X | 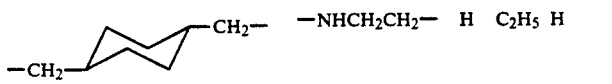 | —NHCH$_2$CH$_2$— | H | C$_2$H$_5$ | H |
| 1112 | Cl | X | 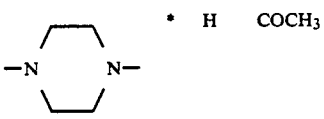 | 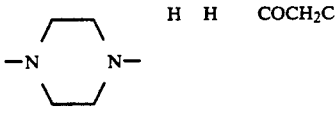 | * | H | COCH$_3$ |
| 1113 | Cl | X | 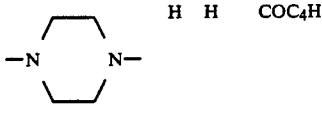 | 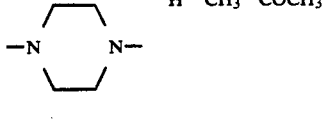 | H | H | COCH$_2$Cl |
| 1114 | Cl | X | 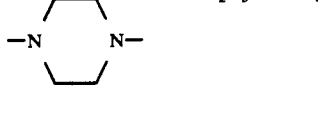 | 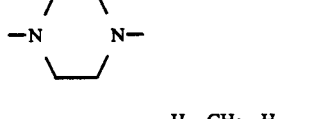 | H | H | COC$_4$H$_9$ |
| 1115 | Cl | X | 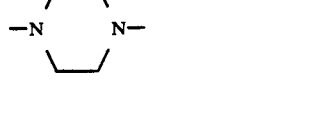 |  | H | CH$_3$ | COCH$_3$ |
| 1116 | Cl | X |  |  | H | C$_2$H$_5$ | COCH$_3$ |
| 1117 | Cl | X |  |  | * | H | H |
| 1118 | Cl | X |  |  | H | CH$_3$ | H |

-continued

| | | | | | | | |
|---|---|---|---|---|---|---|---|
| 1119 | Cl | X | 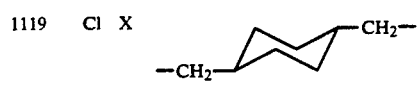 | 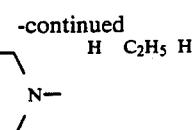 | H | C$_2$H$_5$ | H |
| 1120 | X | Cl | single bond | —NH— | H | H | COCH$_3$ |
| 1121 | X | Cl | single bond | —NH— | H | H | COCH$_2$Cl |
| 1122 | X | Cl | single bond | —NH— | H | H | COC$_4$H$_9$ |
| 1123 | X | Cl | single bond | —NH— | H | CH$_3$ | COCH$_3$ |
| 1124 | X | Cl | single bond | —NH— | H | C$_2$H$_5$ | COCH$_3$ |
| 1125 | X | Cl | single bond | —NH— | H | H | H |
| 1126 | X | Cl | single bond | —NH— | H | CH$_3$ | H |
| 1127 | X | Cl | single bond | —NH— | H | C$_2$H$_5$ | H |
| 1128 | X | Cl | single bond | —NHCH$_2$CH$_2$— | H | H | COCH$_3$ |
| 1129 | X | Cl | single bond | —NHCH$_2$CH$_2$— | H | H | COCH$_2$Cl |
| 1130 | X | Cl | single bond | —NHCH$_2$CH$_2$— | H | H | COC$_4$H$_9$ |
| 1131 | X | Cl | single bond | —NHCH$_2$CH$_2$— | H | CH$_3$ | COCH$_3$ |
| 1132 | X | Cl | single bond | —NHCH$_2$CH$_2$— | H | C$_2$H$_5$ | COCH$_3$ |
| 1133 | X | Cl | single bond | —NHCH$_2$CH$_2$— | H | H | H |
| 1134 | X | Cl | single bond | —NHCH$_2$CH$_2$— | H | CH$_3$ | H |
| 1135 | X | Cl | single bond | —NHCH$_2$CH$_2$— | H | C$_2$H$_5$ | H |
| 1136 | X | Cl | single bond | 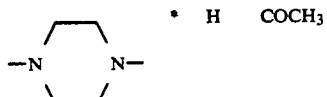 | * | H | COCH$_3$ |
| 1137 | X | Cl | single bond | 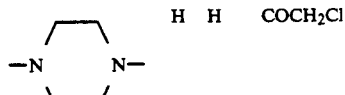 | H | H | COCH$_2$Cl |
| 1138 | X | Cl | single bond | 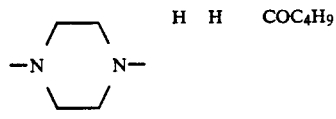 | H | H | COC$_4$H$_9$ |
| 1139 | X | Cl | single bond | 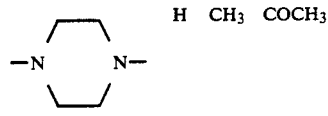 | H | CH$_3$ | COCH$_3$ |
| 1140 | X | Cl | single bond | 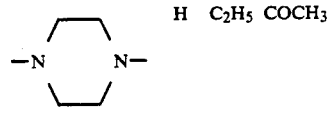 | H | C$_2$H$_5$ | COCH$_3$ |
| 1141 | X | Cl | single bond | 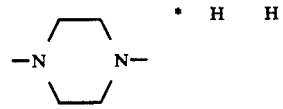 | * | H | H |
| 1142 | X | Cl | single bond | 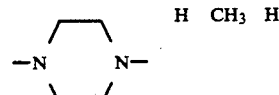 | H | CH$_3$ | H |
| 1143 | X | Cl | single bond | 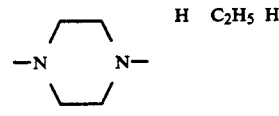 | H | C$_2$H$_5$ | H |
| 1144 | X | Cl | CH$_2$ | —NH— | H | H | COCH$_2$Cl |
| 1145 | X | Cl | CH$_2$ | —NH— | H | H | COC$_4$H$_9$ |
| 1146 | X | Cl | CH$_2$ | —NH— | H | CH$_3$ | COCH$_3$ |
| 1147 | X | Cl | CH$_2$ | —NH— | H | C$_2$H$_5$ | COCH$_3$ |
| 1148 | X | Cl | CH$_2$ | —NH— | H | H | H |
| 1149 | X | Cl | CH$_2$ | —NH— | H | CH$_3$ | H |
| 1150 | X | Cl | CH$_2$ | —NH— | H | C$_2$H$_5$ | H |
| 1151 | X | Cl | CH$_2$ | —NHCH$_2$CH$_2$— | H | H | COCH$_3$ |
| 1152 | X | Cl | CH$_2$ | —NHCH$_2$CH$_2$— | H | H | COCH$_2$Cl |
| 1153 | X | Cl | CH$_2$ | —NHCH$_2$CH$_2$— | H | H | COC$_4$H$_9$ |
| 1154 | X | Cl | CH$_2$ | —NHCH$_2$CH$_2$— | H | CH$_3$ | COCH$_3$ |
| 1155 | X | Cl | CH$_2$ | —NHCH$_2$CH$_2$— | H | C$_2$H$_5$ | COCH$_3$ |

-continued

| | | | | | | | | |
|---|---|---|---|---|---|---|---|---|
| 1156 | X | Cl | CH₂ | —NHCH₂CH₂— | | H | H | H |
| 1157 | X | Cl | CH₂ | —NHCH₂CH₂— | | H | CH₃ | H |
| 1158 | X | Cl | CH₂ | —NHCH₂CH₂— | | H | C₂H₅ | H |
| 1159 | X | Cl | CH₂ |  | | * | H | COCH₃ |
| 1160 | X | Cl | CH₂ | 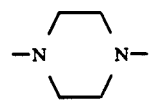 | | H | H | COCH₂Cl |
| 1161 | X | Cl | CH₂ | 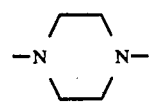 | | H | H | COC₄H₉ |
| 1162 | X | Cl | CH₂ | 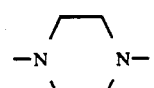 | | H | CH₃ | COCH₃ |
| 1163 | X | Cl | CH₂ | 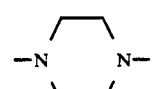 | | H | C₂H₅ | COCH₃ |
| 1164 | X | Cl | CH₂ | 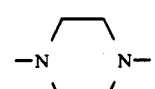 | | * | H | H |
| 1165 | X | Cl | CH₂ | 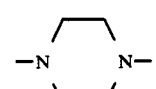 | | H | CH₃ | H |
| 1166 | X | Cl | CH₂ | 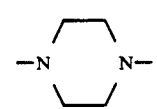 | | H | C₂H₅ | H |
| 1167 | X | Cl | CH₂CH₂ | —NH— | | H | H | COCH₃ |
| 1168 | X | Cl | CH₂CH₂ | —NH— | | H | H | COCH₂Cl |
| 1169 | X | Cl | CH₂CH₂ | —NH— | | H | H | COC₄H₉ |
| 1170 | X | Cl | CH₂CH₂ | —NH— | | H | CH₃ | COCH₃ |
| 1171 | X | Cl | CH₂CH₂ | —NH— | | H | C₂H₅ | COCH₃ |
| 1172 | X | Cl | CH₂CH₂ | —NH— | | H | H | H |
| 1173 | X | Cl | CH₂CH₂ | —NH— | | H | CH₃ | H |
| 1174 | X | Cl | CH₂CH₂ | —NH— | | H | C₂H₅ | H |
| 1175 | X | Cl | CH₂CH₂ | —NHCH₂CH₂— | | H | H | COCH₃ |
| 1176 | X | Cl | CH₂CH₂ | —NHCH₂CH₂— | | H | H | COCH₂Cl |
| 1177 | X | Cl | CH₂CH₂ | —NHCH₂CH₂— | | H | H | COC₄H₉ |
| 1178 | X | Cl | CH₂CH₂ | —NHCH₂CH₂— | | H | CH₃ | COCH₃ |
| 1179 | X | Cl | CH₂CH₂ | —NHCH₂CH₂— | | H | C₂H₅ | COCH₃ |
| 1180 | X | Cl | CH₂CH₂ | —NHCH₂CH₂— | | H | H | H |
| 1181 | X | Cl | CH₂CH₂ | —NHCH₂CH₂— | | H | CH₃ | H |
| 1182 | X | Cl | CH₂CH₂ | —NHCH₂CH₂— | | H | C₂H₅ | H |
| 1183 | X | Cl | CH₂CH₂ | 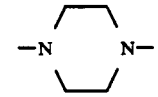 | | * | H | COCH₃ |
| 1184 | X | Cl | CH₂CH₂ | 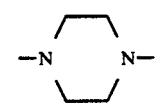 | | H | H | COCH₂Cl |

-continued

| | | | | | | | | |
|---|---|---|---|---|---|---|---|---|
| 1185 | X | Cl | CH$_2$CH$_2$ | 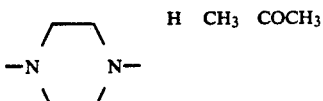 | | H | H | COC$_4$H$_9$ |
| 1186 | X | Cl | CH$_2$CH$_2$ | 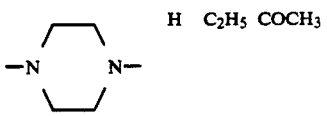 | | H | CH$_3$ | COCH$_3$ |
| 1187 | X | Cl | CH$_2$CH$_2$ | 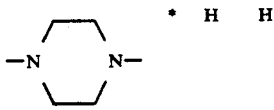 | | H | C$_2$H$_5$ | COCH$_3$ |
| 1188 | X | Cl | CH$_2$CH$_2$ | 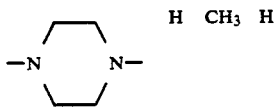 | | * | H | H |
| 1189 | X | Cl | CH$_2$CH$_2$ | 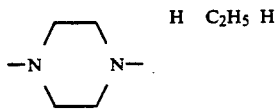 | | H | CH$_3$ | H |
| 1190 | X | Cl | CH$_2$CH$_2$ | 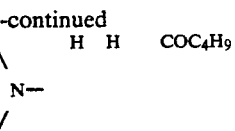 | | H | C$_2$H$_5$ | H |
| 1191 | X | Cl | C$_3$H$_6$(n) | —NH— | | H | H | COCH$_3$ |
| 1192 | X | Cl | C$_3$H$_6$(n) | —NH— | | H | H | COCH$_2$Cl |
| 1193 | X | Cl | C$_3$H$_6$(n) | —NH— | | H | H | COC$_4$H$_9$ |
| 1194 | X | Cl | C$_3$H$_6$(n) | —NH— | | H | CH$_3$ | COCH$_3$ |
| 1195 | X | Cl | C$_3$H$_6$(n) | —NH— | | H | C$_2$H$_5$ | COCH$_3$ |
| 1196 | X | Cl | C$_3$H$_6$(n) | —NH— | | H | H | H |
| 1197 | X | Cl | C$_3$H$_6$(n) | —NH— | | H | CH$_3$ | H |
| 1198 | X | Cl | C$_3$H$_6$(n) | —NH— | | H | C$_2$H$_5$ | H |
| 1199 | X | Cl | C$_3$H$_6$(n) | —NHCH$_2$CH$_2$— | | H | H | COCH$_3$ |
| 1200 | X | Cl | C$_3$H$_6$(n) | —NHCH$_2$CH$_2$— | | H | H | COCH$_2$Cl |
| 1201 | X | Cl | C$_3$H$_6$(n) | —NHCH$_2$CH$_2$— | | H | H | COC$_4$H$_9$ |
| 1202 | X | Cl | C$_3$H$_6$(n) | —NHCH$_2$CH$_2$— | | H | CH$_3$ | COCH$_3$ |
| 1203 | X | Cl | C$_3$H$_6$(n) | —NHCH$_2$CH$_2$— | | H | C$_2$H$_5$ | COCH$_3$ |
| 1204 | X | Cl | C$_3$H$_6$(n) | —NHCH$_2$CH$_2$— | | H | H | H |
| 1205 | X | Cl | C$_3$H$_6$(n) | —NHCH$_2$CH$_2$— | | H | CH$_3$ | H |
| 1206 | X | Cl | C$_3$H$_6$(n) | —NHCH$_2$CH$_2$— | | H | C$_2$H$_5$ | H |
| 1207 | X | Cl | C$_3$H$_6$(n) | 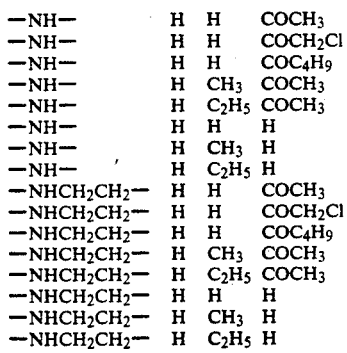 | | * | H | COCH$_3$ |
| 1208 | X | Cl | C$_3$H$_6$(n) | 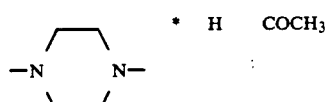 | | H | H | COCH$_2$Cl |
| 1209 | X | Cl | C$_3$H$_6$(n) | 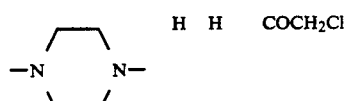 | | H | H | COC$_4$H$_9$ |
| 1210 | X | Cl | C$_3$H$_6$(n) | 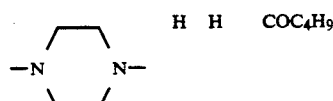 | | H | CH$_3$ | COCH$_3$ |
| 1211 | X | Cl | C$_3$H$_6$(n) | 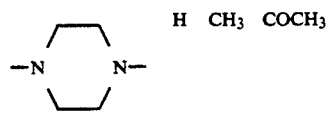 | | H | C$_2$H$_5$ | COCH$_3$ |

-continued

| | | | | | | | |
|---|---|---|---|---|---|---|---|
| 1212 | X | Cl | C₃H₆(n) | piperazine | * | H | H |
| 1213 | X | Cl | C₃H₆(n) | piperazine | H | CH₃ | H |
| 1214 | X | Cl | C₃H₆(n) | piperazine | H | C₂H₅ | H |
| 1215 | X | Cl | C₄H₈(n) | —NH— | H | H | COCH₃ |
| 1216 | X | Cl | C₄H₈(n) | —NH— | H | H | COCH₂Cl |
| 1217 | X | Cl | C₄H₈(n) | —NH— | H | H | COC₄H₉ |
| 1218 | X | Cl | C₄H₈(n) | —NH— | H | CH₃ | COCH₃ |
| 1219 | X | Cl | C₄H₈(n) | —NH— | H | C₂H₅ | COCH₃ |
| 1220 | X | Cl | C₄H₈(n) | —NH— | H | H | H |
| 1221 | X | Cl | C₄H₈(n) | —NH— | H | CH₃ | H |
| 1222 | X | Cl | C₄H₈(n) | —NH— | H | C₂H₅ | H |
| 1223 | X | Cl | C₄H₈(n) | —NHCH₂CH₂— | H | H | COCH₃ |
| 1224 | X | Cl | C₄H₈(n) | —NHCH₂CH₂— | H | H | COCH₂Cl |
| 1225 | X | Cl | C₄H₈(n) | —NHCH₂CH₂— | H | H | COC₄H₉ |
| 1226 | X | Cl | C₄H₈(n) | —NHCH₂CH₂— | H | CH₃ | COCH₃ |
| 1227 | X | Cl | C₄H₈(n) | —NHCH₂CH₂— | H | C₂H₅ | COCH₃ |
| 1228 | X | Cl | C₄H₈(n) | —NHCH₂CH₂— | H | H | H |
| 1229 | X | Cl | C₄H₈(n) | —NHCH₂CH₂— | H | CH₃ | H |
| 1230 | X | Cl | C₄H₈(n) | —NHCH₂CH₂— | H | C₂H₅ | H |
| 1231 | X | Cl | C₄H₈(n) | piperazine | * | H | COCH₃ |
| 1232 | X | Cl | C₄H₈(n) | piperazine | H | H | COCH₂Cl |
| 1233 | X | Cl | C₄H₈(n) | piperazine | H | H | COC₄H₉ |
| 1234 | X | Cl | C₄H₈(n) | piperazine | H | CH₃ | COCH₃ |
| 1235 | X | Cl | C₄H₈(n) | piperazine | H | C₂H₅ | COCH₃ |
| 1236 | X | Cl | C₄H₈(n) | piperazine | * | H | H |
| 1237 | X | Cl | C₄H₈(n) | piperazine | H | CH₃ | H |

| | | | | | | | |
|---|---|---|---|---|---|---|---|
| 1238 | X | Cl | C₄H₈(n) | 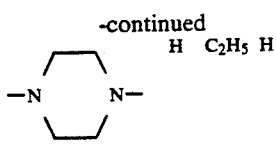 | H | C₂H₅ | H |
| 1239 | X | Cl | 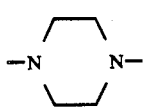 | —NH— | H | H | COCH₃ |
| 1240 | X | Cl | 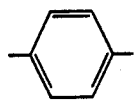 | —NH— | H | H | COCH₂Cl |
| 1241 | X | Cl | 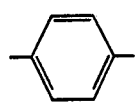 | —NH— | H | H | COC₄H₉ |
| 1242 | X | Cl | 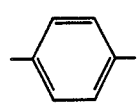 | —NH— | H | CH₃ | COCH₃ |
| 1243 | X | Cl | 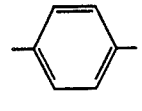 | —NH— | H | C₂H₅ | COCH₃ |
| 1244 | X | Cl | 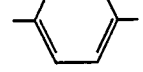 | —NH— | H | H | H |
| 1245 | X | Cl | 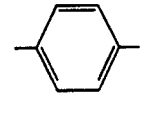 | —NH— | H | CH₃ | H |
| 1246 | X | Cl | 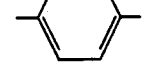 | —NH— | H | C₂H₅ | H |
| 1247 | X | Cl | 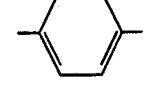 | —NHCH₂CH₂— | H | H | COCH₃ |
| 1248 | X | Cl | 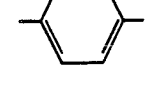 | —NHCH₂CH₂— | H | H | COCH₂Cl |
| 1249 | X | Cl | 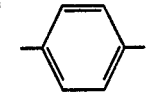 | —NHCH₂CH₂— | H | H | COC₄H₉ |
| 1250 | X | Cl | 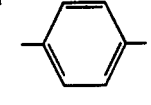 | —NHCH₂CH₂— | H | CH₃ | COCH₃ |
| 1251 | X | Cl | 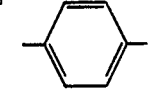 | —NHCH₂CH₂— | H | C₂H₅ | COCH₃ |

| | | | | | | | |
|---|---|---|---|---|---|---|---|
| 1252 | X | Cl |  | —NHCH$_2$CH$_2$— | H | H | H |
| 1253 | X | Cl |  | —NHCH$_2$CH$_2$— | H | CH$_3$ | H |
| 1254 | X | Cl |  | —NHCH$_2$CH$_2$— | H | C$_2$H$_5$ | H |
| 1255 | X | Cl |  |  | * | H | COCH$_3$ |
| 1256 | X | Cl | |  | H | H | COCH$_2$Cl |
| 1257 | X | Cl | | 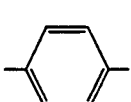 | H | H | COC$_4$H$_9$ |
| 1258 | X | Cl | | 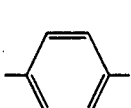 | H | CH$_3$ | COCH$_3$ |
| 1259 | X | Cl | |  | H | C$_2$H$_5$ | COCH$_3$ |
| 1260 | X | Cl | |  | * | H | H |
| 1261 | X | Cl | | 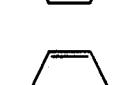 | H | CH$_3$ | H |
| 1262 | X | Cl | | 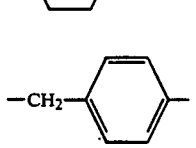 | H | C$_2$H$_5$ | H |
| 1263 | X | Cl | 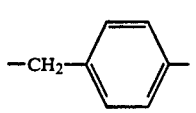 | —NH— | H | H | COCH$_3$ |
| 1264 | X | Cl | —CH$_2$— | —NH— | H | H | COCH$_2$Cl |

-continued
| | | | | | | | |
|---|---|---|---|---|---|---|---|
| 1265 | X | Cl | 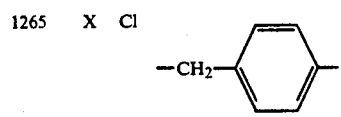 | —NH— | H | H | COC₄H₉ |
| 1266 | X | Cl | 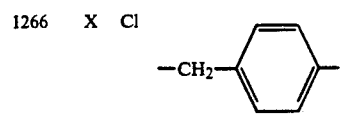 | —NH— | H | CH₃ | COCH₃ |
| 1267 | X | Cl | 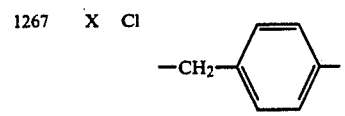 | —NH— | H | C₂H₅ | COCH₃ |
| 1268 | X | Cl | 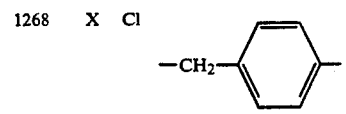 | —NH— | H | H | H |
| 1269 | X | Cl | 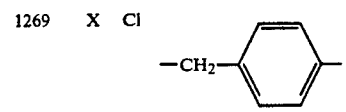 | —NH— | H | CH₃ | H |
| 1270 | X | Cl | 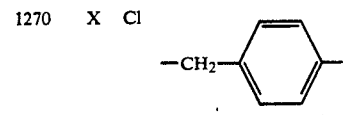 | —NH— | H | C₂H₅ | H |
| 1271 | X | Cl | 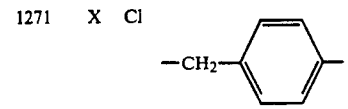 | —NHCH₂CH₂— | H | H | COCH₃ |
| 1272 | X | Cl | 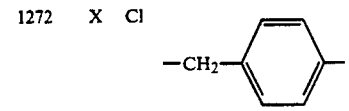 | —NHCH₂CH₂— | H | H | COCH₂Cl |
| 1273 | X | Cl | 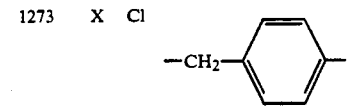 | —NHCH₂CH₂— | H | H | COC₄H₉ |
| 1274 | X | Cl | 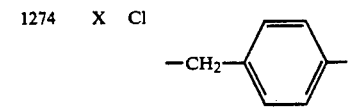 | —NHCH₂CH₂— | H | CH₃ | COCH₃ |
| 1275 | X | Cl | 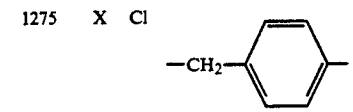 | —NHCH₂CH₂— | H | C₂H₅ | COCH₃ |
| 1276 | X | Cl | 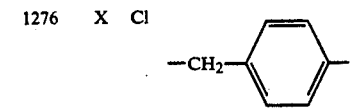 | —NHCH₂CH₂— | H | H | H |
| 1277 | X | Cl | 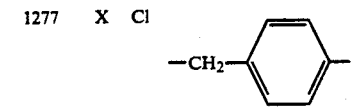 | —NHCH₂CH₂— | H | CH₃ | H |
| 1278 | X | Cl | 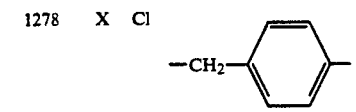 | —NHCH₂CH₂— | H | C₂H₅ | H |

| | | | | | | |
|---|---|---|---|---|---|---|
| 1279 | X Cl | —CH₂—⟨C₆H₄⟩— | —N(C₄H₈)N— | * | H | COCH₃ |
| 1280 | X Cl | —CH₂—⟨C₆H₄⟩— | —N(C₄H₈)N— | H | H | COCH₂Cl |
| 1281 | X Cl | —CH₂—⟨C₆H₄⟩— | —N(C₄H₈)N— | H | H | COC₄H₉ |
| 1282 | X Cl | —CH₂—⟨C₆H₄⟩— | —N(C₄H₈)N— | H | CH₃ | COCH₃ |
| 1283 | X Cl | —CH₂—⟨C₆H₄⟩— | —N(C₄H₈)N— | H | C₂H₅ | COCH₃ |
| 1284 | X Cl | —CH₂—⟨C₆H₄⟩— | —N(C₄H₈)N— | * | H | H |
| 1285 | X Cl | —CH₂—⟨C₆H₄⟩— | —N(C₄H₈)N— | H | CH₃ | H |
| 1286 | X Cl | —CH₂—⟨C₆H₄⟩— | —N(C₄H₈)N— | H | C₂H₅ | H |
| 1287 | X Cl | —CH₂CH₂—⟨C₆H₄⟩— | —NH— | H | H | COCH₃ |
| 1288 | X Cl | —CH₂CH₂—⟨C₆H₄⟩— | —NH— | H | H | COCH₂Cl |
| 1289 | X Cl | —CH₂CH₂—⟨C₆H₄⟩— | —NH— | H | H | COC₄H₉ |
| 1290 | X Cl | —CH₂CH₂—⟨C₆H₄⟩— | —NH— | H | CH₃ | COCH₃ |
| 1291 | X Cl | —CH₂CH₂—⟨C₆H₄⟩— | —NH— | H | C₂H₅ | COCH₃ |

-continued
| | | | | | | | |
|---|---|---|---|---|---|---|---|
| 1292 | X | Cl | 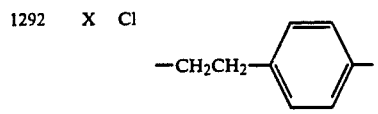 | —NH— | H | H | H |
| 1293 | X | Cl | 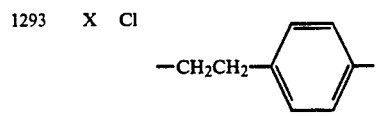 | —NH— | H | CH₃ | H |
| 1294 | X | Cl | 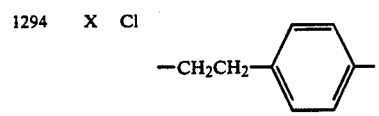 | —NH— | H | C₂H₅ | H |
| 1295 | X | Cl | 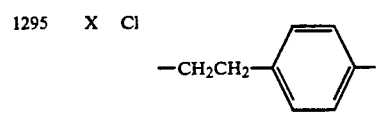 | —NHCH₂CH₂— | H | H | COCH₃ |
| 1296 | X | Cl | 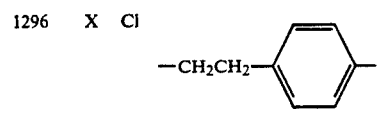 | —NHCH₂CH₂— | H | H | COCH₂Cl |
| 1297 | X | Cl | 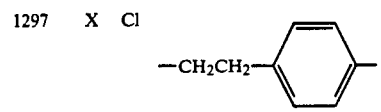 | —NHCH₂CH₂— | H | H | COC₄H₉ |
| 1298 | X | Cl | 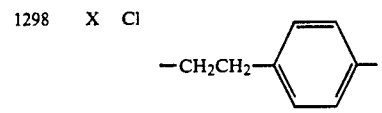 | —NHCH₂CH₂— | H | CH₃ | COCH₃ |
| 1299 | X | Cl | 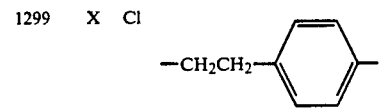 | —NHCH₂CH₂— | H | C₂H₅ | COCH₃ |
| 1300 | X | Cl | 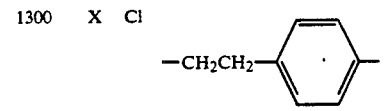 | —NHCH₂CH₂— | H | H | H |
| 1301 | X | Cl | 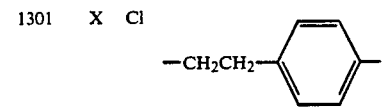 | —NHCH₂CH₂— | H | CH₃ | H |
| 1302 | X | Cl | 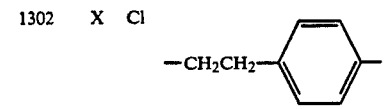 | —NHCH₂CH₂— | H | C₂H₅ | H |
| 1303 | X | Cl | 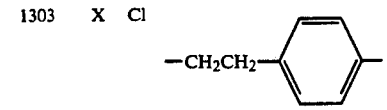 | 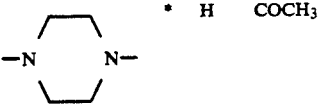 | * | H | COCH₃ |
| 1304 | X | Cl | 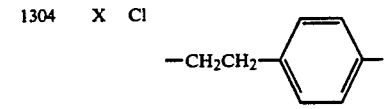 | 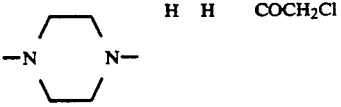 | H | H | COCH₂Cl |
| 1305 | X | Cl | 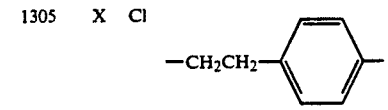 | 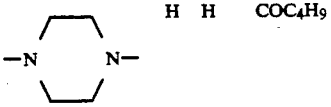 | H | H | COC₄H₉ |

-continued

| | | | | | | | |
|---|---|---|---|---|---|---|---|
| 1306 | X | Cl | -CH₂CH₂-C₆H₄- | -N(piperazine)N- | H | CH₃ | COCH₃ |
| 1307 | X | Cl | -CH₂CH₂-C₆H₄- | -N(piperazine)N- | H | C₂H₅ | COCH₃ |
| 1308 | X | Cl | -CH₂CH₂-C₆H₄- | -N(piperazine)N- | • | H | H |
| 1309 | X | Cl | -CH₂CH₂-C₆H₄- | -N(piperazine)N- | H | CH₃ | H |
| 1310 | X | Cl | -CH₂CH₂-C₆H₄- | -N(piperazine)N- | H | C₂H₅ | H |
| 1311 | X | Cl | -C₆H₄-CH₂- | -NH- | H | H | COCH₃ |
| 1312 | X | Cl | -C₆H₄-CH₂- | -NH- | H | H | COCH₂Cl |
| 1313 | X | Cl | -C₆H₄-CH₂- | -NH- | H | H | COC₄H₉ |
| 1314 | X | Cl | -C₆H₄-CH₂- | -NH- | H | CH₃ | COCH₃ |
| 1315 | X | Cl | -C₆H₄-CH₂- | -NH- | H | C₂H₅ | COCH₃ |
| 1316 | X | Cl | -C₆H₄-CH₂- | -NH- | H | H | H |
| 1317 | X | Cl | -C₆H₄-CH₂- | -NH- | H | CH₃ | H |
| 1318 | X | Cl | -C₆H₄-CH₂- | -NH- | H | C₂H₅ | H |

-continued

| | | | | | | |
|---|---|---|---|---|---|---|
| 1319 | X Cl | 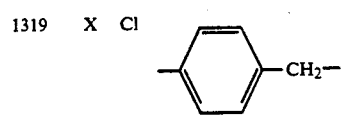 | —NHCH$_2$CH$_2$— | H | H | COCH$_3$ |
| 1320 | X Cl | 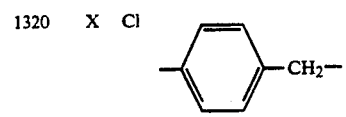 | —NHCH$_2$CH$_2$— | H | H | COCH$_2$Cl |
| 1321 | X Cl | 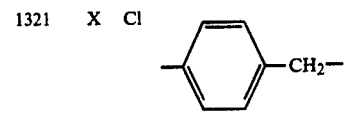 | —NHCH$_2$CH$_2$— | H | H | COC$_4$H$_9$ |
| 1322 | X Cl | 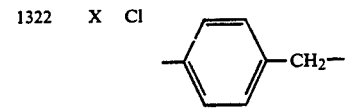 | —NHCH$_2$CH$_2$— | H | CH$_3$ | COCH$_3$ |
| 1323 | X Cl | 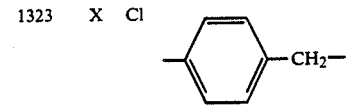 | —NHCH$_2$CH$_2$— | H | C$_2$H$_5$ | COCH$_3$ |
| 1324 | X Cl | 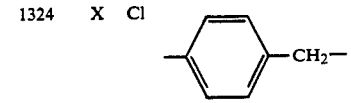 | —NHCH$_2$CH$_2$— | H | H | H |
| 1325 | X Cl | 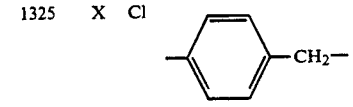 | —NHCH$_2$CH$_2$— | H | CH$_3$ | H |
| 1326 | X Cl | 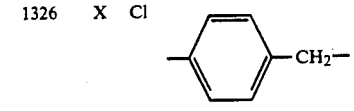 | —NHCH$_2$CH$_2$— | H | C$_2$H$_5$ | H |
| 1327 | X Cl | 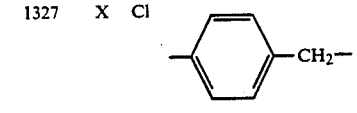 | piperazine | * | H | COCH$_3$ |
| 1328 | X Cl | 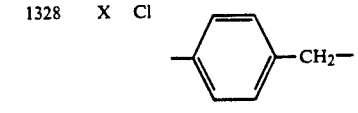 | piperazine | H | H | COCH$_2$Cl |
| 1329 | X Cl | 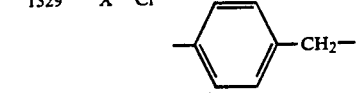 | piperazine | H | H | COC$_4$H$_9$ |
| 1330 | X Cl | 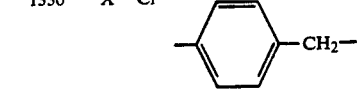 | piperazine | H | CH$_3$ | COCH$_3$ |
| 1331 | X Cl | 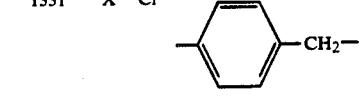 | piperazine | H | C$_2$H$_5$ | COCH$_3$ |
| 1332 | X Cl | 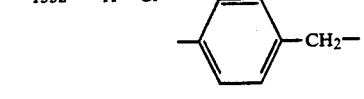 | piperazine | * | H | H |

| | | | | | | |
|---|---|---|---|---|---|---|
| 1333 | X Cl | 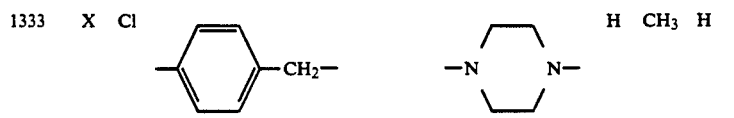 | −N⟨piperazine⟩N− | H | CH$_3$ | H |
| 1334 | X Cl | 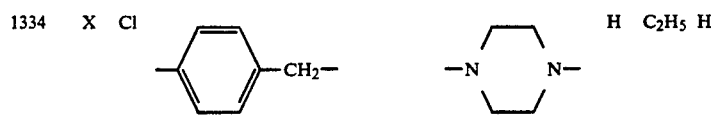 | −N⟨piperazine⟩N− | H | C$_2$H$_5$ | H |
| 1335 | X Cl | 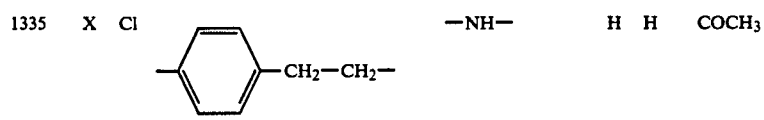 | −NH− | H | H | COCH$_3$ |
| 1336 | X Cl | 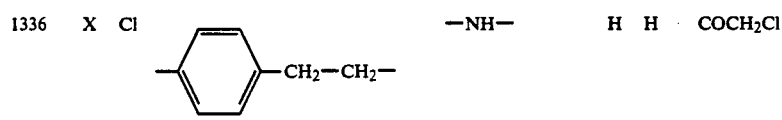 | −NH− | H | H | COCH$_2$Cl |
| 1337 | X Cl | 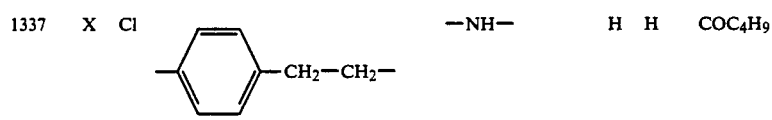 | −NH− | H | H | COC$_4$H$_9$ |
| 1338 | X Cl | 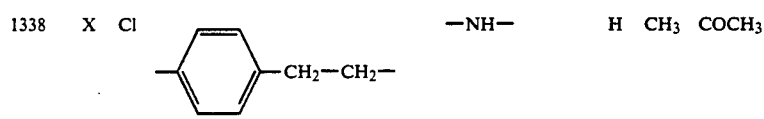 | −NH− | H | CH$_3$ | COCH$_3$ |
| 1339 | X Cl | 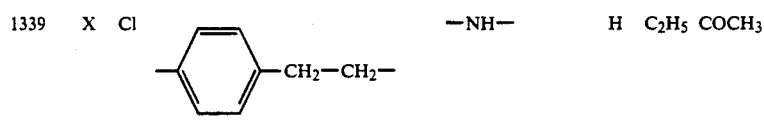 | −NH− | H | C$_2$H$_5$ | COCH$_3$ |
| 1340 | X Cl | 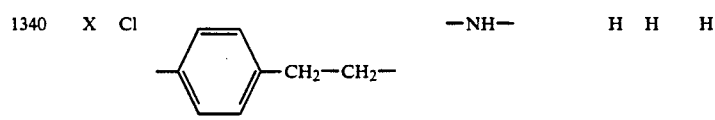 | −NH− | H | H | H |
| 1341 | X Cl | 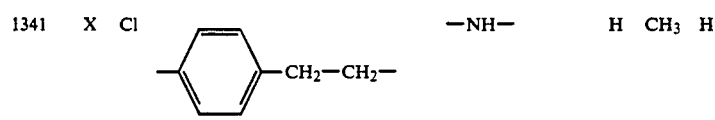 | −NH− | H | CH$_3$ | H |
| 1342 | X Cl | 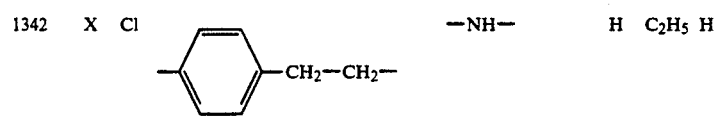 | −NH− | H | C$_2$H$_5$ | H |
| 1343 | X Cl | 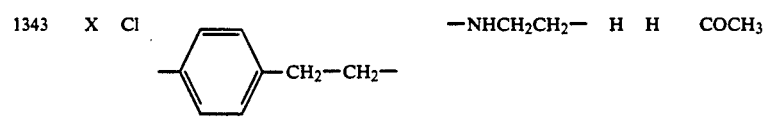 | −NHCH$_2$CH$_2$− | H | H | COCH$_3$ |
| 1344 | X Cl | 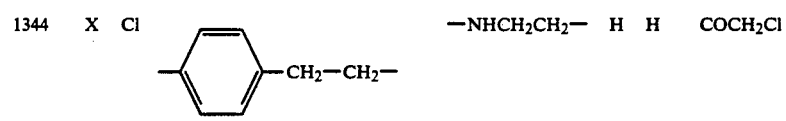 | −NHCH$_2$CH$_2$− | H | H | COCH$_2$Cl |
| 1345 | X Cl | 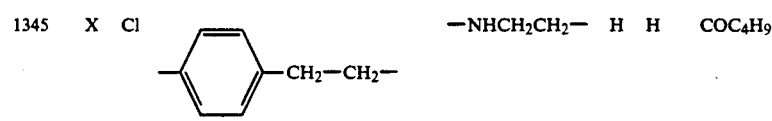 | −NHCH$_2$CH$_2$− | H | H | COC$_4$H$_9$ |

-continued
| | | | | | | | |
|---|---|---|---|---|---|---|---|
| 1346 | X Cl | 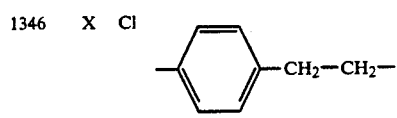 | —NHCH$_2$CH$_2$— | H | CH$_3$ | COCH$_3$ | |
| 1347 | X Cl | 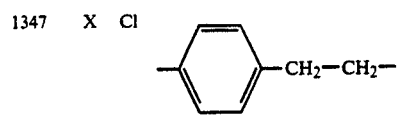 | —NHCH$_2$CH$_2$— | H | C$_2$H$_5$ | COCH$_3$ | |
| 1348 | X Cl | 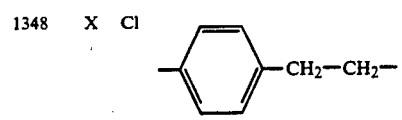 | —NHCH$_2$CH$_2$— | H | H | H | |
| 1349 | X Cl | 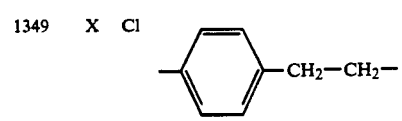 | —NHCH$_2$CH$_2$— | H | CH$_3$ | H | |
| 1350 | X Cl | 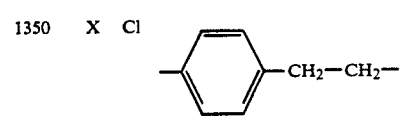 | —NHCH$_2$CH$_2$— | H | C$_2$H$_5$ | H | |
| 1351 | X Cl | 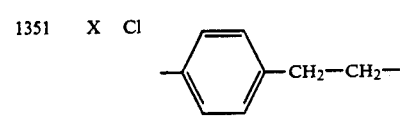 | 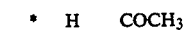 | * | H | COCH$_3$ | |
| 1352 | X Cl | 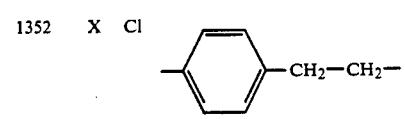 |  | H | H | COCH$_2$Cl | |
| 1353 | X Cl | 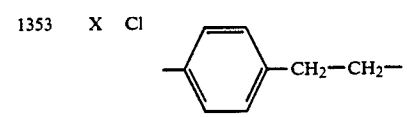 |  | H | H | COC$_4$H$_9$ | |
| 1354 | X Cl | 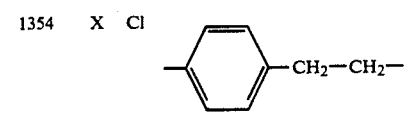 | 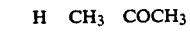 | H | CH$_3$ | COCH$_3$ | |
| 1355 | X Cl | 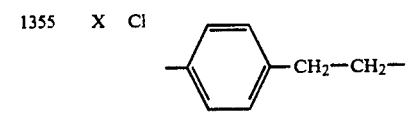 | 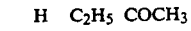 | H | C$_2$H$_5$ | COCH$_3$ | |
| 1356 | X Cl | 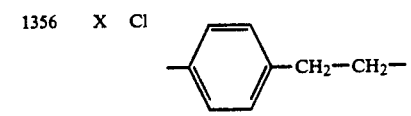 | 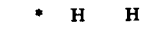 | * | H | H | |
| 1357 | X Cl | 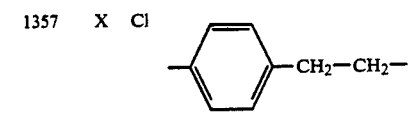 |  | H | CH$_3$ | H | |
| 1358 | X Cl | 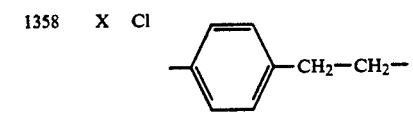 |  | H | C$_2$H$_5$ | H | |
| 1359 | X Cl | 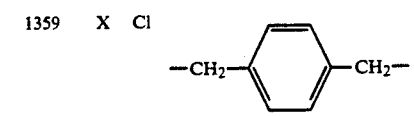 | —NH— | H | H | COCH$_3$ | |

-continued

| | | | | | | | |
|---|---|---|---|---|---|---|---|
| 1360 | X | Cl | -CH$_2$-C$_6$H$_4$-CH$_2$- | -NH- | H | H | COCH$_2$Cl |
| 1361 | X | Cl | -CH$_2$-C$_6$H$_4$-CH$_2$- | -NH- | H | H | COC$_4$H$_9$ |
| 1362 | X | Cl | -CH$_2$-C$_6$H$_4$-CH$_2$- | -NH- | H | CH$_3$ | COCH$_3$ |
| 1363 | X | Cl | -CH$_2$-C$_6$H$_4$-CH$_2$- | -NH- | H | C$_2$H$_5$ | COCH$_3$ |
| 1364 | X | Cl | -CH$_2$-C$_6$H$_4$-CH$_2$- | -NH- | H | H | H |
| 1365 | X | Cl | -CH$_2$-C$_6$H$_4$-CH$_2$- | -NH- | H | CH$_3$ | H |
| 1366 | X | Cl | -CH$_2$-C$_6$H$_4$-CH$_2$- | -NH- | H | C$_2$H$_5$ | H |
| 1367 | X | Cl | -CH$_2$-C$_6$H$_4$-CH$_2$- | -NHCH$_2$CH$_2$- | H | H | COCH$_3$ |
| 1368 | X | Cl | -CH$_2$-C$_6$H$_4$-CH$_2$- | -NHCH$_2$CH$_2$- | H | H | COCH$_2$Cl |
| 1369 | X | Cl | -CH$_2$-C$_6$H$_4$-CH$_2$- | -NHCH$_2$CH$_2$- | H | H | COC$_4$H$_9$ |
| 1370 | X | Cl | -CH$_2$-C$_6$H$_4$-CH$_2$- | -NHCH$_2$CH$_2$- | H | CH$_3$ | COCH$_3$ |
| 1371 | X | Cl | -CH$_2$-C$_6$H$_4$-CH$_2$- | -NHCH$_2$CH$_2$- | H | C$_2$H$_5$ | COCH$_3$ |
| 1372 | X | Cl | -CH$_2$-C$_6$H$_4$-CH$_2$- | -NHCH$_2$CH$_2$- | H | H | H |

-continued
| | | | | | | | |
|---|---|---|---|---|---|---|---|
| 1373 | X | Cl | 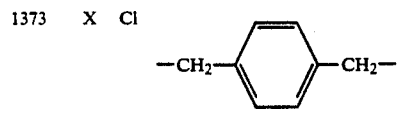 | —NHCH₂CH₂— | H | CH₃ | H |
| 1374 | X | Cl | 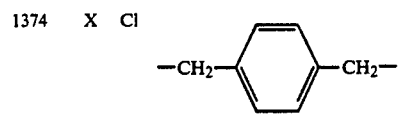 | —NHCH₂CH₂— | H | C₂H₅ | H |
| 1375 | X | Cl | 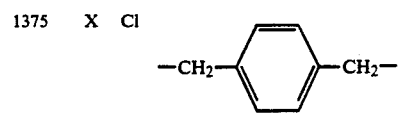 | 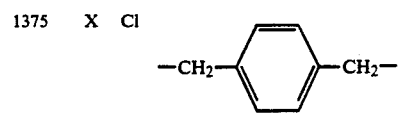 | * | H | COCH₃ |
| 1376 | X | Cl | 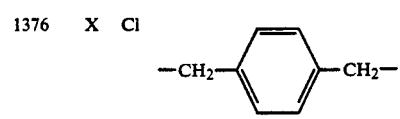 | 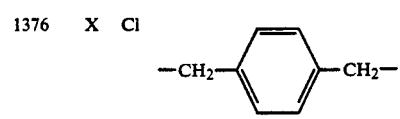 | H | H | COCH₂Cl |
| 1377 | X | Cl | 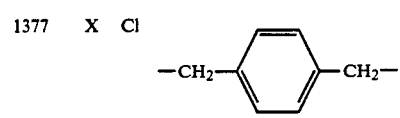 | 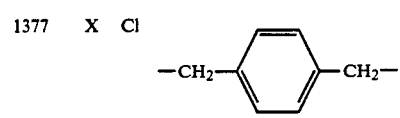 | H | H | COC₄H₉ |
| 1378 | X | Cl | 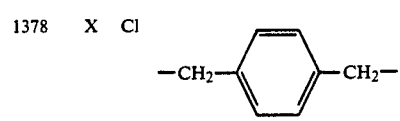 | 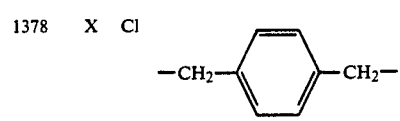 | H | CH₃ | COCH₃ |
| 1379 | X | Cl | 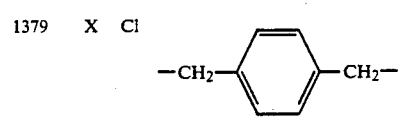 | 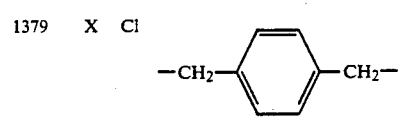 | H | C₂H₅ | COCH₃ |
| 1380 | X | Cl | 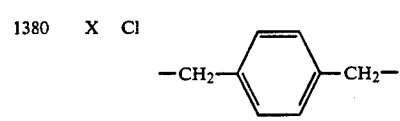 | 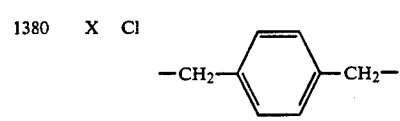 | * | H | H |
| 1381 | X | Cl | 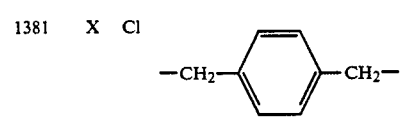 | 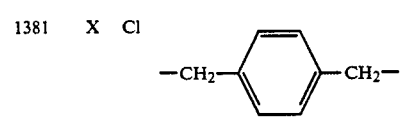 | H | CH₃ | H |
| 1382 | X | Cl | 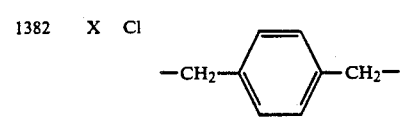 | 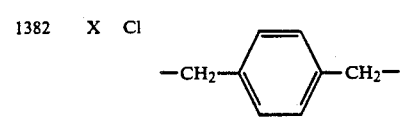 | H | C₂H₅ | H |
| 1383 | X | Cl |  | —NH— | H | H | COCH₃ |
| 1384 | X | Cl |  | —NH— | H | H | COCH₂Cl |
| 1385 | X | Cl |  | —NH— | H | H | COC₄H₉ |
| 1386 | X | Cl |  | —NH— | H | CH₃ | COCH₃ |
| 1387 | X | Cl | 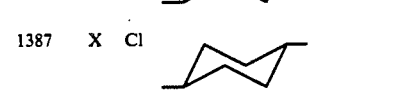 | —NH— | H | C₂H₅ | COCH₃ |
| 1388 | X | Cl |  | —NH— | H | H | H |

-continued

| | | | | | | | |
|---|---|---|---|---|---|---|---|
| 1389 | X | Cl | (cyclohexyl) | —NH— | H | CH₃ | H |
| 1390 | X | Cl | (cyclohexyl) | —NH— | H | C₂H₅ | H |
| 1391 | X | Cl | (cyclohexyl) | —NHCH₂CH₂— | H | H | COCH₃ |
| 1392 | X | Cl | (cyclohexyl) | —NHCH₂CH₂— | H | H | COCH₂Cl |
| 1393 | X | Cl | (cyclohexyl) | —NHCH₂CH₂— | H | H | COC₄H₉ |
| 1394 | X | Cl | (cyclohexyl) | —NHCH₂CH₂— | H | CH₃ | COCH₃ |
| 1395 | X | Cl | (cyclohexyl) | —NHCH₂CH₂— | H | C₂H₅ | COCH₃ |
| 1396 | X | Cl | (cyclohexyl) | —NHCH₂CH₂— | H | H | H |
| 1397 | X | Cl | (cyclohexyl) | —NHCH₂CH₂— | H | CH₃ | H |
| 1398 | X | Cl | (cyclohexyl) | —NHCH₂CH₂— | H | C₂H₅ | H |
| 1399 | X | Cl | (cyclohexyl) | —N(piperazine)N— | * | H | COCH₃ |
| 1400 | X | Cl | (cyclohexyl) | —N(piperazine)N— | H | H | COCH₂Cl |
| 1401 | X | Cl | (cyclohexyl) | —N(piperazine)N— | H | H | COC₄H₉ |
| 1402 | X | Cl | (cyclohexyl) | —N(piperazine)N— | H | CH₃ | COCH₃ |
| 1403 | X | Cl | (cyclohexyl) | —N(piperazine)N— | H | C₂H₅ | COCH₃ |
| 1404 | X | Cl | (cyclohexyl) | —N(piperazine)N— | * | H | H |
| 1405 | X | Cl | (cyclohexyl) | —N(piperazine)N— | H | CH₃ | H |

| | | | | | | |
|---|---|---|---|---|---|---|
| 1406 | X Cl | cyclohexyl | -N(piperazine)N- | H | C₂H₅ | H |
| 1407 | X Cl | -CH₂-cyclohexyl | -NH- | H | H | COCH₃ |
| 1408 | X Cl | -CH₂-cyclohexyl | -NH- | H | H | COCH₂Cl |
| 1409 | X Cl | -CH₂-cyclohexyl | -NH- | H | H | COC₄H₉ |
| 1410 | X Cl | -CH₂-cyclohexyl | -NH- | H | CH₃ | COCH₃ |
| 1411 | X Cl | -CH₂-cyclohexyl | -NH- | H | C₂H₅ | COCH₃ |
| 1412 | X Cl | -CH₂-cyclohexyl | -NH- | H | H | H |
| 1413 | X Cl | -CH₂-cyclohexyl | -NH- | H | CH₃ | H |
| 1414 | X Cl | -CH₂-cyclohexyl | -NH- | H | C₂H₅ | H |
| 1415 | X Cl | -CH₂-cyclohexyl | -NHCH₂CH₂- | H | H | COCH₃ |
| 1416 | X Cl | -CH₂-cyclohexyl | -NHCH₂CH₂- | H | H | COCH₂Cl |
| 1417 | X Cl | -CH₂-cyclohexyl | -NHCH₂CH₂- | H | H | COC₄H₉ |
| 1418 | X Cl | -CH₂-cyclohexyl | -NHCH₂CH₂- | H | CH₃ | COCH₃ |
| 1419 | X Cl | -CH₂-cyclohexyl | -NHCH₂CH₂- | H | C₂H₅ | COCH₃ |
| 1420 | X Cl | -CH₂-cyclohexyl | -NHCH₂CH₂- | H | H | H |
| 1421 | X Cl | -CH₂-cyclohexyl | -NHCH₂CH₂- | H | CH₃ | H |
| 1422 | X Cl | -CH₂-cyclohexyl | -NHCH₂CH₂- | H | C₂H₅ | H |
| 1423 | X Cl | -CH₂-cyclohexyl | -N(piperazine)N- | * | H | COCH₃ |

| No. | X | R | Ring | R' | R'' | R''' |
|---|---|---|---|---|---|---|
| 1424 | X | Cl | —CH₂—(cyclohexyl) | —N◯N— (piperazine) | H | H | COCH₂Cl |
| 1425 | X | Cl | —CH₂—(cyclohexyl) | —N◯N— | H | H | COC₄H₉ |
| 1426 | X | Cl | —CH₂—(cyclohexyl) | —N◯N— | H | CH₃ | COCH₃ |
| 1427 | X | Cl | —CH₂—(cyclohexyl) | —N◯N— | H | C₂H₅ | COCH₃ |
| 1428 | X | Cl | —CH₂—(cyclohexyl) | —N◯N— | • H | H | |
| 1429 | X | Cl | —CH₂—(cyclohexyl) | —N◯N— | H | CH₃ | H |
| 1430 | X | Cl | —CH₂—(cyclohexyl) | —N◯N— | H | C₂H₅ | H |
| 1431 | X | Cl | —CH₂CH₂—(cyclohexyl) | —NH— | H | H | COCH₃ |
| 1432 | X | Cl | —CH₂CH₂—(cyclohexyl) | —NH— | H | H | COCH₂Cl |
| 1433 | X | Cl | —CH₂CH₂—(cyclohexyl) | —NH— | H | H | COC₄H₉ |
| 1434 | X | Cl | —CH₂CH₂—(cyclohexyl) | —NH— | H | CH₃ | COCH₃ |
| 1435 | X | Cl | —CH₂CH₂—(cyclohexyl) | —NH— | H | C₂H₅ | COCH₃ |
| 1436 | X | Cl | —CH₂CH₂—(cyclohexyl) | —NH— | H | H | H |
| 1437 | X | Cl | —CH₂CH₂—(cyclohexyl) | —NH— | H | CH₃ | H |
| 1438 | X | Cl | —CH₂CH₂—(cyclohexyl) | —NH— | H | C₂H₅ | H |
| 1439 | X | Cl | —CH₂CH₂—(cyclohexyl) | —NHCH₂CH₂— | H | H | COCH₃ |

| | | | | | | | |
|---|---|---|---|---|---|---|---|
| 1440 | X | Cl | -CH₂CH₂-[cyclohexyl] | -NHCH₂CH₂- | H | H | COCH₂Cl |
| 1441 | X | Cl | -CH₂CH₂-[cyclohexyl] | -NHCH₂CH₂- | H | H | COC₄H₉ |
| 1442 | X | Cl | -CH₂CH₂-[cyclohexyl] | -NHCH₂CH₂- | H | CH₃ | COCH₃ |
| 1443 | X | Cl | -CH₂CH₂-[cyclohexyl] | -NHCH₂CH₂- | H | C₂H₅ | COCH₃ |
| 1444 | X | Cl | -CH₂CH₂-[cyclohexyl] | -NHCH₂CH₂- | H | H | H |
| 1445 | X | Cl | -CH₂CH₂-[cyclohexyl] | -NHCH₂CH₂- | H | CH₃ | H |
| 1446 | X | Cl | -CH₂CH₂-[cyclohexyl] | -NHCH₂CH₂- | H | C₂H₅ | H |
| 1447 | X | Cl | -CH₂CH₂-[cyclohexyl] | -N(piperazine)N- | * | H | COCH₃ |
| 1448 | X | Cl | -CH₂CH₂-[cyclohexyl] | -N(piperazine)N- | H | H | COCH₂Cl |
| 1449 | X | Cl | -CH₂CH₂-[cyclohexyl] | -N(piperazine)N- | H | H | COC₄H₉ |
| 1450 | X | Cl | -CH₂CH₂-[cyclohexyl] | -N(piperazine)N- | H | CH₃ | COCH₃ |
| 1451 | X | Cl | -CH₂CH₂-[cyclohexyl] | -N(piperazine)N- | H | C₂H₅ | COCH₃ |
| 1452 | X | Cl | -CH₂CH₂-[cyclohexyl] | -N(piperazine)N- | * | H | H |
| 1453 | X | Cl | -CH₂CH₂-[cyclohexyl] | -N(piperazine)N- | H | CH₃ | H |
| 1454 | X | Cl | -CH₂CH₂-[cyclohexyl] | -N(piperazine)N- | H | C₂H₅ | H |
| 1455 | X | Cl | [cyclohexyl]-CH₂- | -NH- | H | H | COCH₃ |

| | | | | | | |
|---|---|---|---|---|---|---|
| 1456 | X Cl | cyclohexyl-CH₂— | —NH— | H | H | COCH₂Cl |
| 1457 | X Cl | cyclohexyl-CH₂— | —NH— | H | H | COC₄H₉ |
| 1458 | X Cl | cyclohexyl-CH₂— | —NH— | H | CH₃ | COCH₃ |
| 1459 | X Cl | cyclohexyl-CH₂— | —NH— | H | C₂H₅ | COCH₃ |
| 1460 | X Cl | cyclohexyl-CH₂— | —NH— | H | H | H |
| 1461 | X Cl | cyclohexyl-CH₂— | —NH— | H | CH₃ | H |
| 1462 | X Cl | cyclohexyl-CH₂— | —NH— | H | C₂H₅ | H |
| 1463 | X Cl | cyclohexyl-CH₂— | —NHCH₂CH₂— | H | H | COCH₃ |
| 1464 | X Cl | cyclohexyl-CH₂— | —NH— | H | H | COCH₂Cl |
| 1465 | X Cl | cyclohexyl-CH₂— | —NH— | H | H | COC₄H₉ |
| 1466 | X Cl | cyclohexyl-CH₂— | —NH— | H | CH₃ | COCH₃ |
| 1467 | X Cl | cyclohexyl-CH₂— | —NH— | H | C₂H₅ | COCH₃ |
| 1468 | X Cl | cyclohexyl-CH₂— | —NHCH₂CH₂— | H | H | H |
| 1469 | X Cl | cyclohexyl-CH₂— | —NHCH₂CH₂— | H | CH₃ | H |
| 1470 | X Cl | cyclohexyl-CH₂— | —NHCH₂CH₂— | H | C₂H₅ | H |
| 1471 | X Cl | cyclohexyl-CH₂— | piperazine | * | H | COCH₃ |
| 1472 | X Cl | cyclohexyl-CH₂— | piperazine | H | H | COCH₂Cl |
| 1473 | X Cl | cyclohexyl-CH₂— | piperazine | H | H | COC₄H₉ |

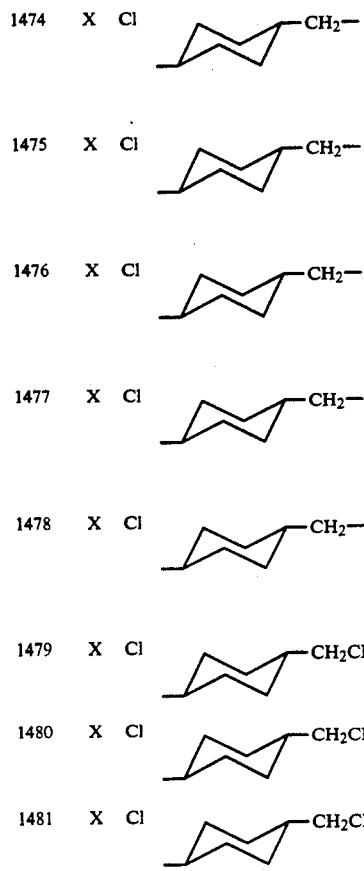
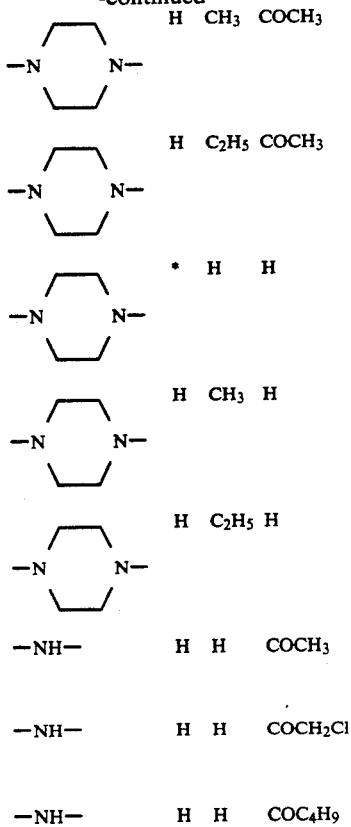

| | | | | | | |
|---|---|---|---|---|---|---|
| 1474 | X | Cl | (cyclohexyl)-CH₂- | piperazine | H | CH₃ COCH₃ |
| 1475 | X | Cl | (cyclohexyl)-CH₂- | piperazine | H | C₂H₅ COCH₃ |
| 1476 | X | Cl | (cyclohexyl)-CH₂- | piperazine | * | H   H |
| 1477 | X | Cl | (cyclohexyl)-CH₂- | piperazine | H | CH₃ H |
| 1478 | X | Cl | (cyclohexyl)-CH₂- | piperazine | H | C₂H₅ H |
| 1479 | X | Cl | (cyclohexyl)-CH₂CH₂- | —NH— | H | H COCH₃ |
| 1480 | X | Cl | (cyclohexyl)-CH₂CH₂- | —NH— | H | H COCH₂Cl |
| 1481 | X | Cl | (cyclohexyl)-CH₂CH₂- | —NH— | H | H COC₄H₉ |

BIOLOGICAL EVALUATION

Compounds of Examples 1-80 are suitable angiotensin II antagonists for use as the first component of conjugates of the invention. The AII receptor binding activity of many of the Example #1-#80 compounds, for example, is described in EP #253,310 published Jan. 20, 1988. The compound of Example #5 was further evaluated in three biological assays (Assays "A", "B" and "C") for AII antagonist and blood pressure lowering properties. In two other assays, blood-pressure lowering effects of the conjugate of Example #81 were evaluated (Assays "D" and "E").

Assay A: Angiotensin II Binding Activity

Compound of Example #5 was tested for ability to bind to the smooth muscle angiotensin II receptor using a rat uterine membrane preparation. Angiotensin II (AII) was purchased from Peninsula Labs. 125I-angiotensin II (specific activity of 2200 Ci/mmol) was purchased from Du Pont-New England Nuclear. Other chemicals were obtained from Sigma Chemical Co. This assay was carried out according to the method of Douglas et al [Endocrinology, 106, 120-124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM MgCl₂, 2 mM EDTA, 0.5% bovine serum albumin, 50 mM Tris-HCl, pH 7.5 and $^{125}$I-AII (approximately 10⁵ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC₅₀) of the tested AII antagonist which gives 50% displacement of the total specifically bound $^{125}$I-AII from the high affinity AII receptor. Binding data were analyzed by a nonlinear least-squares curve fitting program. Results are reported in Table VIII.

Assay B: In Vitro Vascular Smooth Muscle-Response for AII

Compound of Example #5 was tested for AII antagonist activity in rabbit aortic rings. Male New Zealand white rabbits (2-2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (nM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one gram of passive tension was placed on the rings. Angiotensin II concentration-response curves were then recorded ($3 \times 10^{-10}$ to $1 \times 10^{-5}$M). Each concentration of AII was allowed to elicit its maximal contraction, and then AII was washed out repeatedly for 30 minutes before rechallenging with a higher concentration of AII. Aorta rings were exposed to the test antagonist at $10^{-5}$M for 5 minutes before challenging with AII. Adjacent segments of the same aorta ring were used for all concentration-response curves in the presence or absence of the test antagonist. The effectiveness of the test compound was expressed in terms of pA$_2$ values and were calculated according to H. O. Schild [*Br. J. Pharmacol. Chemother.*, 189–206 (1947)]. The pA$_2$ value is the concentration of the test antagonist compound which increases the EC$_{50}$ value for AII by a factor of two. The test compound was evaluated in aorta rings from three rabbits. Results are reported in Table VIII.

TABLE VIII

In Vitro Angiotensin II
Activity of Compounds of Formula I

| Test Compound | [1]Assay A IC$_{50}$ (nM) | [2]Assay B PA$_2$ |
|---|---|---|
| Ex. #5 | 216 ± 45 | 7.13 ± 0.16 |

[1]Assay A: In Vitro angiotensin II Binding Activity
[2]Assay B: Vascular Smooth Muscle Response

Assay C: In Vivo Intraduodenal and Intravenous Pressor Assay Response for AII Antagonists The in vivo AII receptor antagonist activity of Example #5 compound was examined in ganglion-blocked male Sprague-Dawley rats (Harlan Sprague-Dawley, Inc.), weighing 300–400 g, anesthetized with 100 mg/kg i.p. Inactin. Catheters (PE-50) were implanted in a femoral artery and vein to measure mean arterial pressure and to administer compounds, respectively. A tracheal catheter maintained airway patency. For intravenous experiments, autonomic neurotransmission was blocked by treatment with mecamylamine (3 mg/kg i.v.) and atropine (400 μg/kg i.v.). AII (30 ng/kg i.v., 20–25 μl volume) was administered four times at 10 minute intervals to establish a reproducible control pressor response. Example #5 compound was then administered at 1, 3 and 10 mg/kg in separate groups of rats as an intravenous bolus (0.2 ml volume) before rechallenging with AII (30 ng/kg, 20–25 μl volume) for the following 2 hours. For intraduodenal experiments, rats were anesthetized as above, but ganglion blockade was not performed. AII was administered at 100 ng/kg i.v. (20–25 μl volume), and was administered at 10, 30 and 100 mg/kg in separate groups of rats as an intraduodenal bolus (0.2 ml volume). Angiotensin II injections were then given 5, 10, 20, 30, 45, 60, 75, 90, and 120 minutes after administration of the test compound and response of arterial pressure was monitored. The response to AII was calculated as percent of the control response and then the percent inhibition was calculated as 100 minus the percent control response. Duration of action of a test compound was defined as the time from peak percent inhibition to 50% of peak. The test compound was tested in two rats and the values for the two rats were averaged. Results are reported in Tables IX and X as percent of the control of AII pressor response, where "control" is defined as AII pressor response before the AII antagonist test compound is administered.

TABLE IX

In Vivo Intravenous Angiotensin II
Activity of Example #5 Compound
(% Control of AII Pressor Response)

| Dose (mg/kg) | Time (min) | | | | | | | | | |
|---|---|---|---|---|---|---|---|---|---|---|
| | 1 | 5 | 10 | 20 | 30 | 40 | 50 | 60 | 75 | 90 | 120 |
| 1 | 80 | 85 | 92 | 90 | 88 | 86 | 86 | 89 | 93 | 95 | 100 |
| n = 4 | ±3 | ±4 | ±4 | ±6 | ±5 | ±5 | ±6 | ±5 | ±3 | ±5 | ±0 |
| 3 | 39 | 55 | 63 | 68 | 74 | 75 | 75 | 81 | 88 | 92 | 98 |
| n = 4 | ±5 | ±7 | ±8 | ±6 | ±7 | ±5 | ±3 | ±7 | ±7 | ±5 | ±1 |
| 10 | 4 | 16 | 23 | 31 | 40 | 47 | 51 | 60 | 71 | 80 | 96 |
| n = 6 | ±2 | ±2 | ±2 | ±2 | ±3 | ±4 | ±4 | ±6 | ±7 | ±8 | ±6 |

TABLE X

In Vivo Intraduodenal Angiotensin II Activity
of Example #5 Compound
(% Control of AII Pressor Response)

| Dose (mg/kg) | Time (min) | | | | | | | | |
|---|---|---|---|---|---|---|---|---|
| | 1 | 5 | 10 | 20 | 30 | 40 | 50 | 60 | 75 |
| 10 | 100 | 94 | 99 | 85 | 91 | 91 | 95 | 93 | 95 |
| n = 3 | ±0 | ±4 | ±1 | ±11 | +9 | ±9 | ±5 | ±7 | ±5 |
| 30 | 48 | 48 | 44 | 28 | 34 | 42 | 41 | 53 | 74 |
| n = 4 | ±4 | ±7 | ±11 | ±5 | ±4 | ±6 | ±0 | ±2 | ±7 |
| 100 | 28 | 19 | 15 | 14 | 9 | 5 | 13 | 10 | 13 |
| n = 4 | ±3 | ±4 | ±3 | ±8 | ±5 | ±2 | ±6 | ±4 | ±5 |

Assay D: In Vivo Effects of Chronic Infusion of Conjugate of the Invention

Figure 2:
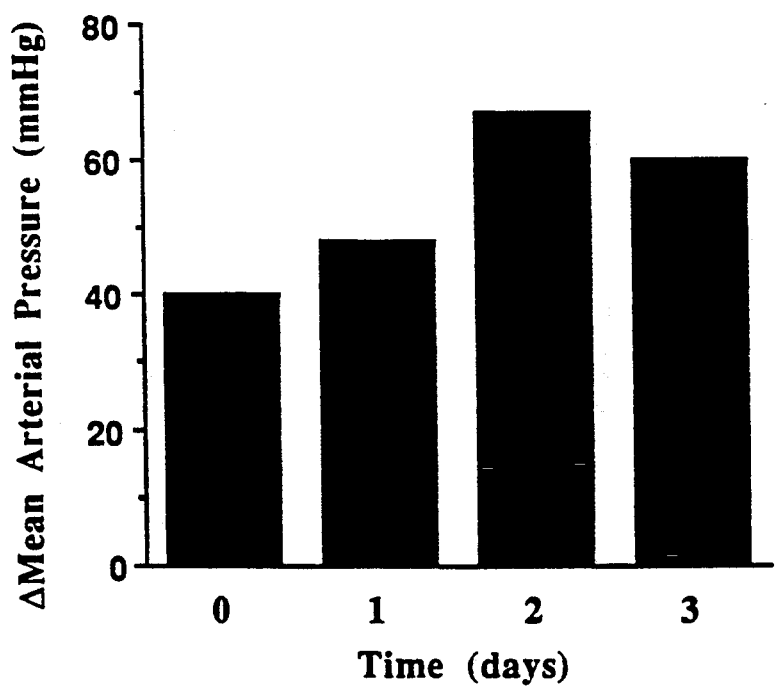
FIG. 2 is a graph showing angiotensin II pressor response in a spontaneously hypertensive rat infused by intravenous administration with a conjugate of the invention over a period of three days.

A conjugate of the invention as synthesized in Example 81 was evaluated biologically by an in vivo assay to determine the ability of the conjugate to selectively inhibit renal action and thereby control blood pressure. This in vivo experiment was conducted to characterize the effects of the Example 81 conjugate on spontaneously hypertensive rats (SHR) by acute administration i.v. and by chronic administration i.v. The Example 81 compound or saline vehicle was infused continuously for four days in SHR. Mean arterial pressure was measured (Gould Chart Recorder, model 3800; Statham P23Db pressure transducer) via an indwelling femoral artery catheter between 10:00 A. M. and 2:00 P. M. each day. The Example 81 conjugate (10 mg/hr) or saline was infused via a jugular vein catheter with a Harvard infusion pump. After administration of the Example 81 conjugate, there was observed a lowered mean arterial pressure as compared to the saline vehicle control as reported in Table XI and also in FIG. 1. A test was conducted to determine whether the Example 81 conjugate would antagonize non-renal, vascular angiotensin II receptors. In this test AII was administered by bolus injection (100 ng/kg) to the SHR rats (described above) on the control day and on days 1, 2 and 3 during conjugate infusion. No evidence for systemic angiotensin II receptor antagonism was observed, given the similar pressor responses to injections of angiotensin II on the control day and days 1, 2 and 3 of infusion of the Example 81 conjugate as shown in Table XII and also in FIG. 2.

TABLE XI

Effect of Ex. #81 Conjugate on Mean Arterial Pressure: Chronic Administration

| Time (days): | Control | 1 | 2 | 3 |
|---|---|---|---|---|
| MAP (mm Hg) | 163 | 148 | 135 | 140 |

TABLE XII

Effect of Ex. #81 Conjugate on AII Pressor Response

| Time (days): | Control | 1 | 2 | 3 |
|---|---|---|---|---|
| MAP (mm Hg) | 44 | 45 | 65 | 60 |

Assay "E": In Vivo Effects of Acute Infusion of Conjugate of the Invention

Figure 3:
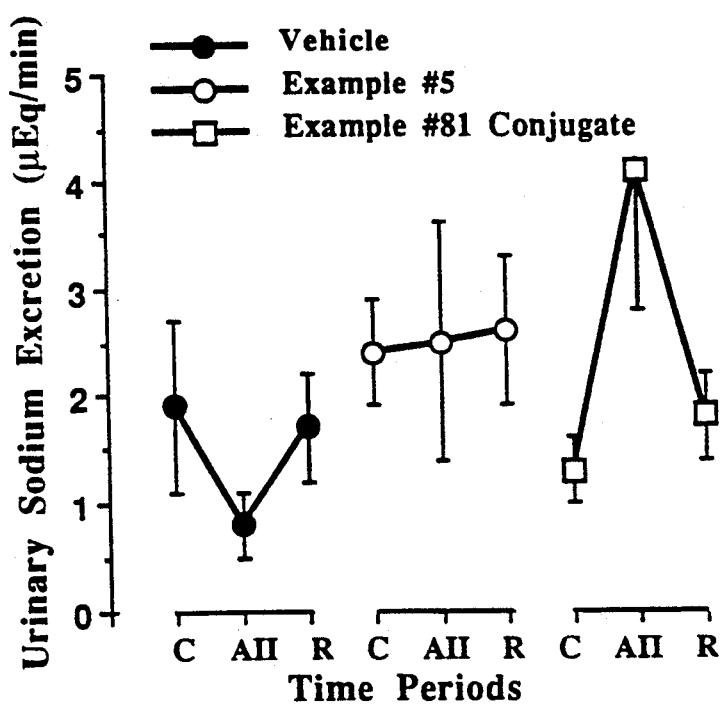
FIG. 3 is a graph showing urinary sodium excretion response to angiotensin II infusion in concious normotensive rats followed by administration of a saline vehicle, an angiotensin II antagonist, or a renal-selective conjugate of the invention.
Figure 4:
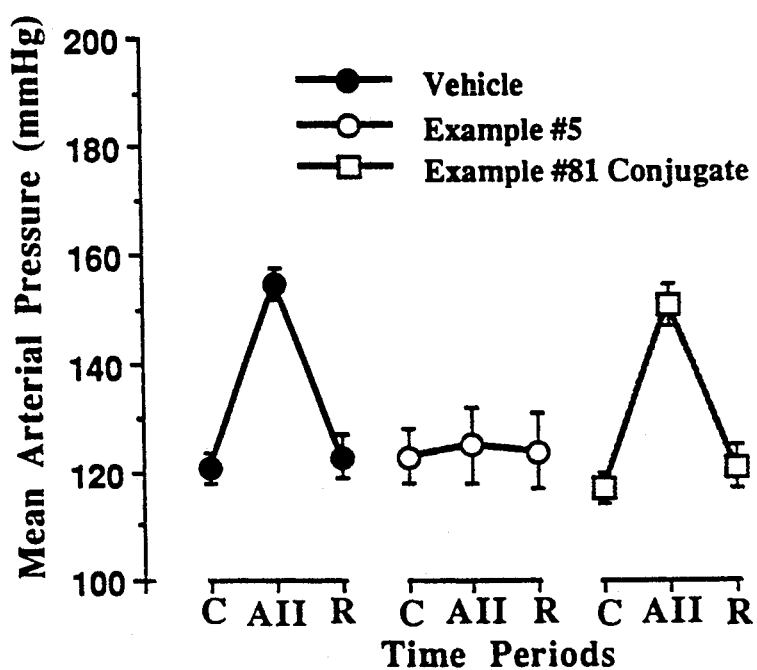
FIG. 4 is a graph showing mean arterial pressure response to angiotensin II infusion in conscious normotensive rats followed by administration of a saline vehicle, an angiotensin II antagonist, or a renal-selective conjugate of the invention.

In this assay, a comparison was made between an antagonist compound (Ex. #5) and a glutamyl conjugate (Ex. #81) of the Ex. #5 AII antagonist compound to determine the renal selectivity of the conjugate. Male Sprague-Dawley rats (300–350 g body weight) had catheters implanted into the femoral artery and vein under chloral hydrate anesthesia (400 mg/kg, i.p.). After 2 to 4 days of recovery, on the experimental day, a urinary bladder catheter was implanted under methohexital anesthesia (50 mg/kg, i.p.). Rats were placed in a restraint device to allow for urine collection and mean arterial pressure measurements. After 1–2 hours of recovery, in conscious rats, an isotonic saline infusion (50 μl/min) was started and continued for the duration of the experiment. After one hour equilibration to the saline infusion, a 20 minute control urine and mean arterial pressure collection were obtained. Then angiotensin II was infused at 20 ng/min for 25 minutes. After 5 minutes of angiotensin II infusion, a 20 minute experimental collection was made. Finally, 5 minutes after the end of angiotensin II infusion, a 20 minute recovery collection was obtained. In separate groups of rats, vehicle (0.3 ml isotonic saline, i.v. bolus), Example #5 angiotensin II antagonist compound (100 mg/kg, i.v. bolus), or Example #81 conjugate (100 mg/kg, i.v. bolus) was administered 1-2 minutes prior to onset of angiotensin II infusion. Infusion of angiotensin II increased mean arterial pressure and decreased urinary sodium excretion. The Example #5 AII antagonist compound prevented both responses to angiotensin II. The Example #81 conjugate had no effect on the mean arterial pressure response but prevented the antinatriuretic response to angiotensin II. Angiotensin II infusion following administration of Example #81 conjugate actually increased urinary sodium excretion, probably due to a pressure natriuresis. Results are shown in Tables XIII and XIV and also in FIGS. 3 and 4. Data are presented as means±SE. Repeated measures analysis of variance was used for main effects and interactions and Tukey's HSD test was used for pairwise comparisons among means. Statistical significance was defined as $p<0.05$.

TABLE XIII

Effect of Ex. #81 Conjugate on Urinary Sodium Excretion (μEq/min/100 g BW)

| | Control | AII | Recovery |
|---|---|---|---|
| Vehicle | 1.9 ± 0.8 | 0.8 ± 0.3* | 1.7 ± 0.5 |
| Ex. #5 | 2.4 ± 0.5 | 2.5 ± 1.1 | 2.6 ± 0.7 |
| Ex. #81 | 1.3 ± 0.3 | 4.1 ± 1.3* | 1.8 ± 0.4 |

TABLE XIV

Effect of Ex. #81 Conjugate on Mean Arterial Pressure (mm Hg): Acute Administration

| | Control | AII | Recovery |
|---|---|---|---|
| Vehicle (n = 6) | 121 ± 3 | 155 ± 3* | 123 ± 4 |
| Ex. #5 (n = 6) | 123 ± 5 | 125 ± 7 | 124 ± 7 |
| Ex. #81 (n = 6) | 117 ± 3 | 151 ± 4* | 121 ± 4 |

Also embraced within this invention is a class of pharmaceutical compositions comprising one or more conjugates which comprises a first component selected from angiotensin II antagonist compounds of Formula I linked to a second component provided by an enzyme-cleavable moiety. Such pharmaceutical compositions further comprise one or more non-toxic, pharmaceutically acceptable carriers and/or diluents and/or adjuvants (collectively referred to herein as "carrier" materials) and, if desired, other active ingredients. The conjugates of the present invention may be administered by any suitable route, preferably in the form of a pharmaceutical composition adapted to such a route, and in a dose effective for the treatment intended. Therapeutically effective doses of a conjugate of the present invention required to prevent or arrest the progress of the medical condition are readily ascertained by one of ordinary skill in the art. The conjugates and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the conjugate. Examples of such dosage units are tablets or capsules. These may with advantage contain an amount of conjugate from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The conjugate may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Conjugates indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the conjugates and/or compositions of this invention is selected in accordance with a variety of factors, including the type, age, weight, sex and medical condition of the patient, the severity of the disease, the route of administration, and the particular conjugate employed, and thus may vary widely.

For therapeutic purposes, the conjugates of this invention are ordinarily combined with one or more adjuvants appropriate to the indicated route of administration. If administered per os, the conjugate may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of conjugate in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The conjugates may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A renal selective conjugate consisting of a first radical and a second radical, said first and second radicals connected together by a kidney-enzyme-cleavable bond, wherein said first radical is provided by a biphenylalkyl 1H-substituted-1,3-imidazole angiotensin II antagonist compound of Formula I:

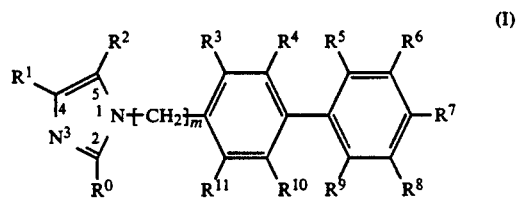

wherein m is one; wherein $R^0$ is selected from $C_4H_9(n)$, $CH_3CH_2CH=CH$, $C_3H_7(N)$, $SC_3H_7$,

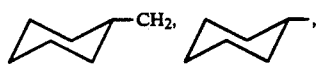

$C_2H_5$, $C_5H_{11}(n)$, $C_6H_{13}(n)$, $SC_4H_9$,

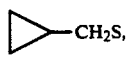

$CH_3CH=CH$ and $CH_3CH_2CH_2CH=CH-$; wherein $R^1$ is selected from amino, aminomethyl, aminoethyl, aminopropyl, $CH_2OH$, $CH_2OCOCH_3$, $CH_2Cl$, F, Cl, Br, I, $CH_2OCH_3$, $CH_2OCH(CH_3)_2$, CHO, $CH_2CO_2H$, $CH(CH_3)CO_2H$, $-CO_2CH_3$, $-CONH_2$, $-CONHCH_3$, $CON(CH_3)_2$, $-CH_2-NHCO_2C_2H_5$,

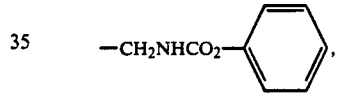

$-CH_2NHCO_2CH_3$, $-CH_2NHCO_2C_3H_7$, $-CH_2NHCO_2CH(CH_3)_2$, $-CH_2NHCO_2C_4H_9$, $CH_2NHCO_2$-adamantyl, $-CH_2NHCO_2$-(1-naphthyl), $-CH_2NHCONHCH_3$, $-CH_2NHCONHC_2H_5$, $-CH_2NHCONHC_3H_7$, $-CH_2NHCONHC_4H_9$, $-CH_2NHCONHCH(CH_3)_2$, $-CH_2NHCONH(1-naphthyl)$, $-CH_2NHCONH(1-adamantyl)$, $-CH_2CH_2CH_2CO_2H$, $-CH_2CH_2F$, $-CH_2OCONHCH_3$, $-CH_2CH_2CH_2F$, $-CH_2SH$ and

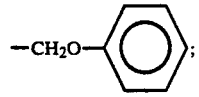

wherein $R^2$ is selected from H, F, Cl, Br, I, $NO_2$, $CF_3$, $CH_2OH$, methyl, ethyl, n-propyl, isoroyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, difluoromethyl, 1,1-difluoroethyl, 1,1-difluoropropyl, 1,1-difluorobutyl and 1,1-difluoropentyl; with the proviso that at least one of $R^5$, $R^6$, $R^8$ and $R^9$ is an acidic group selected from $CO_2H$, SH, $SO_3H$ and

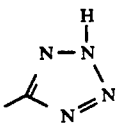

and wherein each of the remainder of $R^3$ through $R^{11}$ is hydrido, with the further proviso that at least one of said $R^1$ through $R^{11}$ is a substituent selected from COOH and moieties containing a terminal primary or secondary amino group; or a tautomer thereof or a pharmaceutically-acceptable salt thereof;

wherein said second radical is provided by a compound selected from a class of compounds of Formula II:

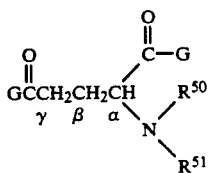

wherein each of $R^{50}$ and $R^{51}$ may be independently selected from hydrido, alkylcarbonyl, alkoxycarbonyl, alkoxyalkyl, hydroxyalkyl and haloalkyl; and wherein G is selected from hydrido, hydroxyl, halo, mercapto, $-OR^{52}$, $-SR^{53}$ and

with each of $R^{52}$, $R^{53}$ and $R^{54}$ independently selected from alkyl, and wherein each of $R^{53}$ and $R^{54}$ may be further independently selected from hydrido;

with the proviso that said kidney-enzyme-cleavable bond is within an amide group formed between said first and second radicals, wherein said first radical has a terminal primary or secondary amino moiety, wherein said first-radical amino moiety is provided by one of said $R^1$ through $R^{11}$ substituents of said Formula I compound or is provided by a linking moiety attached to a carbonyl group attached at one of said $R^1$ through $R^{11}$ substituents of said Formula I, and wherein said second radical has a carbonyl moiety attached at the gamma-position carbon of said Formula II compound, whereby said amide bond is formed from said first-radical amino moiety and said second radical carbonyl moiety; and wherein said linking moiety is a divalent radical of Formula III:

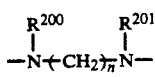 (III)

wherein each of $R^{200}$ and $R^{201}$ may be independently selected from hydrido, alkyl, cycloaklyl, cycloalkylalkyl, alkoxyalkyl, hydroxyalkyl and haloalkyl; and wherein n is a number selected from zero through six, inclusive;

or a pharmaceutically-acceptable salt of said renal-selective conjugate.

2. Conjugate of claim 1 wherein m is one; wherein $R^0$ is selected from $C_4H_9(n)$, $CH_3CH_2CH=CH$, $C_3H_7(N)$, $SC_3H_7$,

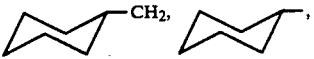

$C_2H_5$, $C_5H_{11}(n)$, $C_6H_{13}(n)$, $SC_4H_9$,

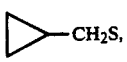

$CH_3CH=CH$ and $CH_3CH_2CH_2CH=CH-$; wherein $R^1$ is selected from H, $NO_2$, $CF_3$, $CH_2OH$, F, Cl, Br, I, methyl, ethyl, n-propyl isoproyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, difluoromethyl, 1,1-difluoroethyl, 1,1-difluoropropyl, 1,1-difluorobutyl and 1,1-difluoropentyl; wherein $R^2$ is selected from amino, aminomethyl, aminoethyl, aminopropyl, $CH_2OH$, $CH_2OCOCH_3$, $CH_2Cl$, $CH_2OCH_3$, $CH_2OCH(CH_3)_2$, F, Cl, Br, I, CHO, $CH_2CO_2H$, $CH(CH_3)CO_2H$, $-CO_2CH_3$, $-CONH_2$, $-CONHCH_3$, $CON(CH_3)_2$, $-CH_2NHCO_2C_2H_5$,

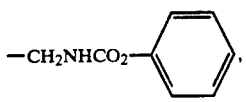

$-CH_2NHCO_2CH_3$, $-CH_2NHCO_2C_3H_7$, $-CH_2NHCO_2CH(CH_3)_2$, $-CH_2NHCO_2C_4H_9$, $CH_2NHCO_2$-adamantyl, $-CH_2NHCO_2$-(1-naphthyl), $-CH_2NHCONHCH_3$, $-CH_2NHCONHC_2H_5$, $-CH_2NHCONHC_3H_7$, $-CH_2NHCONHC_4H_9$, $-CH_2NHCONHCH(CH_3)_2$, $-CH_2NHCONH(1$-naphthyl$)$, $-CH_2NHCONH(1$-adamantyl$)$, $CO_2H$, $-CH_2CH_2CH_2CO_2H$, $-CH_2CH_2F$, $CH_2OCONHCH_3$, $-CH_2CH_2CH_2F$, $-CH_2SH$ and

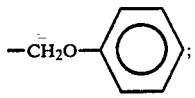

with the proviso that at least one of $R^5$, $R^6$, $R^8$ and $R^9$ is an acidic group selected from COOH and

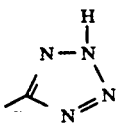

and wherein each of the remainder of $R^3$ through $R^{11}$ is hydrido, with the further proviso that at least one of said $R^1$ through $R^{11}$ is a substituent selected from COOH and moieties containing a terminal primary or secondary amino group; or a tautomer thereof or a pharmaceutically-acceptable salt thereof.

3. Conjugate of claim 1 wherein each G substituent is hydroxy.

4. Conjugate of claim 1 wherein each G substituent is hydroxy; wherein $R^{50}$ is hydrido; and wherein $R^{51}$ is selected from

wherein $R^{55}$ is selected from methyl, ethyl, n-propyl, isopropyl, n-butyl, sec-butyl, iso-butyl, tert-butyl, n-pentyl, neopentyl, n-hexyl and chloromethyl.

5. Conjugate of claim 1 wherein said second radical is

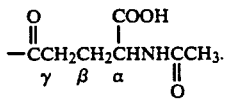

6. Conjugate of claim 1 wherein said first radical is a biphenylalkyl 1H-substituted-1,3-imidazole angiotensin II antagonist compound containing a terminal primary or secondary amino moiety attached at one of said $R^1$ through $R^{11}$ positions of Formula I, said amino moiety selected from amino and linear or branched aminoalkyl moieties containing linear or branched alkyl groups selected from aminomethyl, aminoethyl, aminopropyl, aminoisopropyl, aminobutyl, aminosecbutyl, aminoisobutyl, aminotertbutyl, aminopentyl, aminoisopentyl and aminoneopentyl.

7. Conjugate of claim 1 wherein each of $R^{200}$ and $R^{201}$ is hydrido.

8. Conjugate of claim 1 wherein said angiotensin II antagonist compound is 4'-[2-butyl-5-chloro-4-(hydroxymethyl)-1H-imidazol-1-ylmethyl][1,1'-biphenyl]-2-carboxylic acid or a pharmaceutically-acceptable salt thereof.

9. Conjugate of claim 8 which is N-acetyl-L-glutamic acid, 5-[[4'-[2-butyl-5-chloro-4-(hydroxymethyl)-1H-imidazol-1-ylmethyl][1,1' -biphenyl]-2-yl]carbonyl]hydrazide or a pharmaceutically-acceptable salt thereof.

10. Conjugate of claim 8 which is $N^2$-acetyl-N-[[2-butyl-5-chloro-1-[[2'-(1H-tetrazol-5-yl)[1,1'-biphenyl]-4-yl]methyl]-1H-imidazol-4-yl]methyl]-L-glutamine or a pharmaceutically-acceptable salt thereof.

11. Conjugate of claim 8 which is N-acetyl-N-L-glutamic acid, 5-[2-butyl-5-chloro-1-[[2'-(1H-tetrazol-5-yl)[1,1-biphenyl]-4-yl]methyl]-1H-imidazol-4-yl]acetyl-hydrazide or a pharmaceutically-acceptable salt thereof.

12. Conjugate of claim 1 wherein said angiotensin II antagonist compound is 4'-[2-butyl-4-chloro-5-(hydroxymethyl)-1H-imidazol-1-ylmethyl][1,1'-biphenyl]-2-carboxylic acid or a pharmaceutically-acceptable salt thereof.

13. Conjugate of claim 12 which is N-acetyl-L-glutamic acid, 5-[[4'-[2-butyl-4-chloro-5-(hydroxymethyl)-1H-imidazol-1-ylmethyl][1,1'-biphenyl]-2-yl]carbonyl]hydrazide or a pharmaceutically-acceptable salt thereof.

14. Conjugate of claim 12 which is $N^2$-acetyl-N-[[2-butyl-4-chloro-1-[[2'-(1H-biphenyl-4-yl)methyl]-1H-imidazol-5-yl]methyl]-L-glutamine or a pharmaceutically-acceptable salt thereof.

15. Conjugate of claim 12 which is N-acetyl-L-glutamic acid, 5-[2-butyl-4-chloro-1-[[2'-(1H-tetrazol-5-yl)[1,1'-biphenyl]-4-yl]methyl]-1H-imidazol-5-yl]acetyl-hydrazide or a pharmaceutically-acceptable salt thereof.

16. A pharmaceutical composition comprising one or more pharmaceutically-acceptable carriers or diluents and a therapeutically-effective amount of a renal-selective conjugate, said renal selective conjugate consisting of a first radical and a second radical, said first and second radicals connected together by a kidney-enzyme-cleavable bond, wherein said first radical is provided by a biphenylalkyl 1H-substituted-1,3-imidazole angiotensin II antagonist compound of Formula I:

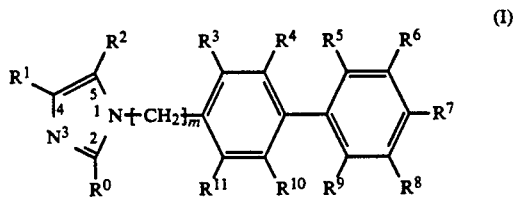

wherein m is one; wherein $R^0$ is selected from $C_4H_9(n)$, $CH_3CH_2CH=CH$, $C_3H_7(N)$, $SC_3H_7$,

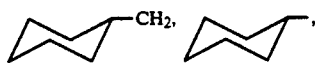

$C_2H_5$, $C_5H_{11}(n)$, $C_6H_{13}(n)$, $SC_4H_9$,

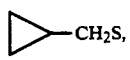

$CH_3CH=CH$ and $CH_3CH_2CH_2CH=CH$—; wherein $R^1$ is selected from amino, aminomethyl, aminoethyl, aminopropyl, $CH_2OH$, $CH_2OCOCH_3$, $CH_2Cl$, F, Cl, Br, I, $CH_2OCH_3$, $CH_2OCH(CH_3)_2$, CHO, $CH_2CO_2H$, $CH(CH_3)CO_2H$, —$CO_2CH_3$, —$CONH_2$, —$CONHCH_3$, $CON(CH_3)_2$, —$CH_2$—$NHCO_2C_2H_5$,

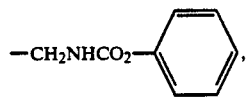

—$CH_2NHCO_2CH_3$, —$CH_2NHCO_2C_3H_7$, —$CH_2NH$-$CO_2CH_2(CH_3)$ $_2$, —$CH_2NHCO_2C_4H_9$, $CH_2NHCO_2$-adamantyl, —$CH_2NHCO_2$-(1-naphthyl), —$CH_2NH$-$CONHCH_3$, —$CH_2NHCONHC_2H_5$, —$CH_2NH$-$CONHC_3H_7$, —$CH_2NHCONHC_4H_9$, —$CH_2NH$-$CONHCH(CH_3)_2$, —$CH_2NHCONH(1$-naphthyl$)$, —$CH_2NHCONH(1$-adamantyl$)$, —$CH_2CH_2CH_2CO_2H$, —$CH_2CH_2F$, —$CH_2OCONHCH_3$, —$CH_2CH_2CH_2F$, —$CH_2SH$ and

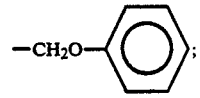

wherein $R^2$ is selected from H, F, Cl, Br, I, $NO_2$, $CF_3$, $CH_2OH$, methyl, ethyl, n-propyl, isoproyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, difluoromethyl, 1,1-difluoroethyl, 1,1-difluoropropyl, 1,1-difluorobutyl and 1,1-difluoropentyl; with the proviso that at least one of $R^5$, $R^6$, $R^8$ and $R^9$ is an acidic group selected from $CO_2H$, SH, $SO_3H$ and

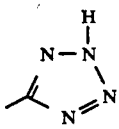

and wherein each of the remainder of $R^3$ through $R^{11}$ is hydrido, with the further proviso that at least one of said $R^1$ through $R^{11}$ is a substituent selected from COOH and moieties containing a terminal primary or secondary amino group; or a tautomer thereof or a pharmaceutically-acceptable salt thereof;

wherein said second radical is provided by a compound selected from a class of compounds of Formula II:

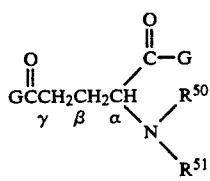
(II)

wherein each of $R^{50}$ and $R^{51}$ may be independently selected from hydrido, alkylcarbonyl, alkoxycarbonyl, alkoxyalkyl, hydroxyalkyl and haloalkyl; and wherein G is selected from hydrido, hydroxyl, halo, mercapto, $-OR^{52}$, $-SR^{53}$ and

with each of $R^{52}$, $R^{53}$ and $R^{54}$ independently selected from alkyl, and wherein each of $R^{53}$ and $R^{54}$ may be further independently selected from hydrido;

with the proviso that said kidney-enzyme-cleavable bond is within an amide group formed between said first and second radicals, wherein said first radical has a terminal primary or secondary amino moiety, wherein said first-radical amino moiety is provided by one of said $R^1$ through $R^{11}$ substituents of said Formula I compound or is provided by a linking moiety attached to a carbonyl group attached at one of said $R^1$ through $R^{11}$ substituents of said Formula I, and wherein said second radical has a carbonyl moiety attached at the gamma-position carbon of said Formula II compound, whereby said amide bond is formed from said first-radical amino moiety and said second radical carbonyl moiety; and wherein said linking moiety is a divalent radical of Formula III:

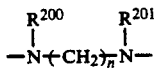
(III)

wherein each of $R^{200}$ and $R^{201}$ may be independently selected from hydrido, alkyl, cycloaklyl, cycloalkylalkyl, alkoxyalkyl, hydroxyalkyl and haloalkyl; and wherein n is a number selected from zero through six, inclusive;

or a pharmaceutically-acceptable salt of said renal-selective conjugate.

17. The composition of claim 16 wherein m is one; wherein $R^0$ is selected from $C_4H_9(n)$, $CH_3CH_2CH=CH$, $C_3H_7(N)$, $SC_3H_7$,

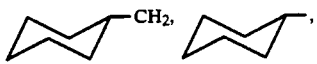

$C_2H_5$, $C_5H_{11}(n)$, $C_6H_{13}(n)$, $SC_4H_9$,

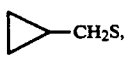

$CH_3CH=CH$ and $CH_3CH_2CH_2CH=CH-$; wherein $R^1$ is selected from H, $NO_2$, $CF_3$, $CH_2OH$, F, Cl, Br, I, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, difluoromethyl, 1,1-difluoroethyl, 1,1-difluoropropyl, 1,1-difluorobutyl and 1,1-difluoropenyl; wherein $R^2$ is selected from amino, aminomethyl, aminoethyl, aminopropyl, $CH_2OH$, $CH_2OCOCH_3$, $CH_2Cl$, $CH_2OCH_3$, $CH_2OCH(CH_3)_2$, F, Cl, Br, I, CHO, $CH_2CO_2H$ $CH(CH_3)CO_2H$, $-CO_2CH_3$, $-CONH_2$, $-CONHCH_3$, $CON(CH_3)_2$, $-CH_2NHCO_2C_2H_5$,

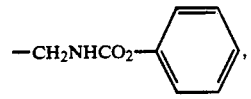

$CH_2NHCO_2CH_3$, $-CH_2NHCO_2C_3H_7$, $-CH_2NHCO_2CH_2(CH_3)_2$, $-CH_2NHCO_2C_4H_9$, $CH_2NHCO_2$-adamantyl, $-CH_2NHCO_2-$(1-naphthyl), $-CH_2NHCONHCH_3$, $-CH_2NHCONHC_2H_5$, $-CH_2NHCONHC_3H_7$, $-CH_2NHCONHC_4H_9$, $-CH_2NHCONHCH(CH_3)_2$, $-CH_2NHCONH$(1-naphthyl), $-CH_2NHCONH$(1-adamantyl), $CO_2H$, $-CH_2CH_2CH_2CO_2H$, $-CH_2CH_2F$, $-CH_2OCONHCH_3$, $-CH_2CH_2CH_2F$, $-CH_2SH$ and

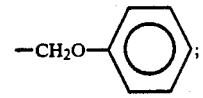

with the proviso that at least one of $R^5$, $R^6$, $R^8$ and $R^9$ is an acidic group selected from COOH and

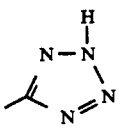

and wherein each of the remainder of $R^3$ through $R^{11}$ is hydrido, with the further proviso that at least one of said $R^1$ through $R^{11}$ is a substituent selected from COOH and moieties containing a terminal primary or secondary amino group; or a tautomer thereof or a pharmaceutically-acceptable salt thereof.

18. The composition of claim 16 wherein each G substituent is hydroxy.

19. The composition of claim 16 wherein each G substituent is hydroxy; wherein $R^{50}$ is hydrido; and wherein $R^{51}$ is selected from

wherein $R^{55}$ is selected from methyl, ethyl, n-propyl, isopropyl, n-butyl, sec-butyl, iso-butyl, tert-butyl, n-pentyl, neopentyl, n-hexyl and chloromethyl.

20. The composition of claim 16 wherein said second radical is

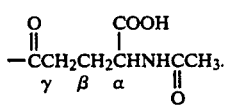

21. The composition of claim 16 wherein said first radical is a biphenylalkyl 1H-substituted-1,3-imidazole angiotensin II antagonist compound containing a terminal primary or secondary amino moiety attached at one of said $R^1$ through $R^{11}$ positions of Formula I, said amino moiety selected from amino and linear or branched aminoalkyl moieties containing linear or branched alkyl groups selected from aminomethyl, aminoethyl, aminopropyl, aminoisopropyl, aminobutyl, aminosecbutyl, aminoisobutyl, aminotertbutyl, aminopentyl, aminoisopentyl and aminoneopentyl.

22. The composition of claim 21 wherein each of $R^{200}$ and $R^{201}$ is hydrido.

23. The composition of claim 16 wherein said angiotensin II antagonist compound is 4'-[2-butyl-5-chloro-4-(hydroxymethyl)-1H-imidazol-1-ylmethyl][1,1'-biphenyl]-2-carboxylic acid or a pharmaceutically-acceptable salt thereof.

24. The composition of claim 23 wherein said conjugate is N-acetyl-L-glutamic acid, 5-[[4'-[2-butyl-5-chloro-4-(hydroxymethyl)-1H-imidazol-1-ylmethyl][1,1'-biphenyl]-2-yl]carbonyl]hydrazide or a pharmaceutically-acceptable salt thereof.

25. The composition of claim 23 wherein said conjugate is $N^2$-acetyl-N-[[2-butyl-5-chloro-1-[[2'-(1H-tetrazol-5-yl)[1,1'-biphenyl]-4-yl]methyl]-1H-imidazol-4-yl]methyl]-L-glutamine or a pharmaceutically-acceptable salt thereof.

26. The composition of claim 23 wherein said conjugate is N-acetyl-N-L-glutamic acid, 5-[2-butyl-5-chloro-1-[[2'-(1H-tetrazol-5-yl)[1,1-biphenyl]-4-yl]methyl]-1H-imidazol-4-yl]acetylhydrazide or a pharmaceutically-acceptable salt thereof.

27. The composition of claim 16 wherein said angiotensin II antagonist compound is 4'-[2-butyl-4-chloro-5-(hydroxymethyl)-1H-imidazol-1-ylmethyl][1,1'-biphenyl]-2-carboxylic acid or a pharmaceutically-acceptable salt thereof.

28. The composition of claim 12 wherein said conjugate is N-acetyl-L-glutamic acid, 5-[[4'-[2-butyl-4-chloro-5-(hydroxymethyl)-1H-imidazol-1-ylmethyl][1,1'-biphenyl]-2-yl]carbonyl]hydrazide or a pharmaceutically-acceptable salt thereof.

29. The composition of claim 27 wherein said conjugate is $N^2$-acetyl-N-[[2-butyl-4-chloro-1-[[2'-(1H-tetrazol-5-biphenyl-4-yl)methyl]-1H-imidazol-5-yl]methyl]-L-glutamine or a pharmaceutically-acceptable salt thereof.

30. The composition of claim 27 wherein said conjugate is N-acetyl-L-glutamic acid, 5-[2-butyl-4-chloro-1-[[2'-(1H-tetrazol-5-yl)[1,1'-biphenyl]-4-yl]methyl]-1H-imidazol-5-yl]acetylhydrazide or a pharmaceutically-acceptable salt thereof.

31. A method for treating a circulator disorder, said method comprising administering to a patient afflicted with or susceptible to said disorder a therapeutically-effective amount of a renal-selective conjugate, said renal-selective conjugate consisting of a first radical and a second radical, said first and second radicals connected together by a kidney-enzyme-cleavable bond, wherein said first radical is provided by a biphenylalkyl 1H-substituted-1,3-imidazole angiotensin II antagonist compound of Formula I:

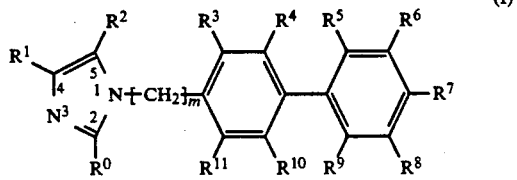

wherein m is one; wherein $R^0$ is selected from $C_4H_9(n)$, $CH_3CH_2CH=CH$, $C_3H_7(N)$, $SC_3H_7$,

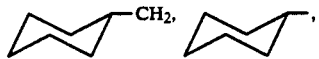

$C_2H_5$, $C_5H_{11}(n)$, $C_6H_{13}(n)$, $SC_4H_9$,

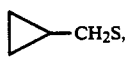

$CH_3CH=CH$ and $CH_3CH_2CH_2CH=CH—$; wherein $R^1$ is selected from amino, aminomethyl, aminoethyl, aminopropyl, $CH_2OH$, $CH_2OCOCH_3$, $CH_2Cl$, F, Cl, Br, I, $CH_2OCH_3$, $CH_2OCH(CH_3)_2$, CHO, $CH_2CO_2H$, $CH(CH_3)CO_2H$, $—CO_2CH_3$, $—CONH_2$, $—CONHCH_3$, $CON(CH_3)_2$, $—CH_2—NHCO_2C_2H_5$,

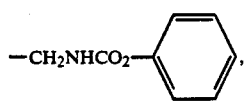

$—CH_2NHCO_2CH_3$, $—CH_2NHCO_2C_3H_7$, $—CH_2NHCO_2CH_2(CH_3)_2$, $—CH_2NHCO_2C_4H_9$, $CH_2NHCO_2$-adamantyl, $—CH_2NHCO_2$-(1-naphthyl), $—CH_2NHCONHCH_3$, $—CH_2NHCONHC_2H_5$, $—CH_2NHCONHC_3H_7$, $—CH_2NHCONHC_4H_9$, $—CH_2NHCONHCH(CH_3)_2$, $—CH_2NHCONH(1-naphthyl)$, $—CH_2NHCONH(1-adamantyl)$, $—CH_2CH_2CH_2CO_2H$, $—CH_2CH_2F$, $—CH_2OCONHCH_3$, $—CH_2CH_2CH_2F$, $—CH_2SH$ and

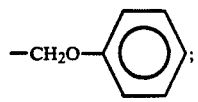

wherein $R^2$ is selected from H, F, Cl, Br, I, $NO_2$, $CF_3$, $CH_2OH$, methyl, ethyl, n-propyl, isoproyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, difluoromethyl, 1,1-difluoroethyl, 1,1-difluoropropyl, 1,1-difluorobutyl and 1,1-difluoropenyl; with the proviso that at least one of $R^5$, $R^6$, $R^8$ and $R^9$ is an acidic group selected from $CO_2H$, SH, $SO_3H$ and

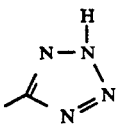

and wherein each of the remainder of $R^3$ through $R^{11}$ is hydrido, with the further proviso that at least one of said $R^1$ through $R^{11}$ is a substituent selected from COOH and moieties containing a terminal primary or secondary amino group; or a tautomer thereof or a pharmaceutically-acceptable salt thereof;

wherein said second radical is provided by a compound selected from a class of compounds of Formula II:

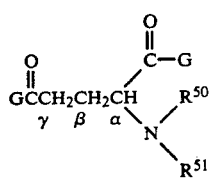

(II)

wherein each of $R^{50}$ and $R^{51}$ may be independently selected from hydrido, alkylcarbonyl, alkoxycarbonyl, alkoxyalkyl, hydroxyalkyl and haloalkyl; and wherein G is selected from hydrido, hydroxyl, halo, mercapto, $-OR^{52}$, $-SR^{53}$ and

with each of $R^{52}$, $R^{53}$ and $R^{54}$ independently selected from alkyl, and wherein each of $R^{53}$ and $R^{54}$ may be further independently selected from hydrido;

with the proviso that said kidney-enzyme-cleavable bond is within an amide group formed between said first and second radicals, wherein said first radical has a terminal primary or secondary amino moiety, wherein said first-radical amino moiety is provided by one of said $R^1$ through $R^{11}$ substituents of said Formula I compound or is provided by a linking moiety attached to a carbonyl group attached at one of said $R^1$ through $R^{11}$ substituents of said Formula I, and wherein said second radical has a carbonyl moiety attached at the gamma-position carbon of said Formula II compound, whereby said amide bond is formed from said first-radical amino moiety and said second radical carbonyl moiety; and wherein said linking moiety is a divalent radical of Formula III:

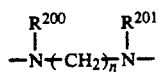

(III)

wherein each of $R^{200}$ and $R^{201}$ may be independently selected from hydrido, alkyl, cycloaklyl, cycloalkylalkyl, alkoxyalkyl, hydroxyalkyl and haloalkyl; and wherein n is a number selected from zero through six, inclusive;

or a pharmaceutically-acceptable salt of said renal-selective conjugate.

32. The composition of claim 16 wherein m is one; wherein $R^0$ is selected from $C_4H_9(n)$, $CH_3CH_2CH=CH$, $C_3H_7(N)$, $SC_3H_7$,

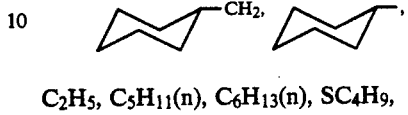

$C_2H_5$, $C_5H_{11}(n)$, $C_6H_{13}(n)$, $SC_4H_9$,

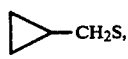

$CH_3CH=CH$ and $CH_3CH_2CH_2CH=CH-$; wherein $R^1$ is selected from H, $NO_2$, $CF_3$, $CH_2OH$, F, Cl, Br, I, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, difluoromethyl, 1,1-difluoroethyl, 1,1-difluoropropyl, 1,1-difluorobutyl and 1,1-difluoropenyl; wherein $R^2$ is selected from amino, aminomethyl, aminoethyl, aminopropyl, $CH_2OH$, $CH_2OCOCH_3$, $CH_2Cl$, $CH_2OCH_3$, $CH_2OCH(CH_3)_2$, F, Cl, Br, I, CHO, $CH_2CO_2H$ $CH(CH_3)CO_2H$, $-CO_2CH_3$, $-CONH_2$, $-CONHCH_3$, $CON(CH_3)_2$, $-CH_2NHCO_2C_2H_5$,

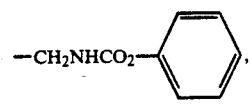

$CH_2NHCO_2CH_3$, $-CH_2NHCO_2C_3H_7$, $-CH_2NH\-CO_2CH_2(CH_3)_2$, $-CH_2NHCO_2C_4H_9$, $CH_2NHCO_2$-adamantyl, $-CH_2NHCO_2-$(1-naphthyl), $-CH_2NH\-CONHCH_3$, $-CH_2NHCONHC_2H_5$, $-CH_2NH\-CONHC_3H_7$, $-CH_2NHCONHC_4H_9$, $-CH_2NH\-CONHCH(CH_3)_2$, $-CH_2NHCONH($1-naphthyl$)$, $-CH_2NHCONH($1-adamantyl$)$, $CO_2H$, $-CH_2CH_2CH_2CO_2H$, $-CH_2CH_2F$, $-CH_2OCONHCH_3$, $-CH_2CH_2CH_2F$, $-CH_2SH$ and

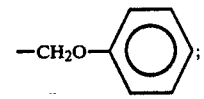

with the proviso that at least one of $R^5$, $R^6$, $R^8$ and $R^9$ is an acidic group selected from COOH and

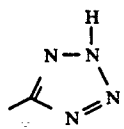

and wherein each of the remainder of $R^3$ through $R^{11}$ is hydrido, with the further proviso that at least one of said $R^1$ through $R^{11}$ is a substituent selected from COOH and moieties containing a terminal primary or secondary amino group; or a tautomer thereof or a pharmaceutically-acceptable salt thereof.

33. The composition of claim 31 wherein each G substituent is hydroxy.

34. The composition of claim 33 wherein each G substituent is hydroxy; wherein $R^{50}$ is hydrido; and wherein $R^{51}$ is selected from

wherein $R^{55}$ is selected from methyl, ethyl, n-propyl, isopropyl, n-butyl, sec-butyl, iso-butyl, tert-butyl, n-pentyl, neopentyl, n-hexyl and chloromethyl.

35. The composition of claim 31 wherein said second radical is

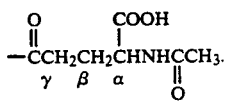

36. The composition of claim 31 wherein said first radical is a biphenylalkyl 1H-substituted-1,3-imidazole angiotensin II antagonist compound containing a terminal primary or secondary amino moiety attached at one of said $R^1$ through $R^{11}$ positions of Formula I, said amino moiety selected from amino and linear or branched aminoalkyl moieties containing linear or branched alkyl groups selected from aminomethyl, aminoethyl, aminopropyl, aminoisopropyl, aminobutyl, aminosecbutyl, aminoisobutyl, aminotertbutyl, aminopentyl, aminoisopentyl and aminoneopentyl.

37. The composition of claim 31 wherein each of $R^{200}$ and $R^{201}$ is hydrido.

38. The composition of claim 31 wherein said angiotensin II antagonist compound is 4'-[2-butyl-5-chloro-4-(hydroxymethyl)-1H-imidazol-1-ylmethyl][1,1'-biphenyl]-2-carboxylic acid or a pharmaceutically-acceptable salt thereof.

39. The method of claim 38 wherein said conjugate is N-acetyl-L-glutamic acid, 5-[[4'-[2-butyl-5-chloro-4-(hydroxymethyl)-1H-imidazol-1-ylmethyl][1,1'-biphenyl]-2-yl]carbonyl]hydrazide or a pharmaceutically-acceptable salt thereof.

40. The method of claim 38 wherein said conjugate is $N^2$-acetyl-N-[[2-butyl-5-chloro-1-[[2'-(1H-tetrazol-5-yl)[1,1'-biphenyl]-4-yl]methyl]-1H-imidazol-4-yl]methyl]-L-glutamine or a pharmaceutically-acceptable salt thereof.

41. The method of claim 38 wherein said conjugate is N-acetyl-N-L-glutamic acid, 5-[2-butyl-5-chloro-1-[[2'-(1H-tetrazol-5-yl)[1,1'-biphenyl]-4-yl]methyl]-1H-imidazol-4-yl]acetylhydrazide or a pharmaceutically-acceptable salt thereof.

42. The method of claim 31 wherein said angiotensin II antagonist compound is 4'-[2-butyl-4-chloro-5-(hydroxymethyl)-1H-imidazol-1-ylmethyl][1,1'-biphenyl]-2-carboxylic acid or a pharmaceutically-acceptable salt thereof.

43. The method of claim 42 wherein said conjugate is N-acetyl-L-glutamic acid, 5-[[4'-[2-butyl-4-chloro-5-(hydroxymethyl)-1H-imidazol-1-ylmethyl][1,1'-biphenyl]-2-yl]carbonyl]hydrazide or a pharmaceutically-acceptable salt thereof.

44. The method of claim 42 wherein said conjugate is $N^2$-acetyl-N-[[2-butyl-4-chloro-1-[[2'-(1H-tetrazol-5-biphenyl-4-yl)methyl]-1H-imidazol-5-yl]methyl]-L-glutamine or a pharmaceutically-acceptable salt thereof.

45. The method of claim 42 wherein said conjugate is N-acetyl-L-glutamic acid, 5-[2-butyl-4-chloro-1-[[2'-(1H-tetrazol-5-yl)[1,1'-biphenyl]-4-yl]methyl]-1H-imidazol-5-yl]acetylhydrazide or a pharmaceutically-acceptable salt thereof.

46. The method of claim 31 wherein said circulatory disorder is a hypertensive-related disorder.

47. The method of claim 46 wherein said hypertensive-related disorder is chronic hypertension.

* * * * *